US011638738B2

(12) United States Patent
Antony

(10) Patent No.: US 11,638,738 B2
(45) Date of Patent: May 2, 2023

(54) PROCESS TO ENHANCE THE BIOACTIVITY OF ASHWAGANDHA EXTRACTS

(71) Applicant: Benny Antony, Angamaly (IN)

(72) Inventor: Benny Antony, Angamaly (IN)

( * ) Notice: Subject to any disclaimer, the term of this patent is extended or adjusted under 35 U.S.C. 154(b) by 206 days.

(21) Appl. No.: 17/123,636

(22) Filed: Dec. 16, 2020

(65) Prior Publication Data
US 2021/0113646 A1 Apr. 22, 2021

Related U.S. Application Data

(60) Continuation of application No. 16/265,440, filed on Feb. 1, 2019, now abandoned, which is a division of application No. 15/326,450, filed as application No. PCT/IN2016/050354 on Oct. 18, 2016, now Pat. No. 10,251,927.

(30) Foreign Application Priority Data

Oct. 22, 2015 (IN) .......................... 5691/CHE/2015

(51) Int. Cl.
A61K 36/00 (2006.01)
A61K 36/81 (2006.01)
A61K 9/16 (2006.01)
A61K 9/20 (2006.01)
A61K 9/50 (2006.01)
A61K 36/21 (2006.01)
A61K 9/14 (2006.01)
A61K 9/28 (2006.01)
A61K 36/185 (2006.01)
A61K 36/23 (2006.01)
A61K 36/47 (2006.01)
A61K 36/48 (2006.01)
A61K 36/53 (2006.01)
A61K 36/534 (2006.01)
A61K 36/54 (2006.01)
A61K 36/67 (2006.01)
A61K 36/71 (2006.01)
A61K 36/82 (2006.01)
A61K 36/87 (2006.01)
(Continued)

(52) U.S. Cl.
CPC ................ A61K 36/81 (2013.01); A61K 9/14 (2013.01); A61K 9/16 (2013.01); A61K 9/2081 (2013.01); A61K 9/2846 (2013.01); A61K 9/50 (2013.01); A61K 9/5026 (2013.01); A61K 9/5036 (2013.01); A61K 9/5042 (2013.01); A61K 36/185 (2013.01); A61K 36/21 (2013.01); A61K 36/23 (2013.01); A61K 36/47 (2013.01); A61K 36/48 (2013.01); A61K 36/53 (2013.01); A61K 36/534 (2013.01); A61K 36/54 (2013.01); A61K 36/67 (2013.01); A61K 36/71 (2013.01); A61K 36/82 (2013.01); A61K 36/87 (2013.01); A61K 36/9066 (2013.01); A61K 36/9068 (2013.01); A61K 2236/00 (2013.01); A61K 2236/13 (2013.01); A61K 2236/15 (2013.01); A61K 2236/33 (2013.01); A61K 2236/331 (2013.01); A61K 2236/35 (2013.01); A61K 2236/51 (2013.01)

(58) Field of Classification Search
CPC .......... A61K 9/14; A61K 9/16; A61K 9/2081; A61K 9/50
See application file for complete search history.

(56) References Cited

U.S. PATENT DOCUMENTS 2,540,979 A 2/1951 Clymer et al.
6,153,198 A 11/2000 Ghosal
(Continued)

FOREIGN PATENT DOCUMENTS

WO WO 2005/034846 A3 4/2005
WO WO 2005/082392 A1 9/2005
(Continued)

OTHER PUBLICATIONS

Bhattacharya et al, Anti-stress activity of sitoindosides VII and VIII, new acylsterylglucosides from Withania somnifera. Phytotherapy research : PTR (1987), vol. 1, No. 1, pp. 32-37 (Year: 1987).*
Wankhede et al, Determination of triterpenoid saponins (*Quillaja saponaria Molina*) from roots of *Withania somnifera* (L.) Dunal by high performance liquid chromatography. Asian Journal of Chemistry (2011), vol. 23, No. 2, pp. 693-696 (Year: 2011).*
Bhattacharyya, S, Pal, D, Banerjee, D, Majumder, UK and Ghosal, S, Comparative effect of withania somnifera and panax ginseng on swim-stress induced impaired energy status of mice, Pharmacologyonline 2:421-432(2009).
Chatterjee, S, Srivastava, S, Khalid, A, Singh, N, Sangwan, RS, Sidhu, OP, Roy, R, Khetrapal, CL, Tuli, R, Comprehensive metabolic fingerprinting of Withama somnifera leaf and root extracts, Phytochemistry 71:1085-1094 (2010).
(Continued)

*Primary Examiner* — Qiuwen Mi
(74) *Attorney, Agent, or Firm* — Jyoti C. Iyer

(57) ABSTRACT

The invention relates to an extract of Ashwagandha that exhibit enhanced bioactivity and bioavailability comprising of enriched withanolide glycosides and saponins; with negligible amount of alkaloids, withanolide aglycones and oligosaccharides. The extract as disclosed prepared from root, stems, leaves and whole plant of Ashwagandha further shows improved immunomodulatory activity, anti-inflammatory activity, anti stress activity, antidiabetic activity and sleep quality. The disclosure also provides a method of improving bioactivity of withanolide glycosides even at lower doses, by the administration of an enteric coated formulation of extract of Ashwagandha to humans. The enteric coating protects the composition from hydrolysis in the acidic environment of the stomach to release the withanolide glycoside in neutral/alkaline pH in gastrointestinal tract (GIT) thus enhancing the absorption. Further the process of preparation of the extract of Ashwagandha enriched with withanolide glycosides and saponins are disclosed along with various formulations.

12 Claims, 10 Drawing Sheets

(51) Int. Cl.
    *A61K 36/9066* (2006.01)
    *A61K 36/9068* (2006.01)

(56) References Cited

U.S. PATENT DOCUMENTS

| | | | |
|---|---|---|---|
| 6,713,092 | B1 | 3/2004 | Ghosal |
| 7,108,870 | B2 | 9/2006 | Sangwan et al. |
| 7,318,938 | B2 | 1/2008 | Ghosal |
| 7,709,025 | B2 | 5/2010 | Fegely et al. |
| 8,206,757 | B2 | 6/2012 | McNeary |
| 8,501,186 | B2 | 8/2013 | Jadhav et al. |
| 8,597,697 | B2 | 12/2013 | McNeary |
| 8,636,985 | B2 | 1/2014 | Barron |
| 2007/0036873 | A1 | 2/2007 | Ghosal |
| 2011/0229591 | A1 | 9/2011 | Ravindranath et al. |
| 2012/0070521 | A1 | 3/2012 | Chitre et al. |
| 2014/0087009 | A1 | 3/2014 | McNeary |
| 2017/0157189 | A1 | 6/2017 | Antony |

FOREIGN PATENT DOCUMENTS

| | | | | |
|---|---|---|---|---|
| WO | WO 2010/013254 | A2 | | 2/2010 |
| WO | WO 10/068264 | A2 | | 6/2010 |
| WO | WO 2012/160569 | A1 | | 11/2012 |
| WO | WO-2012160569 | A1 | * 11/2012 | ............ A61K 36/81 |
| WO | WO 2015/115512 | A1 | | 8/2015 |
| WO | WO 16/051424 | A4 | | 4/2016 |

OTHER PUBLICATIONS

Uddin, Q, Samiulla, L, Singh, VK and Jamil, SS, Phytochemical and Pharmacological Profile of Withania somnifera Dunal: A Review, Journal of Applied Pharmaceutical Science 02 (01):170-175(2012).

Rao, S, Teesta, VK, Bhattrai, A, Khushi, K and Bhat, S, In Vitro Propagation of Withania Somnifera and estimation of Withanolides for Neurological disorders, Journal of Pharmacognosy 3 (2):85-87(2012).

Sumithradevi, S, Pradeepa, D and Senthil, K, A simple method to purify Withanolide A from the roots of Withania Somnifera Dunal, International Journal of Pharma and Bio Sciences,2(2):231-236(2011).

Al-Hindawi, MK, Al-Deen, IH, Nabi, MH, Ismal, MA, Anti-inflammatory activity of some Iraqi plants using intact rats, Journal of Ethnopharmacology, 26:163-168(1989).

Davis, L, Kuttan, G, Suppressive effect of cyclophosphamide-induced toxicity by Withania somnifera extract in mice, Journal of Ethnopharmacology, 62:209-214(1998).

Dhuley, JN, Effect of Ashwagandha on lipid peroxidation in stress-induced animals, Journal of Ethnopharmacology, 60:173-178(1998).

Khare, CP, Indian Medicinal Plants—An Illustrated Dictionary, First Indian Reprint, Springer (India) Pvt. Ltd., New Delhi, 717-718(2007).

Patel, JB, Lahiri, SK, Shah, MB, Development of a New Method for Identification and Estimation of Withania somnifera Root, and a Method for Quantitative Analysis of Withaferin A in Young and Old Roots, Journal of planar Chromatography, 22:283-286(2009).

Sharma,V, Gupta, AP, Bhandari, P, Gupta, RC, Singh, B, A validated and Densitometric HPTLC method for the quantification of Withaferin-A and Withanolide-A in different plant parts of two Morphotypes of Withania somnifera, Chromatographia, 66(9):801-804(2007).

Singh, A, Saharan, VA, Garg, R, Gupta, VB, Effect of time on extraction of Ashwagandha in various Hydroalcoholic compositions and their Anti-inflammatory activity, International Journal of Green Pharmacy, 69-74(Jan.-Mar. 2011).

Guang-Li, W, Song-Quan, W, Qiao-Feng, W, Separation, purification and identification of acidic polysaccharide fraction extracted from Boletus edulis and its influence on mouse lymphocyte proliferation in vitro, Journal of Chemical and Pharmaceutical Research, 5(12):431-437 (2013).

Pawar, HA, D'Mello, PM, Spectrophotometric estimation of total polysaccharides in Cassia tora gum, Journal of Applied Pharmaceutical Science 01 (03); 93-95(2011).

* cited by examiner

PROCESS TO ENHANCE THE BIOACTIVITY OF ASHWAGANDHA EXTRACTS

This Application is a continuation of U.S. application Ser. No. 16/265,440 filed Feb. 1, 2019, which is a divisional of U.S. application Ser. No. 15/326,450 filed Jan. 13, 2017, which is a 371 of International Application Ser. No. PCT/IN2016/050354 filed Oct. 18, 2016, which claims priority to Indian Provisional Appl. Ser. No. 5691/CHE/2015 filed Oct. 22, 2015, which are all incorporated in entirety by reference.

FIELD

Methods to enhance the bioactivity of Ashwagandha extract is provided. Compositions of Ashwagandha extract enriched with withanolide glycosides and saponins after removing alkaloids, withanolide aglycones and oligosaccharides are disclosed. Processes for manufacturing extracts of Ashwagandha enriched with withanolide glycosides, saponins and for removal of alkaloids, withanolide aglycones and oligosaccharides are provided. Some embodiments provide a process of extraction of Ashwagandha and enrichment mainly with withanolide glycosides to obtain a percentage of withanolide glycosides in a range of 0.5% and above and saponins in a range of 0.1 and above. The withanolide glycosides include withanoside I to VII and sitoindosides I to X. Methods of extraction of Ashwagandha extract enriched in withanolide glycosides and saponins but having alkaloids below 0.1%, withanolide aglycones below 0.1% and oligosaccharides below 0.1% are provided.

Some embodiments provide an enteric coated Ashwagandha extract composition to protect the withanolide glycosides from hydrolysis under acidic condition, preventing conversion of withanolide glycosides to aglycones and delivery of withanolide glycoside in neutral/alkaline pH in gastrointestinal tract (GIT). Some embodiments provide an enteric coated Ashwagandha extract composition to increase the bioactivity of withanolide glycosides by preventing conversion of withanolide glycosides to withanolide aglycones in acidic environment.

Enteric coated Ashwagandha extracts showed antistress activity, immunomodulatory activity, antidiabetic activity and anti-inflammatory activity even at a lower dosage level compared to extracts of Ashwagandha not coated with enteric coating. Methods of increasing the bioavailability and bioactivity of withanolide glycosides after administering enteric coated Ashwagandha extract composition at a lower dosage level than extracts of Ashwagandha that are not coated with enteric coating are provided. Suitable dosage forms of enteric coated Ashwagandha extract composition are provided.

Method of increasing the endurance after administering enteric coated Ashwagandha extract in combination with Amaranth extract at a lower dosage level is provided.

BACKGROUND

*Withania somnifera* a popular Indian medicinal plant also known as Ashwagandha, Indian ginseng, and winter cherry belongs to the Solanaceae or nightshade family. It has been an important herb in the ayurvedic and indigenous medical system for over 3000 years.

It is an erect, greyish, subshrub with inconspicuous yellow or greenish flowers followed by small, spherical, orangish-red berries containing yellow, kidney-shaped seeds. It grows three-to-five feet tall, mainly on waste land, but is cultivated widely as the whole plant; most commonly the root and leaf are used medicinally. The fruits from several of its species are edible, and some are used in traditional medicine.

The species name *somnifera* means "sleep-inducing" in Latin. The common name comes from the Sanskrit ashwagandha, i.e ashwa for horse, and gandha for smell, hence the common idea that the name means "smells like a horse." The species is widely distributed in the northwestern Indian states of Gujarat, Madhya Pradesh, Maharashtra, Rajasthan, Uttar Pradesh, and the Punjab plains extending to the mountainous regions of Himachal Pradesh and Jammu. It also is cultivated in parts of Madhya Pradesh and Rajasthan. Northwest of India, its habitat extends into the Pakistani provinces of Sindh and Baluchistan, and on into Afghanistan. To the southeast of India, it occurs in Sri Lanka. In China, it is reported to grow in the western provinces of Gansu and Yunnan.

Ashwagandha is one of the rasayana herbs in Ayurveda— one of the herbs that purportedly promotes youth and longevity and alleviates suffering. It is thought to be especially rejuvenative for men; to strengthen bone marrow, muscle, and semen; and to imbue the user with intellectual facility, in addition to long life and youthful vitality. However, it also is believed to be quite helpful to the elderly by providing energy and relieving pain, inflammation, and nervous debility.

The roots of this plant have been used as an adaptogen and to treat arthritis, asthma, dyspepsia, hypertension, rheumatism, and syphilis. Earlier pharmacological investigations of *Withania somnifera* have revealed its antiinflammatory, antioxidant, immunomodulatory, and tumor cell proliferation inhibitory activities.

The leaves are used to expel worms and are combined with warm castor oil (*Ricinis communis*, Euphorbiaceae) on carbuncles, inflammations, and swellings. The Masai use the leaf juice for conjunctivitis. The fresh bruised berries are used on ringworm. The fruits or seeds are used to coagulate milk. The seeds also are used as a masticatory. A bark infusion is used in Lesotho internally for asthma and externally for bedsores. The tender shoots are eaten as a vegetable in India.

The dried root and the whole plant are used in the traditional medicine systems of Ayurveda, Siddha, Sowa-Rigpa (Amchi), and Unani, as well as in Indian folk medicine. The materials of commerce are obtained from both cultivated and wild-collected sources, mainly in India.

In countries where the Ayurvedic system of medicine is officially recognized and practiced (e.g., India, Bangladesh, Bhutan, Malaysia, Nepal, and Sri Lanka), the powdered dried root of Ashwagandha is used, as a component of preparations, for treating inflammatory disorders, phthisis (any wasting or atrophic disease, weakness, diseases due to vata dosha), and male impotence.

In countries where the Unani system of medicine is officially recognized and practiced (e.g., Bangladesh, India, Malaysia, Pakistan, and Sri Lanka), the dried mature root, referred to as "asgand," is used as a component of medicinal formulations to treat leucorrhoea, spermatorrhoea, decreased viscosity of semen, sexual debility, lumbago, and arthritis.

In Siddha medicine—a Dravidian system of medicine originating in the southeastern Indian state of Tamil Nadu, now also practiced in the neighboring states of Karnataka, Kerala, and Andhra Pradesh, as well as in parts of Malaysia, Singapore, and Sri Lanka—the dried root (purified before use), referred to as amukkara, is used as a component of formulations indicated for treatment of conditions including oligospermia, lancinating pain, loss of body strength, anemia, convulsions/seizures/fits, disordered humor, eczema, edema/swelling, and tuberculosis.

Dhuley et al found that the root extract of Ashwagandha prevented the rise of experimentally induced LPO in rabbits & mice. Withaferin A and Sitoindoside VIII-X exhibits fairly potent anti-arthritic, anti-inflammatory, antioxidant & immuno modulant activities, they also increase in the levels of SOD, CAT, GPX in brain & the steroidal lactone W.A (Bhattacharya et al, 1997). The administration of Ashwagandha Rasayana significantly reduced the lung tumor nodule formation and also reduced leucopenia induced by cyclophosphamide treated experimental animals, indicating its usefulness in cancer therapy (Menon L, 1997 and Davis L, 1998). *Withania* increase the WBC count, reduce leucopenia. They also increased bone marrow cellularity & normalised the ratio of hormachromatic erythrocytes & polychromatic erythrocytes (Davis L, 1998). A methanolic & 80% ethanolic extract of *Withania somnifera* displayed significant anti-inflammatory activity on carrageenan-induced paw edema (Hindawi-al MKIH et al, 1989).

The main constituents of Aswagandha are alkaloids and steroidal lactones. Among the various alkaloids, withanine is the main constituent. The other alkaloids are somniferine, somnine, somniferinine, withananine, pseudowithanine, tropine, pseudotropine, 3agloyloxytropane, choline, cuscohygrine, isopelletierine, anaferine and anahydrine. Two acyl steryl glucoside viz. sitoindoside VII and sitoindoside VIII have been isolated from root. The leaves contain steroidal lactones, which are commonly called withanolides. The withanolides have C28 steroidal nucleus with C9 side chain, having six membered lactone rings. Withaferin A a steroidal lactone is the most important withanolide isolated from the extract of the leaves and dried roots of *Withania somnifera*.

Qamar et al in 2012 reported the active phytochemical and pharmacological components of *Withania somnifera*. The roots are reported to contain alkaloids, amino acids, steroids, volatile oil, starch, reducing sugars, glycosides, hentriacontane, dulcitol, withaniol, an acid and a neutral compound. Many biochemically heterogeneous alkaloids have been reported in the roots. Basic alkaloids include cuscohygrine, anahygrine, tropine, pseudotropine, anaferine, isopelletierine, withananine, withananinine, pseudowithanine, somnine, somniferine, somniferinine. Neutral alkaloids include 3-tropyltigloate and an unidentified alkaloid. Other alkaloids include withanine, withasomnine, and visamine. The leaves of the plant (Indian chemotype) are reported to contain 12 withanolides, 5 unidentified alkaloids, many free amino acids, chlorogenic acid, glycosides, glucose, condensed tannins, and flavonoids (Khare, 2007). The stem of the plant contains condensed tannins and flavonoids. The bark contains a number of free amino acids (Anonymous, 1982).

Patel et al. (2009) extracted powdered root of *W. somnifera* with ethylacetate and developed fingerprint profile and analysis of withaferin A in young and old root samples. Chatterjee et al. (2010) studied the metabolic fingerprinting of *W. somnifera* leaf and root extracts by using serial exhaustive extraction using hexane, 90% methanol, 70% methanol, chloroform and butanol. Rao et al. (2012) used methanol to extract withanolides from the roots of the *W. somnifera* and the extract was subjected to HPLC for detection. Singh et al. (2011) performed TLC to identify the different constituents present in different extracts of aswagandha roots. Different solvent systems such as acetonitrile:water (75:25) and toluene:ethyl acetate:acetic acid (65:33:2). HPTLC method has been developed by Sharma et al. (2007) for the estimation of withaferin-A and withanolide-A in different plant parts such as leaf, root, stem and fruit of two morphotypes of *W. somnifera*.

Ghosal et al, US patent publication 2004/0166184, reveals composition of *Withania somnifera* from roots and leaves containing 8-25% withanolide glycosides and sitoindosides, about 25-75% Oligosaccharides and less than 2% of free withanferin A (aglycone). Ghosal et al U.S. Pat. No. 6,153,198 discloses a high purity *Withania Somnifera* extract composition from root of Ashwagandha containing at least 3% withanolide glycoside and sitoindoside, at least 3% oligosaccharides and less than 0.5% of cytotoxic withferin A (aglycones) in the form of a high purity stable powder for producing an enhanced cognition effect for the use and to augment the learning facility. U.S. Pat. No. 7,108,870, Sangwan et al, reported an improved process of analytical and quantitative isolation of withaferin A from *Withania somnifera*. Patent publication US 20140087009, McNeary et al, discloses a composition including combinations of β-glucan and *Withania Somnifera* for increasing the immune activity of certain target cytokines ad phagocytosis and reducing cortisol or corticosterone. Sumithradevi et al reported a simple method to purify withanolide A from the roots of *Withania somnifera*. Uddin et al reported the phytochemical and pharmacological profile of *Withania somnifera*. WO2012160569, Jayesh Panalal et al discloses a process for extraction of Withanoside IV and V from Ashwagandha roots and its composition.

SUMMARY

A method to enhance the bioactivity of extracts of Ashwagandha is provided. Disclosure provides a stable composition obtained from the extract of Ashwagandha. Disclosure provides an extract of Ashwagandha enriched with withanolide glycosides and saponins from which alkaloids, withanolide aglycones and oligosaccharides are decreased or removed. Some embodiments of the extract of Ashwagandha contain withanolide glycoside in a range of about 0.5% and above, saponins in a range of 0.1 and above, alkaloids less than about 0.1%, withanolide aglycones less than about 0.1% and oligosaccharides less than about 0.1%.

The disclosure provides an enteric coated Ashwagandha extract in suitable dosage forms to obtain a stable composition. The disclosure provides methods for producing the Ashwagandha extract. The disclosure provides methods for producing the Ashwagandha extract enriched with withanolide glycosides content, saponin content, after removal of alkaloids, withanolide aglycones and oligosaccharides. The extract of Ashwagandha can be prepared from root, stems, leaves and whole plant of Ashwagandha. Disclosure provides a method of increasing the bioactivity of withanolide glycosides after administering enteric coated Ashwagandha extract composition even at a lower dosage level. Disclosure further provides an enteric coated Ashwagandha extract composition is found to have antistress activity, immunomodulatory activity, antidiabetic activity, anti-inflammatory activity etc even at a lower dosage level.

The disclosure provides an enteric coated Ashwagandha extract in combination with Amaranth extract for enhancing the endurance.

DETAILED DESCRIPTION

Figure 1:
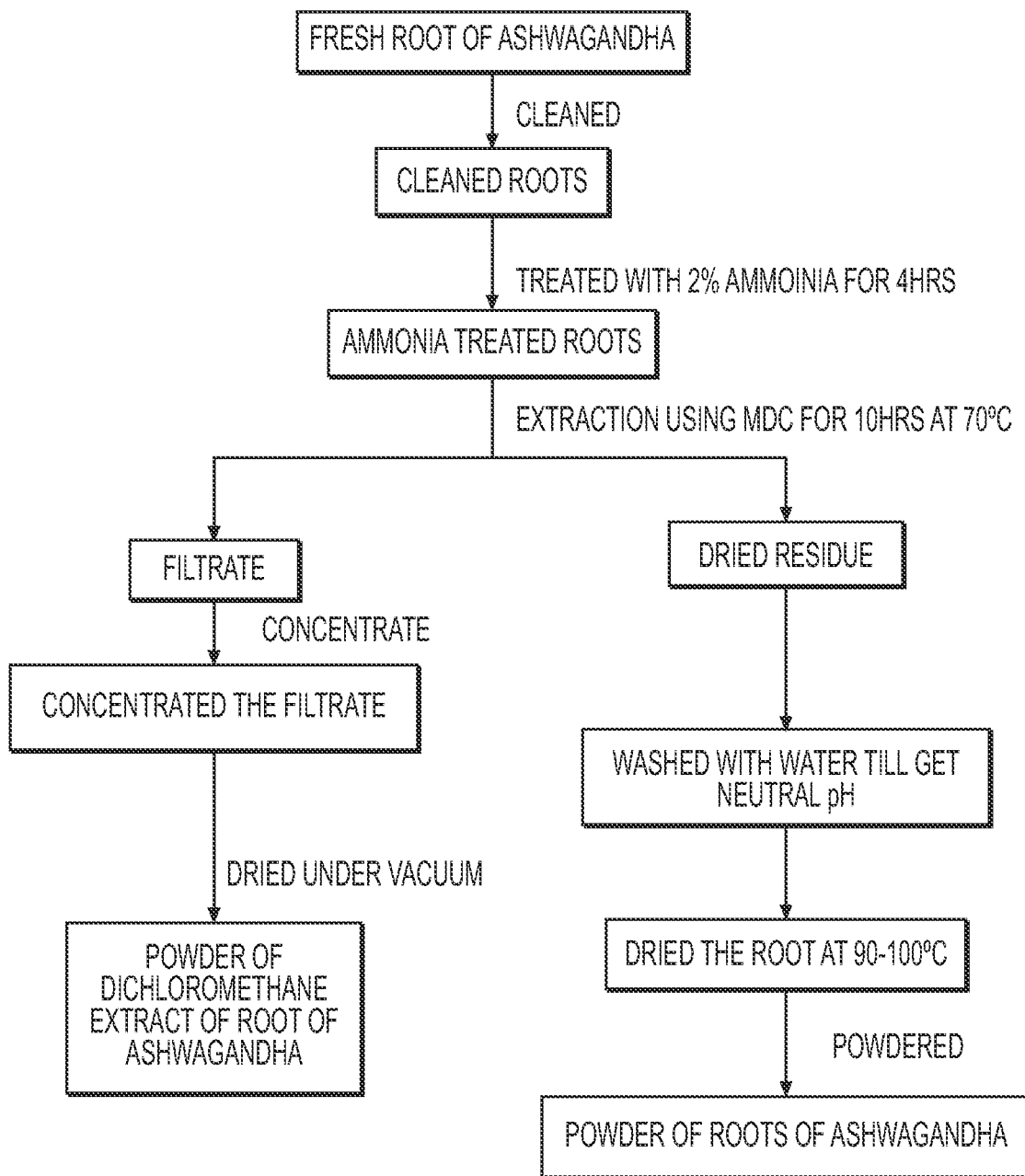
FIG. 1 provides method of preparation of dichloromethane extract of ammonia treated Ashwagandha root.

Though Ashwagandha extracts are known to have beneficial properties, we found during our studies that the alkaloids and fraction enriched with alkaloid components was having toxic effects in animals. The non alkaloid fraction was not showing toxicity but retained the beneficial effects of Ashwagandha and was found to be superior than the whole extract. The compounds identified from the Ashwagandha root extract which had toxicity included alkaloid compounds, withaferin A, withanine, withanolide aglycones. We removed toxic components from Ashwagandha through a novel extraction and purification process. At the same time percentage of active components like withanolide glycosides and saponins in the extract was enriched through the novel extraction and purification process.

Activity of different Ashwagandha extracts or powders in different pH was studied. Withanolide glycosides undergo hydrolysis in acidic pH and gets converted to withanolide aglycones. The withanolide aglycones have toxic effects. This conversion will happen in the acidic environment of the stomach after oral intake of regular Ashwagandha extract. An enteric coating can will prevent the contact of withanolide glycosides with acidic pH in stomach and release the contents in areas with neutral or mildly alkaline pH in the gastro intestinal tract from where it is absorbed.

An extract of Ashwagandha with enteric coating will release the actives (withanolide glycosides) in the small intestine without releasing in stomach thereby preventing the hydrolysis to aglycones and enhancing the absorption and oral bioavailability of withanolide glycoside in the body.

Methods to enhance the bioactivity of Ashwagandha extract are provided. A highly stable composition of Ashwagandha extract enriched with withanolide glycosides and saponins after removal of alkaloids, withanolide aglycones and oligosaccharides is provided. The disclosure also provides processes for manufacturing enriched extracts of Ashwagandha after the removal of alkaloids and oligosaccharides. Disclosure also relates enteric coated Ashwagandha extracts. The extracts are enriched with withanolide glycosides and saponins after the removal of alkaloids, withanolide aglycones and oligosaccharides.

An enteric coated Ashwagandha extract composition is provided. An enteric coating protects the withanolide glycosides from hydrolysis under acidic condition, preventing conversion of withanolide glycosides to aglycones and delivery of withanolide glycoside in neutral/alkaline pH in gastrointestinal tract (GIT). Some embodiments provide an enteric coated Ashwagandha extract composition to increase the bioavailability of withanolide glycosides at lower dosage level by preventing conversion of withanolide glycosides to withanolide aglycones in acidic environment. Enteric coated Ashwagandha extract composition is found to have antistress activity, immunomodulatory activity, antidiabetic activity, anti-inflammatory activity, to improve sleep quality etc. Methods of increasing the bioavailability and bioactivity of withanolide glycosides after administering enteric coated Ashwagandha extract composition are provided. Method of enhancing the endurance after administering enteric coated Ashwagandha extract in combination with Amaranth extract is provided.

The disclosure provides a method to enhance the bioactivity of Ashwagandha extract. Disclosure provides a stable Ashwagandha composition prepared by a unique method of extraction. The disclosed processes provide an enteric coated Ashwagandha extract enriched with withanolide glycosides include withanoside I to VII and sitoindoside I to X after removal of alkaloid, withanolide aglycones and oligosaccharides.

The disclosure relates to a composition of Ashwagandha root extract. The composition enriched with withanolide glycosides content (withanoside I to VII, sitoindosides I to X) after removal of alkaloid, withanolide aglycones and oligosaccharides.

Ashwagandha root extract is analysed by HPLC and found to contain withanolide glycosides (withanoside I to VII), sitoindosides (sitoindosides I to X) and the presence is confirmed by LCMS analysis. Ashwagandha extract contain saponins and it is analysed by UV method.

The disclosure provides Ashwagandha powder, Ashwagandha powder and/or extract and formulation. The disclosure also provides enteric coated powder or granules of extract of Ashwagandha powder. The enteric coated Ashwagandha extract was found to have antistress activity, immunomodulatory activity, antidiabetic activity, anti-inflammatory activity, to improve sleep quality etc. Ashwagandha extract without coating was also found to have anti stress activity, immunomodulatory activity, antidiabetic activity, anti-inflammatory activity, to improve sleep quality etc.

In some embodiments, Ashwagandha powder and/or extract is blended with a second extract. The second extract is selected from the group consisting of amla extract, turmeric extract, grape seed extract, green tea extract, pomegranate extract, Amaranth extract, costus extract, cocoa extract, coconut root extract, rosemary extract, mint leaf extract, star anise, sweet basil extract, cinnamon extract/clove extract, ginger extract, cumin seed extract, black pepper extract, fenugreek extract, or combinations thereof.

In another embodiment Ashwagandha powder and/or extract is blended with a second extract and the combination is coated with an enteric coating material. The enteric coated Ashwagandha powder and/or extract blended with a second extract is found to have antistress activity, immunomodulatory activity, antidiabetic activity, anti-inflammatory activity, to improve sleep quality etc.

In some embodiments, Ashwagandha extract can be fortified by adding Amaranth extract. Some embodiments provide combination of Ashwagandha extract and Amaranth extract for enhancing the endurance. Some embodiments provide combination of Ashwagandha extract and Amaranth extract for enhancing the endurance wherein the ratio of Ashwagandha extract to Amaranth extract is 1:1. In some embodiments, the weight ratio of Ashwagandha extract to Amaranth extract is 3:1. In another embodiment, the ratio of Ashwagandha extract to Amaranth extract is 1:3.

Some embodiments provides an enteric coated extract of Ashwagandha combined with Amaranth extract in different ratios. In some embodiments, the weight ratio of coated Ashwagandha extract to Amaranth extract is 3:1. In some embodiments the weight ratio of coated Ashwagandha extract to Amaranth extract is 1:1. In another embodiment, the ratio of coated Ashwagandha extract to Amaranth extract is 1:3.

The disclosure provides methods for producing the Amaranth extract. The extract of Amaranth can be prepared from fresh or dried leaves and stem of Amaranth.

In some embodiments of the extract of Amaranth, the Amaranth is selected from the group consisting of *Amaranthus caudatus, Amaranthus cruentus, Amaranthus tricolor, Amaranthus blitum, Amaranthus viridis, Amaranthus dubis* or combinations thereof.

In some embodiments of the extract of Amaranth, nitrates ranges from about 0.1% to about 3%. In some embodiments of the extract, nitrates ranges from about 1% to about 10%. In some embodiments of the extract, nitrates ranges from about 10% to about 20%. In some embodiments of the extract, nitrates ranges from about 3% to about 20%. In some embodiments of the extract, nitrates ranges from about 0.1% to about 80%.

In some embodiments the nitrate rich vegetables include juice, extract, powder and the like of Amaranth, Cabbage, Spinach, Beetroot, Artichoke, Asparagus, Broad Bean, Eggplant, holy basil, gymnema sylvestre, Garlic, Onion, gingko, Green Bean, Green tea, hawthorn berry, kelp, Mushroom, Pea, Pepper, Potato, Summer Squash, Sweet Potato, salvia, Tomato, tribulus, Watermelon, Broccoli, Carrot, Cauliflower, Cucumber, Pumpkin, Chicory, Dill, Turnip, Savoy Cabbage, Celeriac, Chinese Cabbage, Endive, Fennel, Kohlrabi, Leek, Parsley, Celery, Cress, Chervil, Lettuce, Rocket (Rucola), and the like.

In another embodiment, the nitrite salt is selected from the group consisting of sodium nitrite, potassium nitrite, magnesium nitrite, calcium nitrite, and mixtures thereof. In a particular embodiment, the nitrite salt is selected from the group consisting of sodium nitrite, potassium nitrite, and mixtures thereof.

The Ashwagandha extract or powder can be obtained from Ashwagandha whole plant or fresh root or dried root, stem or leaves of Ashwagandha or their combinations.

A regular extract of Ashwagandha contain a composition of withaferin A, withanolides, alkaloids, aminoacids, steroids, glycosides, condensed tannins, flavonoids and oligosaccharides. The components alkaloids and withaferin A (withanolides or withanolide aglycones) are found to be toxic. So we purified the extract by fractionation to remove the toxic components. This unique extraction process results an extract of Ashwagandha enriched with active components like withanolide glycosides and saponins, wherein withanolide glycoside include withanoside I-VII and sitoindosides I to X.

We found during our studies that the alkaloids and fraction enriched with alkaloid components was having toxic effects in animals. Animals fed with alkaloidal rich fraction has decrease in spontaneous movements, sluggish response to stimuli and diminished muscle tone. Whereas there is no toxic symptoms in animals fed with alkaloidal free purified Ashwagandha root extract with 80% withanolide glycosides, enteric coated alkaloidal free purified Ashwagandha root extract with 80% withanolide glycosides.

Animal fed with Ashwagandha root extract with minimum 5% withanolide glycosides or alkaloidal rich fraction shows loss of appetite whereas the animals fed with alkaloids free purified Ashwagandha root extract with 80% withanolide glycosides and enteric coated alkaloids free purified Ashwagandha root extract with 80% withanolide glycosides shows normal appetite. In our study we can observe that some animals fed with Ashwagandha root extract with minimum 5% withanolide glycosides and alkaloidal rich fraction died due to clonic convulsions and respiratory depression.

Some embodiments provide a composition obtained from the extract of Ashwagandha from roots of Ashwagandha. The extract has enriched withanolide glycoside and saponin content after removal of alkaloid content, withaferin A, withanolide aglycones wherein withanolide glycosides are present in the extract in a range of 30% and above, saponins are present in the range of 10% and above, alkaloids are present in the range of about 0.001% to about 0.1%, withanolide aglycones are present in the range of about 0.001% to about 0.1% and oligosaccharides are present in the range of less than 0.1%.

In some embodiments of the extract, withanolide glycosides range about 5% and above, saponins range about 2% and above, alkaloids are less than about 0.1%, withanolide aglycones range less than about 0.1%, and oligosaccharides are less than 0.1%. In some embodiments of extracts prepared from root and stem of Ashwagandha, withanolide glycosides are about 6%, oligosaccharides about 5% and withanolide aglycones about 0.2%, and a weight ratio of withanolide glycoside to aglycones is about 30:1, and, a weight ratio of withanolide glycoside to oligosaccharides is about 6:5.

In some embodiments of the Ashwagandha extract or enteric coated Ashwagandha compositions, withanolide glycosides ranges from about 0.5% to about 80%. In some embodiments of the Ashwagandha extract or enteric coated Ashwagandha compositions, withanolide glycosides range from about 0.5% to about 3.5%. In some embodiments of the Ashwagandha extract or enteric coated Ashwagandha compositions, withanolide glycosides range from about 0.5% to about 5%. In some embodiments of the Ashwagandha extract or enteric coated Ashwagandha compositions, withanolide glycosides range from about 3.5% to about 5%. In some embodiments of the Ashwagandha extract or enteric coated Ashwagandha compositions, withanolide glycosides range from about 0.5% to about 35%. In some embodiments of the Ashwagandha extract or enteric coated Ashwagandha compositions, withanolide glycosides range from about 3.5% to about 35%. In some embodiments of the Ashwagandha extract or enteric coated Ashwagandha compositions, withanolide glycosides range from about 5% to about 35%. In some embodiments of the Ashwagandha extract or enteric coated Ashwagandha compositions, withanolide glycosides ranges from about 30% to about 40%. In some embodiments of the Ashwagandha extract or enteric coated Ashwagandha compositions, withanolide glycosides ranges from about 30% to about 50%. In some embodiments of the Ashwagandha extract or enteric coated Ashwagandha compositions, withanolide glycosides ranges from about 30% to about 80%. In some embodiments of the Ashwagandha extract or enteric coated Ashwagandha compositions, withanolide glycosides are at least about 0.5%. In some embodiments of the Ashwagandha extract or enteric coated Ashwagandha compositions, withanolide glycosides are at least about 3.5%. In some embodiments of the Ashwagandha extract or enteric coated Ashwagandha compositions, withanolide glycosides are at least about 5%. In some embodiments of the Ashwagandha extract or enteric coated Ashwagandha compositions, withanolide glycosides are at least about 35%. In some embodiments of the Ashwagandha extract or enteric coated Ashwagandha compositions, withanolide glycosides are at least about 80%. In some embodiments, saponins ranges from about 0.1% to 2%. In some embodiments, saponins ranges from about 0.1% to 10%. In some embodiments, saponins ranges from about 2% to 30%. In some embodiments, alkaloids ranges from about 0.001% to about 0.05%. In some embodiments, alkaloids ranges from about 0.001% to about 0.1%. In some embodiments, withanolide aglycones ranges from about 0.001% to about 0.05%. In some embodiments, withanolide aglycones ranges from about 0.001% to about 0.1%. In some embodiments, oligosaccharides ranges from about 0.001% to about 0.05%. In some embodiments, oligosaccharides ranges from about 0.001% to about 0.1%.

Some embodiments provide a composition comprising an extract of root of *Withania somnifera*. The extract of root of *Withania somnifera* has at least about 35% withanolide glycosides and 10% saponins. The extract also has about 0.4% alkaloids. Withanolide aglycones and oligosaccharides were undetectable in the extract by HPLC method. The withanolide glycosides included sitoindoside I to X, withanoside I to VII and withanmides.

Some embodiments provide a composition of an extract of root of *Withania somnifera*. The extract has at least about 80% withanolide glycosides. The extract has about 15% saponins. The extract has about 0.001% alkaloids. Withanolide aglycones and oligosaccharides were undetectable in the extract by HPLC method. The withanolide glycosides included sitoindoside I to X, withanoside I to VII and withanmides.

Some embodiments provide an enteric coated composition of an extract of *Withania somnifera*. The extract of *Withania somnifera* includes withanolide glycosides. The enteric coated composition has an enteric coating material. The enteric coating material can be poly (methacrylic acid-co-methyl methacrylate), esters of aleurtic acid, cellulose acetate phthalate, cellulose acetate trimellitate, poly (vinyl acetate phthalate), hydroxypropyl methyl cellulose, hydroxypropyl methylcellulose phthalate, hydroxy propyl methyl cellulose acetate succinate, acetaldehyde dimethyl cellulose acetate, chitosan, zein, fatty acids, waxes, shellac, plastics, plant fibers, or, a combination of modified ethyl cellulose and sodium alginate. The extract of *Withania somnifera* in the enteric coated composition can include at least about 0.5% withanolide glycosides. In some embodiments of the enteric coated composition, the extract of *Withania somnifera* has at least about 3.5% withanolide glycosides. In some embodiments of the enteric coated composition, the extract of *Withania somnifera* has at least about 35% withanolide glycosides. In some embodiments of the enteric coated composition, the extract of *Withania somnifera* has at least about 80% withanolide glycosides. In some embodiments, the extract of *Withania somnifera* in the enteric coated composition has at least about 0.1% saponins; about 0.1% alkaloids; about 0.1% withanolide aglycones; and, about 0.1% oligosaccharides.

In some embodiments, the extract of *Withania somnifera* in the enteric coated composition has about 2.5% saponins; about 0.06% alkaloids; about 0.15% withanolide aglycones, and, about 3% oligosaccharides. In some embodiments, the extract of *Withania somnifera* in the enteric coated composition has about 10% saponins; about 0.4% alkaloids; and, withanolide aglycones and oligosaccharides were undetectable by HPLC method. In some embodiments, the extract of *Withania somnifera* in the enteric coated composition has about 15% saponins; about 0.001% alkaloids. In some embodiments, withanolide aglycones and oligosaccharides were undetectable by HPLC method. In some embodiments, the withanolide glycosides included sitoindoside I to X, withanoside I to VII and withanmides.

Some embodiments provide a composition having a combination of an extract of Amaranth and an enteric coated extract of *Withania somnifera*. Some embodiments of the combination of Amaranth extract and enteric coated extract of *Withania somnifera* provide improved endurance.

Some embodiments provide a method of preparing an extract of *Withania somnifera*. The method includes cleaning roots of *Withania somnifera*, followed by treating cleaned fresh roots of *Withania somnifera* with ammonia. Then extracting the cleaned fresh roots with methylene dichloride to obtain a filtrate and a residue. The residue is washed with water to obtain a wash having a pH ranging from about 6 to about 7. The washed residue is dried at about 90° C. to about 100° C. to obtain a dried residue. The dried residue is powdered to obtain an extract of roots of *Withania somnifera*. The extract of roots of *Withania somnifera* is a powder. In some embodiments the method further includes, preparing granules of the powder followed by spraying the granules with an enteric coating material to obtain an enteric coated composition. The extract of root of *Withania somnifera* has at least about 3% withanolide glycosides and at least about 1% saponins. Some embodiments provide an enteric coated extract of roots of *Withania somnifera*, wherein the extract of root of *Withania somnifera* has at least about 3% withanolide glycosides and at least about 1% saponins.

Some embodiments provide a method of preparing an extract of *Withania somnifera*. The method includes cleaning roots of *Withania somnifera*, followed by treating cleaned fresh roots of *Withania somnifera* with ammonia. Then extracting the cleaned fresh roots with methylene dichloride to obtain a filterate and a residue. The residue is washed with water to obtain a wash having a pH ranging from about 6 to about 7. The washed residue is dried at about 90° C. to about 100° C. to obtain a dried residue. The dried residue is powdered to obtain an extract of roots of *Withania somnifera*. The extract of roots of *Withania somnifera* is a powder. Some embodiments of the method further include extracting the powder with methanol at about 60° C. to about 70° C. to obtain a supernatant and a residue. Then concentrating the supernatant to obtain a concentrate. Next, drying the concentrate to obtain dried methanol extract in the form of a powder. In some embodiments the method further includes, preparing granules of the powder followed by spraying the granules with an enteric coating material to obtain an enteric coated composition. The extract of root of *Withania somnifera* has at least about 5% withanolide glycosides and at least about 1.5% saponins. Some embodiments provide an enteric coated extract of roots of *Withania somnifera*, wherein the extract of root of *Withania somnifera* has at least about 5% withanolide glycosides and at least about 1.5% saponins.

Some embodiments provide a method of preparing an extract of *Withania somnifera*. The method includes cleaning roots of *Withania somnifera*, followed by treating cleaned fresh roots of *Withania somnifera* with ammonia. Then extracting the cleaned fresh roots with methylene dichloride to obtain a filterate and a residue. The residue is washed with water to obtain a wash having a pH ranging from about 6 to about 7. The washed residue is dried at about 90° C. to about 100° C. to obtain a dried residue. The dried residue is powdered to obtain an extract of roots of *Withania somnifera*. The extract of roots of *Withania somnifera* is a powder. Some embodiments of the method further include extracting the powder with methanol at about 60° C. to about 70° C. to obtain a supernatant and a residue. Then concentrating the supernatant to obtain a concentrate. Next, drying the concentrate to obtain dried methanol extract in the form of a powder. The method further includes dissolving the dried methanol extract in water and clarifying the resulting product to obtain a supernatant and a residue. Then loading the supernatant onto an adsorbing column. Next, eluting the adsorbing column with water and then with 50% methanol. Next, concentrating and drying the 50% methanol elute to obtain a dried methanol extract of roots of *Withania somnifera*. The dried methanol extract is a powder. The adsorbing column can be silica, SP700, HP20, HP2MGL, SA10A, WA10, CRB03, CRB05, CR20, XAD 7HP, FP66, SK1B, or SP825L. In some embodiments the method further includes, preparing granules of the powder followed by spraying the granules with an enteric coating material to obtain an enteric coated composition. The extract of root of *Withania somnifera* has at least about 35% withanolide glycosides and at least about 10% saponins. Some embodiments provide an enteric coated extract of roots of *Withania somnifera*, wherein the extract of root of *Withania somnifera* has at least about 35% withanolide glycosides and at least about 10% saponins.

Some embodiments provide a method of preparing an extract of *Withania somnifera*. The method includes cleaning roots of *Withania somnifera*, followed by treating cleaned fresh roots of *Withania somnifera* with ammonia. Then extracting the cleaned fresh roots with methylene dichloride to obtain a filtrate and a residue. The residue is washed with water to obtain a wash having a pH ranging from about 6 to about 7. The washed residue is dried at about 90° C. to about 100° C. to obtain a dried residue. The dried residue is powdered to obtain an extract of roots of *Withania somnifera*. The extract of roots of *Withania somnifera* is a powder. Some embodiments of the method further include extracting the powder with methanol at about 60° C. to about 70° C. to obtain a supernatant and a residue. Then concentrating the supernatant to obtain a concentrate. Next, drying the concentrate to obtain dried methanol extract in the form of a powder. The method further includes dissolving the dried methanol extract in water and clarifying the resulting product to obtain a supernatant and a residue. Then loading the supernatant onto an adsorbing column. Next, eluting the adsorbing column with water and then with 50% methanol. Next, concentrating and drying the 50% methanol elute to obtain a dried methanol extract of roots of *Withania somnifera*. The dried methanol extract is a powder. The adsorbing column can be silica, SP700, HP20, HP2MGL, SA10A, WA10, CRB03, CRB05, CR20, XAD 7HP, FP66, SK1B, or SP825L. The method further includes dissolving the powder of the dried methanol extract in water, followed by centrifuging to obtain a supernatant and a residue. Next, loading the supernatant onto an adsorbing column. The adsorbing column of can be silica, SP700, HP20, HP2MGL, SA10A, WA10, CRB03, CRB05, CR20, XAD 7HP, FP66, SK1B, and SP825L. Next the adsorbing column is eluted with 10% methanol followed by eluting with 50% methanol to obtain a 50% methanol eluate. The 50% methanol eluate is dissolved in methanol, followed by concentrating the dissolved product. Next, acetone is added to the concentrated product to obtain a precipitate. The precipitate is filtered and dried to obtain a powder of the extract of roots of *Withania somnifera*. In some embodiments the method further includes, preparing granules of the powder followed by spraying the granules with an enteric coating material to obtain an enteric coated composition. The extract of root of *Withania somnifera* has at least about 80% withanolide glycosides and at least about 15% saponins. Some embodiments provide an enteric coated extract of roots of *Withania somnifera*, wherein the extract of root of *Withania somnifera* has at least about 80% withanolide glycosides and at least about 15% saponins.

Some embodiments provide a method of preparing an extract of *Withania somnifera*. The method includes cleaning roots of *Withania somnifera*, followed by treating cleaned fresh roots of *Withania somnifera* with ammonia. Then extracting the cleaned fresh roots with methylene dichloride to obtain a filtrate and a residue. The residue is washed with water to obtain a wash having a pH ranging from about 6 to about 7. The washed residue is dried at about 90° C. to about 100° C. to obtain a dried residue. The dried residue is powdered to obtain an extract of roots of *Withania somnifera*. The extract of roots of *Withania somnifera* is a powder. The method further includes, extracting the powder with 20% ethanol at about 75° C. to about 80° C. to obtain a supernatant and a residue. Then concentrating the supernatant to obtain a concentrated ethanol extract. Followed by drying the concentrated ethanol extract to obtain a powder of dried ethanol extract of roots of *Withania somnifera*. In some embodiments the method further includes, preparing granules of the powder followed by spraying the granules with an enteric coating material to obtain an enteric coated composition. The extract of root of *Withania somnifera* has at least about 3.5% withanolide glycosides and at least about 2.5% saponins. Some embodiments provide an enteric coated extract of roots of *Withania somnifera*, wherein the extract of root of *Withania somnifera* has at least about 3.5% withanolide glycosides and at least about 2.5% saponins.

Some embodiments provide a method of enhancing bioactivity of an extract of *Withania somnifera* by administering an enteric coated composition of the extract of *Withania somnifera*. Some embodiments provide a method of enhancing bioavailability of withanolide glycosides from an extract of *Withania somnifera* by administering an enteric coated composition of the extract of *Withania somnifera*. Some embodiments provide a method of delivering an extract of *Withania somnifera* into a medium having a pH ranging from about 6 to about 9 by administering an enteric coated composition of the extract of *Withania somnifera*. The extract of *Withania somnifera* is released from the enteric coated composition of the extract of *Withania somnifera* when the pH of the medium ranges from about 6 to about 9. Some embodiments provide a method of treatment by administering an extract of *Withania somnifera*. The conditions treated include improving immunomodulatory activity, improving anti inflammatory activity, improving anti stress activity, and treating diabetes. Immunomodulating activity includes an increase in bone marrow cells, an increase in the number of α-esterase positive cells, an increase in IgG and IgM antibody titre value, enhancement of the number of antibody producing cells. The improvement in anti stress activity is observed as enhanced anoxia stress tolerance time and enhanced swimming endurance time. Some embodiments provide a method of treatment by administering an enteric coated extract of *Withania somnifera*. The treatment method conditions include improving immunomodulatory activity, improving anti inflammatory activity, improving anti stress activity and treating diabetes. Improvement in immunomodulating activity includes an increase in bone marrow cells, an increase in the number of α-esterase positive cells, an increase in IgG and IgM antibody titre value, enhancement of the number of antibody producing cells. The improvement in anti stress activity includes enhanced anoxia stress tolerance time and enhanced swimming endurance time. Some embodiments provide a dosage form of the extract of *Withania somnifera* including capsule, tablet, mini tablet, granule, sachet, powder, paste, infusion, ampoule, solution, suspension, emulsion, pills or cream. Some embodiments include a dosage form of enteric coated extract of *Withania somnifera*. The dosage form of the enteric coated composition includes capsule, tablet, mini tablet, granule, sachet, powder, paste, infusion, ampoule, solution, suspension, emulsion, pills or cream. A dosage of the extract of *Withania somnifera* in the dosage form of compositions from about 200 mg to about 2000 mg. A dosage of the enteric coated extract of *Withania somnifera* in the dosage form of compositions from about 200 mg to about 2000 mg.

Activity of different Ashwagandha extract/powder in different pH was studied. Oral administration of Ashwagandha root powder (200 mg/kg) at pH 1, 2, 3 and 5 after reserpine injection was not much effective and immobility time was recorded as 245, 245, 230 and 220 seconds respectively. Administration of Ashwagandha root powders (200 mg/kg) at pH 7 and 7.4 after reserpine injection was slightly effective and immobility time was 205 seconds. Similarly, administration of Ashwagandha extract with 3.5% withanolide glycosides (60 mg/kg) at pH 1, 2, 3 and 5 after reserpine injection was slightly effective and immobility time was 235, 230, 210 and 189 seconds respectively. Whereas, administration of Ashwagandha extract with 3.5% withanolide glycosides (60 mg/kg) at pH 7 and 7.4 after reserpine injection was more effective and immobility time was recorded as 152 and 150 seconds respectively. Administration of Ashwagandha extract with 35% withanolide glycosides (20 mg/kg) at pH 1, 2, 3 and 5 after reserpine injection was effective and immobility time were 220, 220, 202 and 180 seconds respectively. Whereas, administration of Ashwagandha extract with 35% withanolide glycosides (20 mg/kg) at pH 7 and 7.4 after reserpine injection was more effective and immobility time were about 145 and 139 seconds respectively. In case of administration of extracts containing very high (80%) withanolide glycosides (20 mg/kg) at pH 1, 2, 3 and 5 after reserpine injection is effective and immobility time was about 212, 211, 194 and 165 seconds respectively. Whereas, administration of Ashwagandha extract with 80% withanolide glycosides (20 mg/kg) at pH 7 and 7.4 after reserpine injection was most effective and immobility time was about 110 and 105 seconds respectively. In case of fluoxetine standard at 10 mg/kg (Group XVII), the immobility time was only 122 seconds which was almost similar to normal control animals. The activity of Ashwagandha extract subjected to acidic buffer showed lesser activity compared to extract in subjected to neutral or basic buffer. The extract in neutral or basic pH shows higher activity.

From the above study we found that in acidic pH active component of Ashwagandha (Withanolide glycosides) undergo hydrolysis and get converted to withanolide aglycones. The withanolide aglycones have toxic effects. In order to protect the Ashwagandha extract in acidic medium different types of coating is applied to Ashwagandha extract and its activity is studied. Oral administration of Ashwagandha root powder with normal HPC coating (200 mg/kg) after reserpine injection was not much effective and immobility time was 245 seconds. Administration of Ashwagandha root powder with enteric coating (200 mg/kg) after reserpine injection was more effective than HPC coating and immobility time was recorded as 205 seconds. Administration of Ashwagandha root powder with delayed release coating (200 mg/kg) after reserpine injection was less effective than enteric coating and immobility time was recorded as 220 seconds.

Similarly, oral administration of Ashwagandha granules with 3.5% withanolide glycosides with normal HPC coating (60 mg/kg) after reserpine injection was not much effective and immobility time was recorded as 215 seconds. Administration of Ashwagandha granules with 3.5% withanolide glycosides with enteric coating (60 mg/kg) after reserpine injection was more effective than HPC coating and immobility time was recorded as 141 seconds. Administration of Ashwagandha granules with 3.5% withanolide glycosides with delayed release coating (60 mg/kg) after reserpine injection was less effective than enteric coating and immobility time was recorded as 186 seconds.

Oral administration of Ashwagandha granules with 35% withanolide glycosides with normal HPC coating (20 mg/kg) after reserpine injection is slightly effective and immobility time is recorded as 192 seconds (Group IX). Administration of Ashwagandha granules with 35% withanolide glycosides with enteric coating (20 mg/kg) after reserpine injection was more effective than HPC coating and immobility time is recorded as 138 seconds. Administration of Ashwagandha granules with 35% withanolide glycosides with delayed release coating (20 mg/kg) after reserpine injection is less effective than enteric coating and immobility time is recorded as 162 seconds.

Oral administration of Ashwagandha granules with 80% withanolide glycosides with normal HPC coating (20 mg/kg) after reserpine injection is effective and immobility time was recorded as 173 seconds. Administration of Ashwagandha granules with 80% withanolide glycosides with enteric coating (20 mg/kg) after reserpine injection is most effective than HPC coating and immobility time is recorded as 109 seconds. Administration of Ashwagandha granules with 80% withanolide glycosides with delayed release coating (20 mg/kg) after reserpine injection is less effective than enteric coating and immobility time is recorded as 132 seconds. In case of fluoxetine standard at 10 mg/kg, the immobility time is 120 seconds which is similar to normal control animals.

From the above study of Ashwagandha extract with different types of coating it is clear that enteric coated extract is found to be more stable in acidic medium. So in our next study we found the activity of Ashwagandha extract with different percentages of enteric coating (0.5% to 15%). Oral administration of Ashwagandha root powder with 0.5%, 1% and 3% enteric coating (200 mg/kg) after reserpine injection is not much effective and immobility time is recorded as 245, 235 and 223 seconds respectively. Administration of Ashwagandha root powder with 5 and 7% enteric coating (200 mg/kg) after reserpine injection is more effective than lower percentage of coatings and immobility time is recorded as 216 and 207 seconds respectively. Administration of Ashwagandha root powder with 10, 12 and 15% enteric coating (200 mg/kg) after reserpine injection is most effective and immobility time is recorded as 201, 200 and 200 seconds respectively. In case of fluoxetine standard at 10 mg/kg, the immobility time was 120 seconds which is similar to normal control animals.

Oral administration of Ashwagandha extract with 3.5% withanolide glycosides with 0.5%, 1% and 3% enteric coating (60 mg/kg) after reserpine injection is not much effective and immobility time is recorded as 225, 220 and 206 seconds respectively. Administration of Ashwagandha extract with 3.5% withanolide glycosides with 5 and 7% enteric coating (60 mg/kg) after reserpine injection is more effective than lower percentage of coatings and immobility time is recorded as 195 and 180 seconds respectively. Administration of Ashwagandha extract with 3.5% withanolide glycosides with 10, 12 and 15% enteric coating (60 mg/kg) after reserpine injection is most effective and immobility time is recorded as 160, 142 and 140 seconds respectively. In case of fluoxetine standard at 10 mg/kg, the immobility time is 120 seconds which is similar to normal control animals.

Oral administration of Ashwagandha extract with 35% withanolide glycosides with 0.5%, 1% and 3% enteric coating (20 mg/kg) after reserpine injection is not much effective and immobility time is recorded as 200, 188 and 180 seconds respectively. Administration of Ashwagandha extract with 35% withanolide glycosides with 5 and 7% enteric coating (20 mg/kg) after reserpine injection is more effective than lower percentage of coatings and immobility time is recorded as 171 and 160 seconds respectively. Administration of Ashwagandha extract with 35% withanolide glycosides with 10, 12 and 15% enteric coating (20 mg/kg) after reserpine injection is most effective and immobility time is recorded as 153, 139 and 136 seconds respectively. In case of fluoxetine standard at 10 mg/kg, the immobility time is 120 seconds which is similar to normal control animals.

Oral administration of Ashwagandha extract with 80% withanolide glycosides with 0.5%, 1% and 3% enteric coating (20 mg/kg) after reserpine injection is not much effective and immobility time is recorded as 195, 183 and 173 seconds respectively. Administration of Ashwagandha extract with 80% withanolide glycosides with 5 and 7% enteric coating (20 mg/kg) after reserpine injection is more effective than lower percentage of coatings and immobility time is recorded as 160 and 145 seconds respectively. Administration of Ashwagandha extract with 80% withanolide glycosides with 10, 12 and 15% enteric coating (20 mg/kg) after reserpine injection is most effective and immobility time is recorded as 122, 111 and 109 seconds respectively. In case of fluoxetine standard at 10 mg/kg, the immobility time was 120 seconds which is similar to normal control animals.

Some embodiments provide a composition obtained from the extract of Ashwagandha, encapsulating the composition by a polymeric enteric coating. Enteric coating protects a capsule contents in the highly acidic environment of the stomach. "Enteric" indicates small intestine; therefore enteric coatings prevent release of medication before it reaches the small intestine. Most enteric coatings work by presenting a coated surface that is stable at the highly acidic pH found in the stomach, but breaks down rapidly at a less acidic (relatively more basic) pH. The polymeric enteric coating material include Poly (methacrylic acid-co-methyl methacrylate) also known as Eudragit, Shellac (esters of aleurtic acid), CAP (Cellulose acetate phthalate), CAT (Cellulose acetate trimellitate), PVAP (Poly(vinyl acetate phthalate)), HPMCP (Hydroxypropyl methylcellulose phthalate), Hydroxy propyl methyl cellulose acetate succinate, Acetaldehyde dimethyl cellulose acetate, Chitosan, Zein, fatty acids, waxes, plastics, plant fibers and Modified ethyl cellulose and sodium alginate combination (Nutrateric) and their combinations in any possible ratios.

Some embodiments provide a composition obtained from the extract of Ashwagandha, encapsulating the composition by a simple coating (Film coating). The film coating material include Hydroxy propyl methyl cellulose, Hydroxy propyl cellulose, Methyl cellulose, Pectin, Starch, Hydrolyzed starch, Poly vinyl acetate (PVA), Poly vinyl pyrollidone (PVP), Poly vinyl alcohol, Cellulose acetate, Ethyl cellulose, Poly ethylene glycols (PEG), Glyceryl behenate, Hypromellose, Sodium alginate, Sodium propionate, Methacrylate amino ester copolymers, Methyl hydroxyl ethyl cellulose, Sodium carboxy methyl cellulose, Hydroxy ethyl cellulose, Sodium acetate, Sodium metaborate, Maltodextrin, Propylene glycoalginate, Polyvinylpyrrolidone-vinyl acetate copolymer, Polycaprolactones, Acrylic acid copolymer and their combinations in any possible ratios.

In one embodiment Ashwagandha root extract and purified Ashwagandha root extract is coated with enteric or nonenteric coating material.

Ashwagandha root extract or purified Ashwagandha root extract is loaded into the bowl of the fluid bed extractor (FBE). Hot, filtered air up to 90° C. is passed at high velocity from the bottom of the FBE bowl through the feed material (Ashwagandha root extract or purified root extract) and feed material is fluidised.

Meantime, any enteric or non enteric coating material is dissolved in suitable solvent. Coating solution is sprayed into fluidised material by using a spraying devise attached to the FBE. Through the process of fluid bed coating, fluidized particles are continuously sprayed with coating solution, depositing layers (films) of material to the surface of the particles, and yielding an even layer thickness.

The activity study shows that after administration of Ashwagandha root extract with minimum 6% withanolide glycosides at 100 mg/Kg dose and 20 mg/Kg dose, Ashwagandha root extract with minimum 6% withanolide glycosides coated with pectin after reserpine injection was not much effective and immobility time was recorded as above 240 seconds. Ashwagandha extract with 6% withanolide glycosides coated with Eudragit after reserpine injection, the immobility time was recorded as 195 seconds. When animals treated with Ashwagandha root extract containing minimum 1% withanolide glycosides, it is not effective and immobility time is found as 242 seconds. When animals treated with Ashwagandha root extract containing minimum 20% withanolide glycosides at 100 and 20 mg/kg dose the immobility time was 235 and 239 seconds respectively. But Ashwagandha root extract with 20% withanolide glycosides coated with Eudragit at 20 mg/kg dose, immobility time was reduced to 190 seconds. The immobility time is found as 175 and 210 seconds when animals treated with purified Ashwagandha extract with 35% withanolide glycosides at 100 and 20 mg/kg dose. When animals treated with purified Ashwagandha extract with 35% withanolide glycosides coated with pectin, HPMC and PVA at 20 mg/kg dose, the immobility time is 205, 207 and 204 seconds respectively which indicates very less effectiveness of such non-enteric coatings. In spite of nonenteric coatings, when animals treated with Ashwagandha extract with 35% withanolide glycosides coated with enteric materials shellac, CAP or Eudragit at 20 mg/kg dose, the immobility time is reduced to 162, 164 and 160 seconds respectively indicating the effectiveness of enteric coating. Animals treated with purified Ashwagandha extract with 80% withanolide glycoside at 100 and 20 mg/kg dose showed immobility time as 166 and 192 seconds respectively. When animals are treated with purified Ashwagandha extract with 80% withanolide glycoside coated with pectin, the immobility time is 189 seconds whereas when same extract is coated with Eudragit, the immobility time is reduced to 122 seconds only which shows the effectiveness of enteric coating.

An extract of Ashwagandha without enteric coating will release the actives (withanolide glycosides and sitoindosides) in the stomach. In the acidic environment of stomach withanolide glycosides will convert to withanolide aglycones, which is toxic.

But an extract of Ashwagandha with enteric coating will release the actives (withanolide glycosides and sitoindosides) in the small intestine without releasing the actives in the stomach. Enteric coatings in the extract prevent release of actives before it reaches the small intestine.

The conversion of withanolide glycosides into aglycon moiety and sugar is studied in simulated gastric fluid. It is found that at 15 minutes in acidic medium withanolide glycosides in tablet without any coating containing purified Ashwagandha root extract is converted into withanolide aglycones (33.8%), but only 1.2 percent of withanolide aglycones are formed following the administration of enteric coated tablet of alkaloid free purified Ashwagandha root extract. At 2 hours 74.8 percent of withanolide aglycones are formed in the acidic environment following the administration of tablet without any coating containing Ashwagandha root extract. After administration of enteric coated tablet of alkaloid free purified Ashwagandha root extract only 4.8 percent of withanolide aglycones are formed in the acidic condition.

An enteric coated Ashwagandha extract composition increases the bioavailability of withanolide glycosides. After administration of Ashwagandha extract with 6% withanolide glycosides or Ashwagandha root extract with 6% withanolide glycosides coated with pectin withanolide glycosides are not detected in the plasma. Animals fed with Ashwagandha root extract with 6% withanolide glycosides coated with Eudragit at 20 mg/kg, the withanolide glycoside level was found as 15.2 ng/ml. Withanolide glycosides are not detected in the plasma of animals fed with Ashwagandha extract with 3.5% withanolide glycoside at 100 and 20 mg/kg dose, whereas Ashwagandha root extract with 3.5% withanolide glycosides coated with Eudragit at 20 mg/kg, the withanolide glycoside level is found as 10.2 ng/ml. Animals fed with Ashwagandha extract with minimum 20% withanolide glycosides at 100 and 20 mg/Kg showed withnolide glycoside level in plasma as 1.9 and 0.3 ng/ml respectively. Animals fed with Ashwagandha extract with minimum 1%, and 20% withanolide glycoside coated with Eudragit at 20 mg/kg showed withnolide glycoside level in plasma as 1.6 and 4.2 ng/ml showing the effectiveness of enteric coating in preserving the withanolide glycosides from hydrolysis in the stomach. Animals fed with purified Ashwagandha extract with 35% withanolide glycoside at 100 and 20 mg/kg dose, the withanolide glycoside level in plasma is found as 60.3 and 12.4 ng/ml respectively. Animals fed with purified Ashwagandha extract with 35% withanolide glycoside coated with pectin, HPMC or PVA at 20 mg/kg dose showed plasma level of withanolide glycosides as 13.8, 12.9 and 13.2 ng/ml respectively. When the same extract, i.e. purified Ashwagandha extract with 35% withanolide glycoside is coated with enteric materials shellac, CAP or Eudragit, the plasma level of withanolide glycosides is increased to 100.3, 101.9 and 102.3 ng/ml respectively, indicating the effectiveness of enteric coating. When animals fed with purified Ashwagandha extract with 80% withanolide glycoside at 100 and 20 mg/kg dose, the plasma withanolide glycoside level is found as 85.2 and 18.5 ng/ml respectively. When the same extract (purified Ashwagandha extract with 80% withanolide glycoside) is coated with pectin and fed at only 20 mg/kg dose, the withanolide glycoside level is found as 17.3 ng/ml only showing the noneffectiveness of nonenteric coating. Whereas when animals fed with purified Ashwagandha extract with 80% withanolide glycoside coated with Eudragit at 20 mg/kg dose, the plasma withanolide glycoside level is found as 149.8 ng/ml showing the protective nature of enteric coating.

In one embodiment the extract of Ashwagandha can be administered as a minitablet form. In another embodiment the minitablets are prepared by mixing the Ashwagandha extract with binder and lubricant. The mixture is fed in tableting machine having 3 mm dies and punches to get the 3 mm diameter mini tablets with 9 Kg/cm' hardness. The binder and lubricant used is microcrystalline cellulose and Magnesium stearate.

In one embodiment mini tablets are coated by a coating material of 5-20%. In another embodiment minitablets are filled into a capsule for easy administration.

In some embodiments, the adsorbing material used for purifying Ashwagandha root extract are silica, SP700, HP20, HP2MGL, SA10A, WA10, CRB03, CRB05, CR20, XAD 7HP, FP66, SK1B, SP825L.

The disclosure provides different extracts of Ashwagandha extracted by using solvents like water, methanol, ethanol, chloroform, methylenedichloride, ethylene dichloride, isopropanol, n-butanol, methyl acetate, ethyl acetate, propyl acetate, n-butyl acetate, acetone, and combinations thereof.

Low molecular weight alcohols that can be used in preparation of the extract include methanol, ethanol, isopropanol, n-butanol and combinations thereof. Esters that can be used for extract preparation include methyl acetate, ethyl acetate, propyl acetate, n-butyl acetate and combinations thereof. Alkanes that can be used for preparation of the extract include pentane, hexane, heptane, isooctane, and combinations thereof.

In some embodiments, a dosage form of the Ashwagandha extract composition for oral administration in suitable dosage forms like capsule, tablet, mini tablet, granule, sachet, powder, paste, infusion, injection, ampoule, solution, suspension, emulsion, pills, cream etc is provided.

The disclosure provides an enteric coated Ashwagandha extract/Ashwagandha powder composition in suitable dosage forms like capsule, tablet, mini tablet, granule, sachet, powder, paste, infusion, ampoule, pills, cream etc.

These delivery systems may require excipients selected from the group consisting of a disintegrant, diluents, binders, fillers, a carrier, adsorbents, emulsifiers, lubricants, stabilizing agents, antiadherents, galidants, antioxidants and mixtures thereof.

Further a dosage form of an Ashwagandha extract is disclosed for administering in a dosage ranging from about 200 mg to about 2000 mg to a human subject.

The disclosure provides an enteric coated Ashwagandha extract enriched with withanolide glycosides, saponins and wherein alkaloids, withanolide aglycones and oligosaccharides were removed from the extract. The enteric coated Ashwagandha extract has antistress activity, immunomodulatory activity, antidiabetic, anti-inflammatory activity etc. The enteric coated Ashwagandha extract composition is used to improve sleep quality, maximal aerobic capacity (VO2 max), respiratory exchange ratio (RER), rate of perceived exertion (RPE), heart rate (HR), average absolute and relative power, total time to reach maximum exhaustion, rate pressure product (RPP), respiratory exchange ratio (pCO2/pO2), exercise Intensity, performance and endurance, cardiac output.

The disclosure also provides an Ashwagandha raw powder with enteric coating. An enteric coated Ashwagandha raw powder shows antistress activity, immunomodulatory activity, antidiabetic, anti-inflammatory activity, used to improve sleep quality etc.

Inflammation is a complex biological response of vascular tissues and immune cells to harmful stimuli, such as pathogens, damaged cells, or irritants. It is characterized by five signs: redness, increased heat, swelling, pain, and/or loss of function. Inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process. At present, the majority of medicines widely used as anti-inflammatory agents are nonsteroid anti-inflammatory drugs (NSAIDs) that have, as the mechanism of action, an inhibitory action on cyclooxygenases (COXs) that is involved in the biosynthesis of prostanoids. However, since prostanoid synthesis activity is present in various tissues in the living body and governs the homeostasis thereof, various side effects are induced when NSAID is administered. One test for inflammation is the C-reactive protein (CRP) measurement. Some clinicians are advocating including it routinely. The CRP test detects any inflammation, no matter where it is. A skinned knee, flu, arthritis and infections are common causes of elevated CRP. Anti-inflammatory activity of extracts/drugs can be evaluated in small animals like rats and mice. A classic model is carrageenan induced paw oedema model in rats. Carrageenan is an irritant and produces inflammation in rats paw after injecting a small volume into sub-plantar region. The volume of paw increases within 30 minutes of injecting carrageenan which can be measured by a plethysmometer. Volume of paw should be measured at various time points after carrageenan and test drug administration and should be compared with control.

An anti-inflammatory activity of enteric coated Ashwagandha root extract enriched with withanolide glycosides and saponins, wherein the alkaloids, withanolide aglycones and oligosaccharides were removed from the extract, showed higher percentage inhibition of inflammation. A higher value of percentage inhibition indicates more anti-inflammatory activity. Ashwagandha root extract with 3.5% withanolide glycoside coated with Eudragit is also found to be effective in reducing the inflammation in rat paw.

Stress is simply a reaction to a stimulus that disturbs the physical or mental equilibrium. It is considered to be any condition which results in perturbation of the body's homeostasis. Within seconds of an acutely stressful event, norepinephrine is released from nerve endings in preparation for a rapid response, and the adrenal glands release epinephrine and norepinephrine into the bloodstream, resulting in the familiar fight or flight response. Within minutes of a stressful event (and possibly lasting for several hours), a much more complex interaction between the nervous and endocrine systems and other forms of internal communication occurs, resulting in an intricate stress adaptation response. During this time the adrenal glands release extra cortisol into the circulation.

Several other endocrine glands are critical to the stress response. The hypothalamus, the "master gland" in the brain, responds to stress by releasing corticotropin-releasing factor (CRF). This hormone signals the pituitary gland to release adrenocorticotropic hormone (ACTH), which stimulates the adrenal glands to release cortisol. With the rise in stress hormones, a complex mechanism of feedback controls is set in motion, eventually signaling the hypothalamus to stop producing CRF. A wide range of events or conditions is considered physiologically stressful because the adrenals are stimulated to release stress hormones. These occurrences include calorie restriction, surgery, sleep deprivation, excessive exercise, and various mental states—all of which can result in elevated cortisol and catecholamine stress hormones.

Stress exerts a disruptive influence on normal circadian release of cortisol. A study conducted on military cadets subjected to a five-day training course of heavy physical exercise and food and sleep deprivation found cortisol levels went up and performance deteriorated due to the stressful nature of the training. The researchers also found, "the circadian rhythm was extinguished." Even after 4-5 days of rest, circadian rhythms had not completely normalized. This and other research demonstrates the physiological and psychological consequences of acute and chronic stress can persist well past cessation of a stressful event.

Stress is a factor in many illnesses—from headaches to heart disease, and immune deficiencies to digestive problems. A substantial contributor to stress-induced decline in health appears to be an increased production of stress hormones and subsequently decreased immune function. Research indicates a bout of acute stress of any kind will cause a temporary decrease in immune system functioning, while chronic stress will result in continued decline in immunity.

Overwhelming evidence demonstrates virtually any type of stress has a detrimental effect on the ability to maintain optimal levels of natural killer (NK) cell cytotoxic activity. A severe life stress may be associated with up to a 50-percent reduction of NK-cell activity. Since NK-cell activity plays a vital role in immune system surveillance against viruses and cancer cells, a sustained decrease in this aspect of immune performance can have serious consequences.

A high degree of stress predicted a lowered ability of NK cells to destroy cancer cells and significantly predicted a poorer response to interventions aimed at improving NK-cell activity. Chronic stress preceding an acutely stressful event can significantly impact NK-cell activity. Chronic stress may result in a greater sense of subjective distress, higher peak levels of epinephrine, a more pronounced immediate reduction in NK-cell activity, and a protracted decline of NK-cell activity in the individuals.

The ability to produce secretory IgA (sIgA) also appears to be influenced by stress. sIgA may be the single-most important aspect of humoral immunity in the mucus secretions of the digestive system, mouth, lungs, urinary tract, and other body cavities, and any decline in its levels can decrease resistance to microbial pathogens. Higher levels of the catecholamine stress hormone epinephrine are significantly associated with lower sIgA concentrations. Daily problems, lack of a sense of humor, and negative emotions can decrease sIgA levels.

Stress has a significant influence on the balance of intestinal microflora. In a study it was noted that, the composition of the flora was not significantly affected by drastic changes in diet, but statistically significant shifts in the proportions of some species were noted in individuals under conditions of anger or fear stress.

Anti-stress activity of enteric coated purified Ashwagandha root extract enriched with withanolide glycosides and saponins, wherein the alkaloids, withanolide aglycones and oligosaccharides were removed from the extract, showed enhanced anoxia stress tolerance time. An enhanced anoxia stress tolerance time indicates more antistress activity. Anoxia stress tolerance time was enhanced in group after administering Ashwagandha root extract with 3.5% withanolide glycosides coated with Eudragit.

Enteric coated purified Ashwagandha root extract enriched with withanolide glycosides and saponins showed significant enhanced swimming endurance time. Alkaloids, withanolide aglycones and oligosaccharides were removed from purified Ashwagandha root extract enriched with withanolide glycosides and saponins. Enhancement in swimming endurance time is also found in groups after administering Ashwagandha root extract with 3.5% withanolide glycoside (50 mg/kg) and coated Ashwagandha root extract with 3.5% withanolide glycoside (50 mg/kg). Alkaloidal rich fraction of Ashwagandha root extract has very little effect on increasing the swimming time.

Enteric coated purified Ashwagandha root extract enriched with withanolide glycosides and saponins, and from which alkaloids, withanolide aglycones and oligosaccharides were removed, showed a significant increase in the bone marrow cells compared to control animals. Moreover, the number of α-esterase positive cells are also found to be increased significantly in the enteric coated purified Ashwagandha root extract treated groups. Ashwagandha extract with 3.5% withanolide glycoside and Ashwagandha extract with 3.5% withanolide glycoside coated with Eudragit showed increase in the bone marrow cells compared to control animals. Ashwagandha extract with 3.5% withanolide glycoside with and without coating also showed increase in number of α-esterase positive cells compared to controls.

Maximum antibody titre value is observed with enteric coated purified Ashwagandha root extract treated groups. Ashwagandha root extract with 3.5% withanolide glycoside coated with Eudragit also showed a high antibody titre value. The maximum number of plaque forming cells (PFC) is found after administering enteric coated Ashwagandha root extract enriched with withanolide glycosides. Alkaloids, withanolide aglycones and oligosaccharides were removed from the purified Ashwagandha root extract enriched with withanolide glycosides. Ashwagandha root extract with 3.5% withanolide glycosides also showed an increased number of plaque forming cells (PFC).

Anti-diabetic activity of Ashwagandha root extract enriched with withanolide glycosides and saponins with or without coating, wherein the alkaloids, withanolide aglycones and oligosaccharides were removed from the extract, in streptozotocin induced diabetic rats shows that enteric coated Ashwagandha extract has more antidiabetic activity at lower dosages compared to Ashwagandha extract without coating. Treatment with Ashwagandha extract with minimum 1% withanolide glycosides at 100 mg/kg dose reduced the FBG from 423 to 302 mg/dl whereas the same extract after coating with Eudragit reduced the FBG from 428 to 300 mg/dl. Ashwagandha root extract with 5% withanolide glycosides at 100 mg/kg reduced the FBG from 425 to 224 mg/dl whereas coated product reduced the level from 423 to 222 mg/dl. Ashwagandha extract with minimum 3.5% withanolide glycosides at 100 mg/kg and its coated product at 20 mg/kg dose reduced the FBG from 425 to 163 and 426 to 162 mg/dl respectively. The purified Ashwagandha root extract with 35% withanolide glycoside given at 100 mg/kg reduced the FBG level from 424 to 120 mg/dl whereas purified Ashwagandha root extract with 35% withanolide glycoside coated with Eudragit given at 20 mg/kg for 28 days reduced the FBG from 424 to 119 mg/dl. Purified Ashwagandha root extract with 80% withanolide glycoside at 100 mg/kg and its coated product at 20 mg/kg are most effective and reduced the FBG level from 426 to 73 and 425 to 72 mg/dl respectively.

Antidiabetic activity of coated Ashwagandha extracts in different doses are studied in streptozotocin induced diabetic rats. Ashwagandha extract with 3.5% withanolide glycosides coated with Eudragit at 1, 5, 10, 20 and 40 mg/kg daily dosage for 28 days reduced the FBG level to 301, 250, 202, 164 and 145 mg/dl respectively. Purified Ashwagandha root extract with 35% withanolide glycoside coated with Eudragit was the most effective in reducing the FBG levels in rats. This product at 1, 5, 10, 20 and 40 mg/kg daily dosage reduced the FBG level to 250, 200, 160, 120 and 80 mg/dl respectively.

Method of enhancing the endurance after administering enteric coated Ashwagandha extract in combination with Amaranth extract is provided. After feeding with Ashwagandha extract with 3.5% withanolide glycosides coated with Eudragit at 20 mg/kg increased the swimming endurance and immobility time got reduced to 77.33 seconds. The immobility time in rats fed with Amaranth extract with 9% nitrate content at 50 mg/kg was recorded as 66.67 seconds.

Feeding of rats with a 1:1 combination of Ashwagandha extract with 3.5% withanolide glycosides coated with Eudragit and Amaranth extract with 9% nitrate content is most effective and it reduced the immobility time to 52.67 seconds.

In another embodiment Ashwagandha extract is tested in human subjects and found to have useful for sleep disorders, enhancing endurance, old age rejuvenation, immunomodulatory effects and it is described by the following studies.

Anti Infertility Study:

A multi-center randomized, parallel-group, double-blind, placebo-controlled study was done in 60 healthy stressed adults suffering from Infertility for 60 days.

Male volunteers with symptoms of anxiety (Total baseline score of 17 or greater on Hamilton Anxiety Rating Scale), low sperm concentration (sperm count; sperm/ml)<15 millions/ml; less sperm total motility was included in the study. Ashwagandha extract at a dose of 250 mg/day in 30 days improved the semen volume, improved Sperm motility with progressive sperm motility, increased total number of spermatozoa per ejaculate, improved sperm morphology, improved viability of spermatozoa, increased serum levels of total and free testosterone, reduced anxiety measured by HAM-A score and increased the number of spontaneous pregnancies.

Immunomodulatory Study:

A double-blinded randomized controlled trial for immunomodulatory effects of Ashwagandha (*Withania somnifera*) extract on 24 adult healthy volunteers was done at a dose of 250 mg/day for 60 days. There was a significant increase in the Th1 and Th2 cytokines after 30 days of Ashwagandha extract administration along with significant increase in T-helper cells and NK-cells.

Testosterone Study:

A double-blinded randomized placebo controlled trial to evaluate the effect of Ashwagandha extract 250 mg/day for 60 days on physical, sexual, vitality function and levels of testosterone was done in healthy adults. Volunteer were having serum testosterone levels that averaged less than 275 ng per deciliter. They also had self-reported decreased libido and a score of 20 or less on the sexual-desire domain (range, 0 to 33, with higher scores indicating greater desire) of the Derogatis Interview for Sexual Functioning in Men-II (DISF-M-II). They also reported difficulty walking or climbing stairs, reported low vitality and a score of less than 40 on the Functional Assessment of Chronic Illness Therapy (FACIT) Fatigue scale (range, 0 to 52, with higher scores indicating less fatigue). The volunteers on Ashwagandha extract showed improvement in Sexual Function shown as an improvement in total score on the Psychosexual Daily Questionnaire (PDQ-Q4); Improvement in physical function showed by increase in the percentage of men who had an increase of at least 50 m in the distance walked during the 6-minute walk test (6-MWT); Improvement in Vitality Function showed as increase in the percentage of men who had an increase of at least 4 points in the score on the Functional Assessment of Chronic Illness Therapy (FACIT)—Fatigue scale; Improvement in the erectile-function domain (range, 0 to 30, with higher scores indicating better function) of the International Index of Erectile Function (IIEF); Improvement in score on the sexual-desire domain of the DISF;

Increase in Change in serum Testosterone and Free-testosterone levels within 30 days of treatment.

Anti Anxiety Study:

A randomized, double-blind, placebo-controlled study evaluating the efficacy, safety, tolerability, and pharmacological actions of an Ashwagandha (*Withania somnifera*) extract was done in healthy, stressed adult volunteers. 60 healthy subjects with a total score between 6 to 17 on the Hamilton Rating Scale of Anxiety was given 250 mg/day of Ashwagandha extract for 60 days. There was significant improvement in total score on Hamilton Anxiety Rating Scale (HAM-A), improvement in total score and subscale scores on the Depression Anxiety Stress Scale (DASS-21), reduction in blood cortisol and DHEA-s levels and improvement in testosterone levels within 30 days.

Various methods for the preparation of the extract enriched with withanolide glycosides content and without alkaloid content prepared by the extraction of root of Ashwagandha are as under:

FIG. 1 describes a method of preparation of Ashwagandha root powder after ammonia treatment and MDC extraction. Fresh root of Ashwagandha is treated with 2% ammonia solution in ratio of 1:2 (2% ammonia:root) for 4 hrs. The ammonia treated Ashwagandha root is extracted with methylene dichloride (dichloro methane) at a temperature of 70-80° C. in a Soxhlet extractor for 10 hrs to form residue and filtrate. The filtrate and residue is separated. The residue is washed with water till the pH become neutral. Then dried the residue in vacuum oven at 90-100° C. After drying the residue (root of Ashwagandha) is powdered to form a powder of root of Ashwagandha.

The filtrate is concentrated in an Agitated thin film evaporator (ATFE) at a temperature of 40-50° C. to form concentrated dichloro methane (MDC) extract. Concentrated MDC extract is dried under vacuum at above 500 mm of mercury to form powder of "dichloromethane extract" of Ashwagandha.

Figure 2:
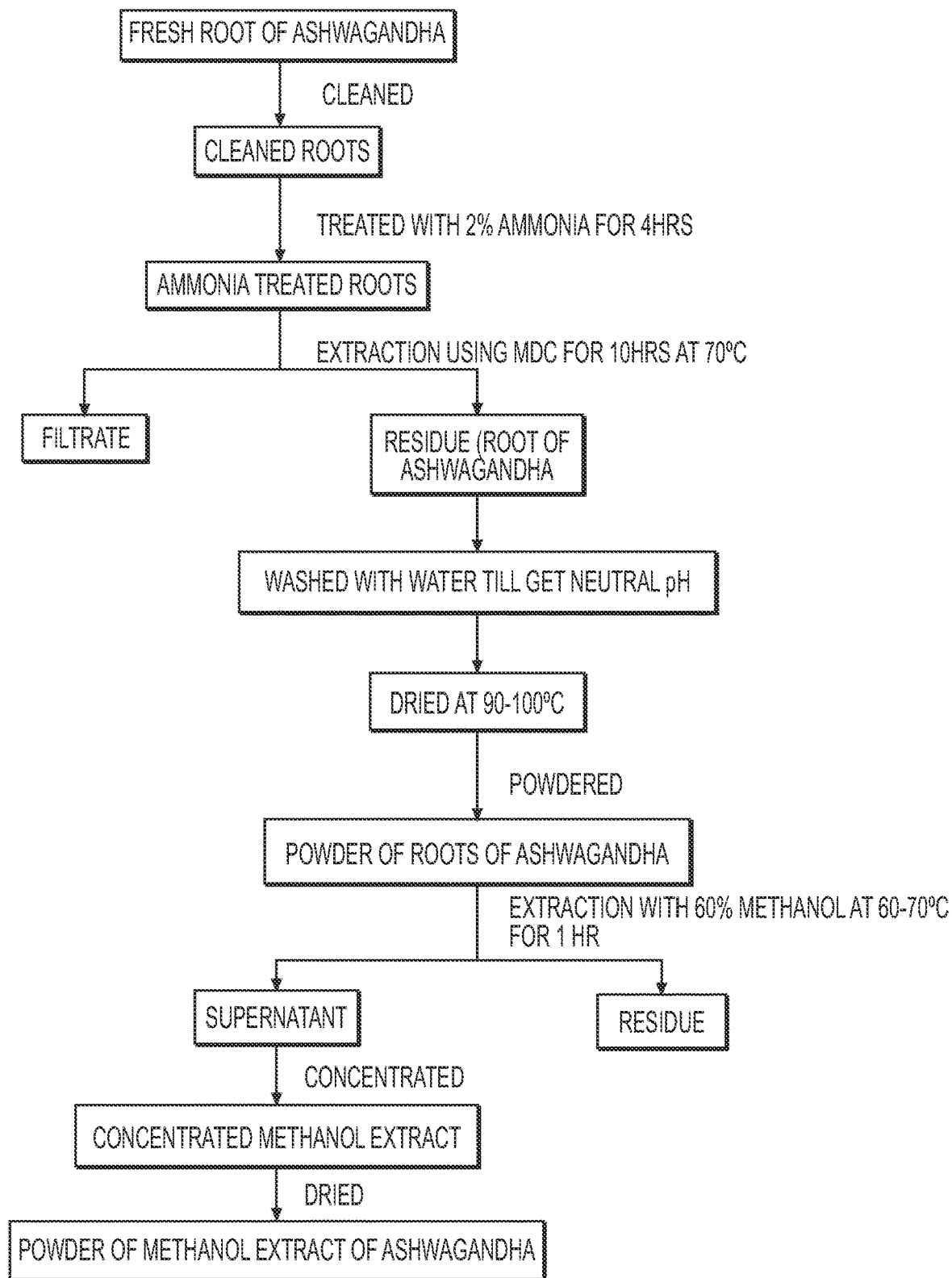
FIG. 2 provides method of preparation of 60% methanol extract of ammonia treated Ashwagandha root.

FIG. 2 describes a method of preparation of 60% methanol extract of Ashwagandha root extract after ammonia treatment and MDC extraction. Fresh root of Ashwagandha is treated with 2% ammonia solution in ratio of 1:2 (2% ammonia:root) for 4 hrs. The ammonia treated Ashwagandha root is extracted with methylene dichloride (dichloro methane) at a temperature of 70-80° C. in a Soxhlet extractor for 10 hrs to form residue and filtrate. The filtrate and residue is separated. The residue is washed with water till the pH become neutral. Then dried the residue in vacuum oven at 90-100° C. After drying the residue (root of Ashwagandha) is powdered to form a powder of root of Ashwagandha.

Powder of root of Ashwagandha is extracted with 60% methanol for one hour. The root and methanol part (supernatant) obtained are separated. Supernatant is concentrated in an Agitated thin film evaporator (ATFE) to form a concentrated methanol extract. The concentrated methanol extract is dried under vacuum at above 500 mm of mercury to get powder of 60% methanol extract of Ashwagandha.

Figure 3:
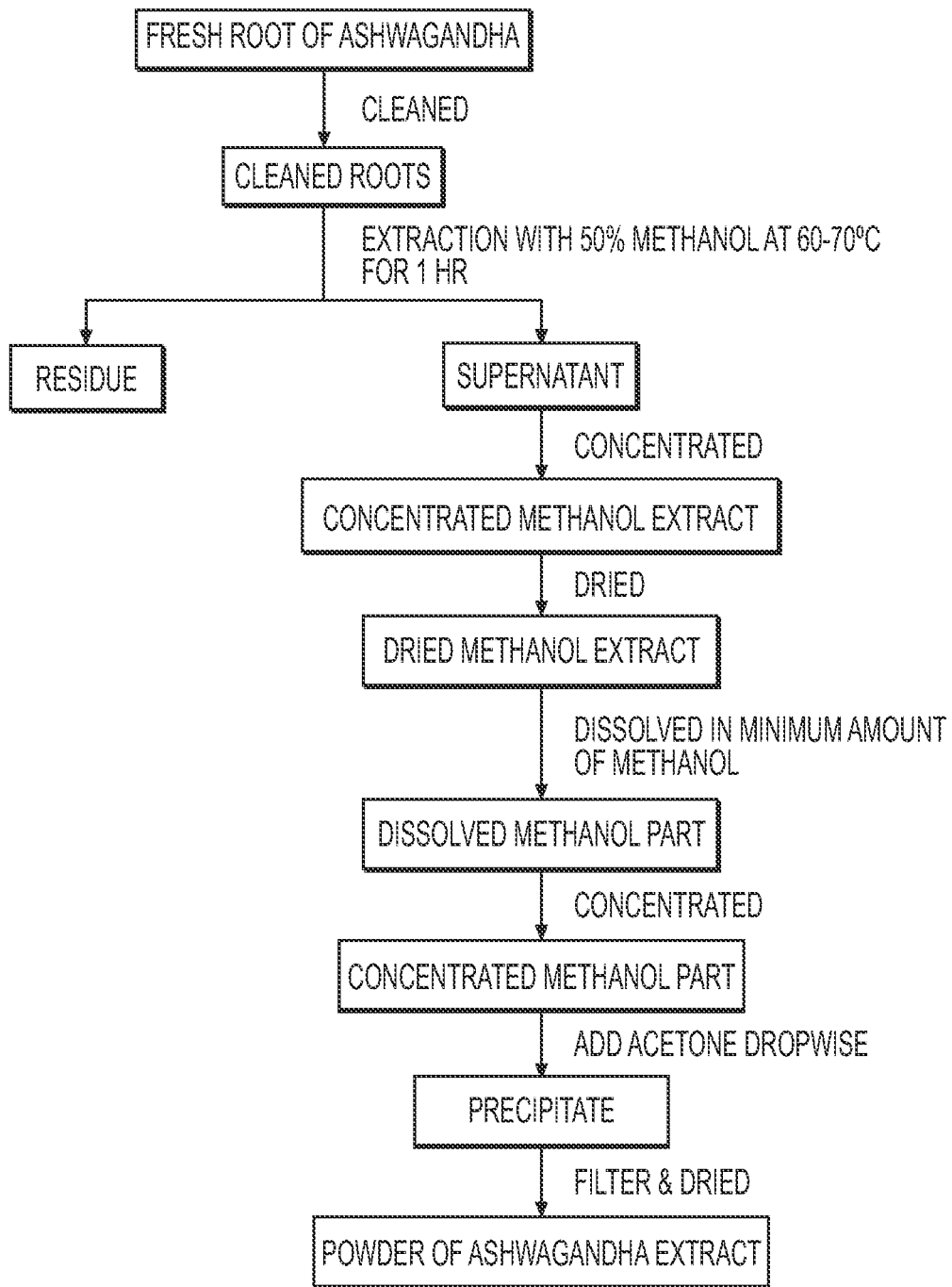
FIG. 3 provides method of preparation of 50% methanol extract of Ashwagandha root.

FIG. 3 describes a method of preparation of 50% methanol extract of Ashwagandha root extract. Root of Ashwagandha is extracted with 50% methanol for one hour. The root and methanol part (supernatant) obtained are separated. Supernatant is concentrated in an Agitated thin film evaporator (ATFE) to form a concentrated methanol extract. The concentrated methanol extract is dried under vacuum at above 500 mm of mercury to get powder of 50% methanol extract of Ashwagandha.

Powder of 50% methanol extract of Ashwagandha is dissolved in minimum amount of methanol. The dissolved methanol part is concentrated in an Agitated thin film evaporator (ATFE) to form a concentrated methanol extract. Acetone is added dropwise to the concentrated methanol extract until the precipitation is complete. Then, the precipitate was filtered and dried under vacuum at above 500 mm of mercury to get powder of Ashwagandha extract.

Figure 6:
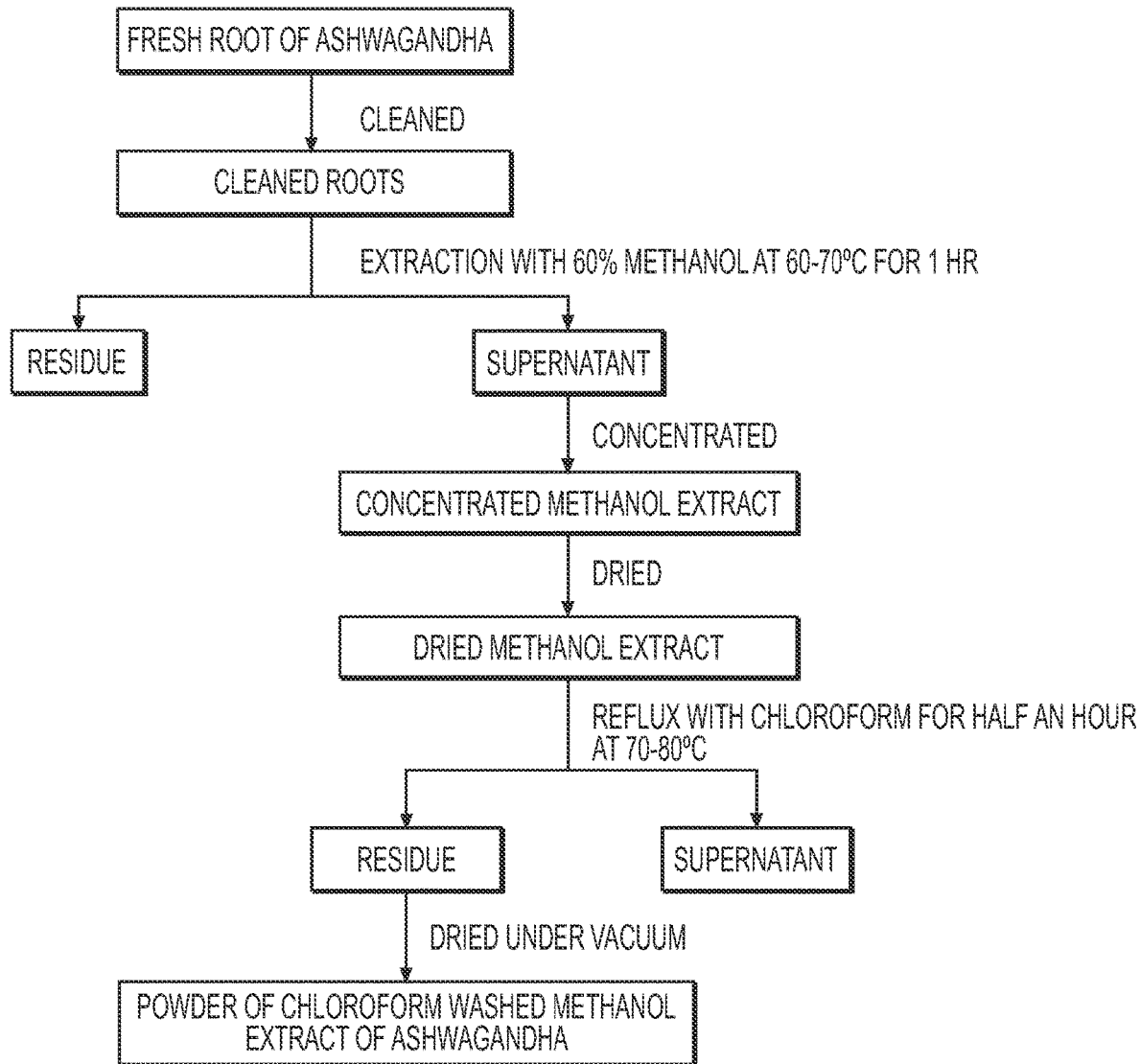
FIG. 6 provides method of preparation of chloroform extract of 60% methanol extract of Ashwagandha root.

FIG. 6 describes a method of preparation of chloroform insoluble extract of 60% methanol extract of Ashwagandha root extract. Roots of Ashwagandha is extracted with 60% methanol for one hour. The root and methanol part (supernatant) obtained are separated. Supernatant is concentrated in an Agitated thin film evaporator (ATFE) to form a concentrated methanol extract. The concentrated methanol extract is dried under vacuum at above 500 mm of mercury to get powder of 60% methanol extract of Ashwagandha.

Powder of 60% methanol extract of Ashwagandha is refluxed with chloroform at the boiling temperature (70-80° C.) of chloroform for half an hour. The residue (chloroform insoluble) and supernatant (chloroform soluble) are separated. The residue is dried under vacuum at above 500 mm of mercury to get powder of chloroform extract of 60% methanol extract of Ashwagandha.

Figure 4:
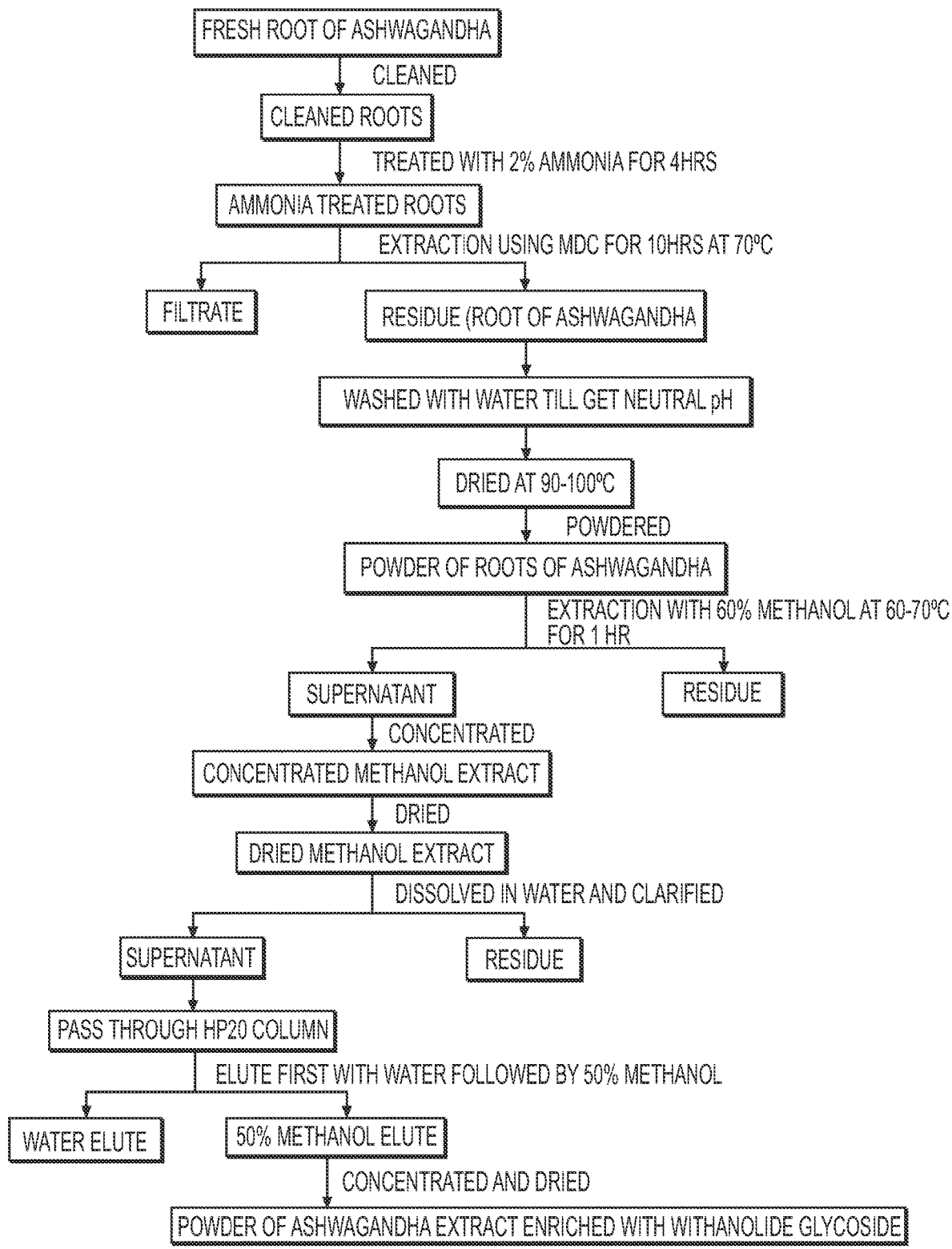
FIG. 4 provides method of preparation of purified 50% methanol extract of ammonia treated Ashwagandha root.

FIG. 4 describes a method of preparation of purified methanol extract of Ashwagandha root extract after ammonia treatment and MDC extraction. Fresh root of Ashwagandha is treated with 2% ammonia solution in ratio of 1:2 (2% ammonia:root) for 4 hrs. The ammonia treated Ashwagandha root is extracted with methylene dichloride (dichloro methane) at a temperature of 70-80° C. in a Soxhlet extractor for 10 hrs to form residue and filtrate. The filtrate and residue is separated. The residue (Ashwagandha root) is washed with water till the pH become neutral. Then dried the residue (Ashwagandha root) in vacuum oven at 90-100° C. After drying the residue (root of Ashwagandha) is powdered to form a powder of root of Ashwagandha. (Sample 1).

Powder of roots of Ashwagandha (sample 1) is extracted with 60% methanol for one hour. The residue and supernatants obtained are separated. Supernatant is concentrated in an Agitated thin film evaporator (ATFE) to form a concentrated methanol extract. The concentrated methanol extract is dried under vacuum at above 500 mm of mercury to get powder of 60% methanol extract of Ashwagandha. (Sample 2)

Sample 2 is dissolved in water and clarify. The supernatant obtained after clarification is loaded on a HP20 resin column. Column is initially eluted with water followed by 50% methanol. 50% methanol fraction is collected and concentrated in an Agitated thin film evaporator (ATFE) to form concentrated methanol extract. Concentrate methanol fraction is fed into vacuum stripper and dried under vacuum at above 500 mm of mercury to get powder of 50% methanol extract (sample 3) of Ashwagandha.

Figure 5:
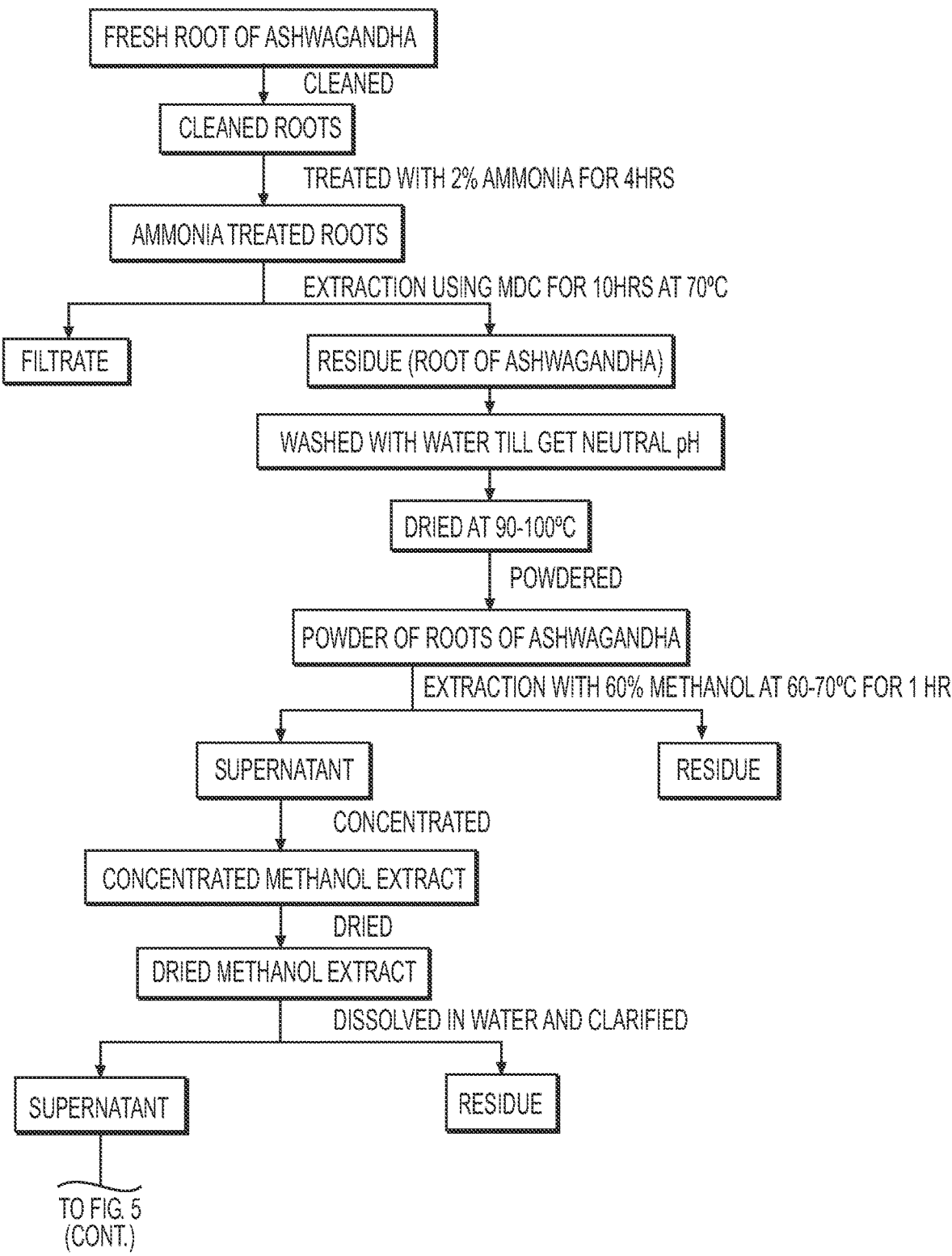
FIG. 5 and FIG. 5(CONT.) provide method of preparation of column purified 50% methanol elute of ammonia treated Ashwagandha root.
Figure 5:
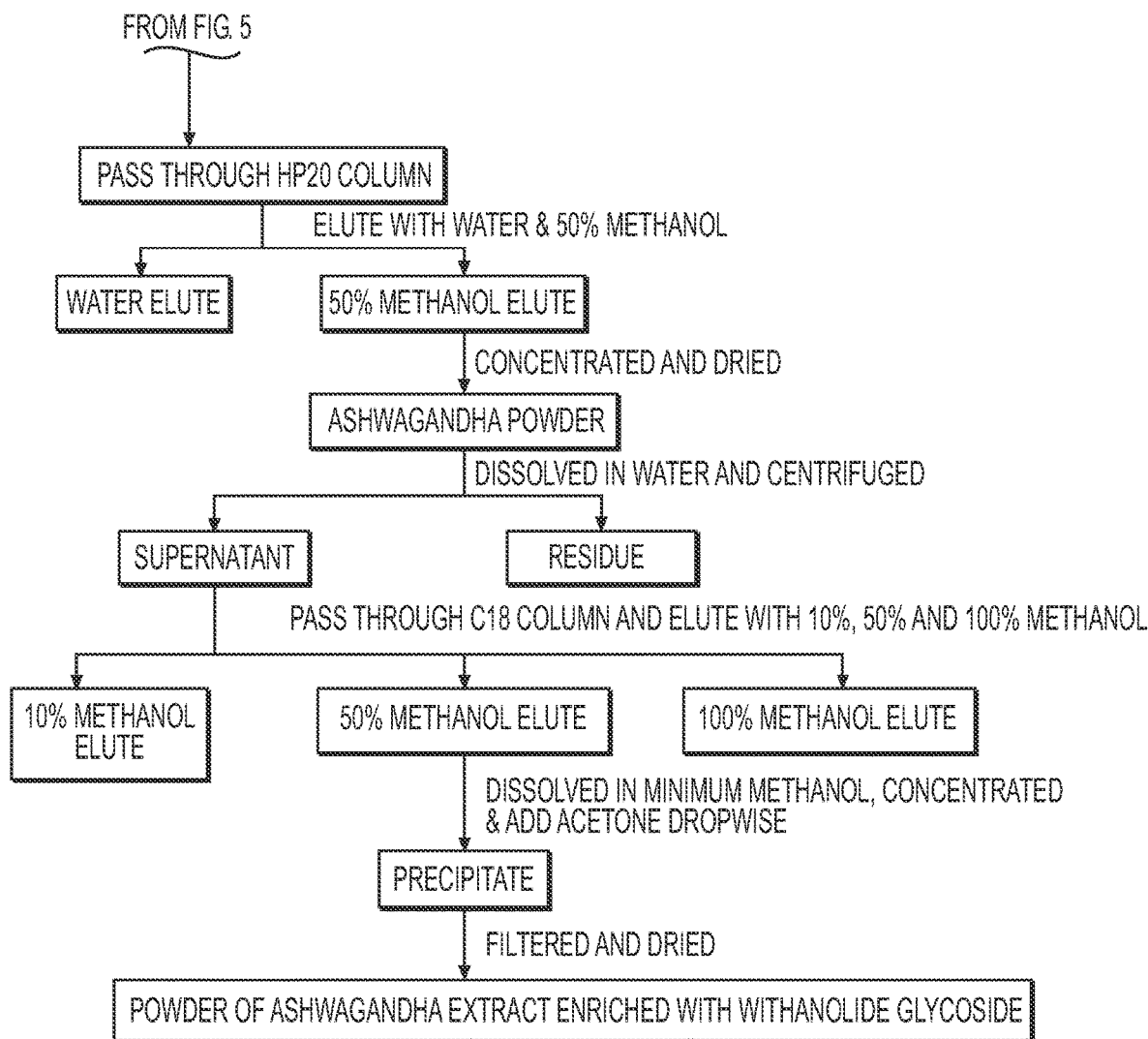

FIG. 5 describes a method of preparation of purified 60% methanol extract of Ashwagandha root extract after ammonia treatment and MDC extraction. Fresh root of Ashwagandha is treated with 2% ammonia solution in ratio of 1:2 (2% ammonia:root) for 4 hrs. The ammonia treated Ashwagandha root is extracted with methylene dichloride (dichloro methane) at a temperature of 70-80° C. in a Soxhlet extractor for 10 hrs to form residue and filtrate. The filtrate and residue is separated. The residue (Ashwagandha root) is washed with water till the pH become neutral. Then dried the residue (Ashwagandha root) in vacuum oven at 90-100° C. After drying the residue (root of Ashwagandha) is powdered to form a powder of root of Ashwagandha. (Sample 1)

Powder of roots of Ashwagandha (sample 1) is extracted with 60% methanol for one hour. The residue and supernatants obtained are separated. Supernatant is concentrated in an Agitated thin film evaporator (ATFE) to form a concentrated methanol extract. The concentrated methanol extract is dried under vacuum at above 500 mm of mercury to get powder of 60% methanol extract of Ashwagandha. (Sample 2)

Sample 2 is dissolved in water and clarify. The supernatant obtained after clarification is loaded on a HP20 resin column. Column is initially eluted with water followed by 50% methanol. 50% methanol fraction is collected and concentrated in an Agitated thin film evaporator (ATFE) to form concentrated methanol extract. Concentrate methanol fraction is fed into vacuum stripper and dried under vacuum at above 500 mm of mercury to get powder of 50% methanol extract (sample 3) of Ashwagandha.

Sample 3 is dissolved in water and centrifuged at 10,000 rpm for 10 minutes to form supernatant and residue. Supernatant is loaded on the C18 column. After passing the supernatant through the pre conditioned column, column is eluted with 10% methanol, 50% methanol and 100% methanol. All the methanol parts were collected. Each collected part is separately concentrated in an Agitated thin film evaporator (ATFE) to form concentrated extract of each part. Concentrate of each part is fed into vacuum stripper and dried separately under vacuum at above 500 mm of mercury to form powder of purified 10% methanol elute, 50% methanol elute (sample 4) and 100% methanol elute of Ashwagandha root.

Sample 4 is dissolved in minimum amount of methanol. The dissolved sample 4 in methanol was concentrated in an Agitated thin film evaporator (ATFE) to form a concentrated methanol extract of sample 4. Acetone is added dropwise to the concentrated methanol extract of sample 4 until the precipitation is complete. Then, the precipitate is filtered and dried under vacuum at above 500 mm of mercury to get powder of Ashwagandha extract (Sample 5).

In some embodiments, chloroform extract of Ashwagandha is provided. Another embodiments provides 100% methanol extract, 80% methanol extract and chloroform-methanol extract of Ashwagandha.

In another embodiment, root of Ashwagandha is extracted with 100% methanol for one hour. The root and methanol part (supernatant) obtained are separated. Supernatant is concentrated in an Agitated thin film evaporator (ATFE) to form a concentrated methanol extract. The concentrated methanol extract is dried under vacuum at above 500 mm of mercury to get powder of 100% methanol extract of Ashwagandha.

Figure 7:
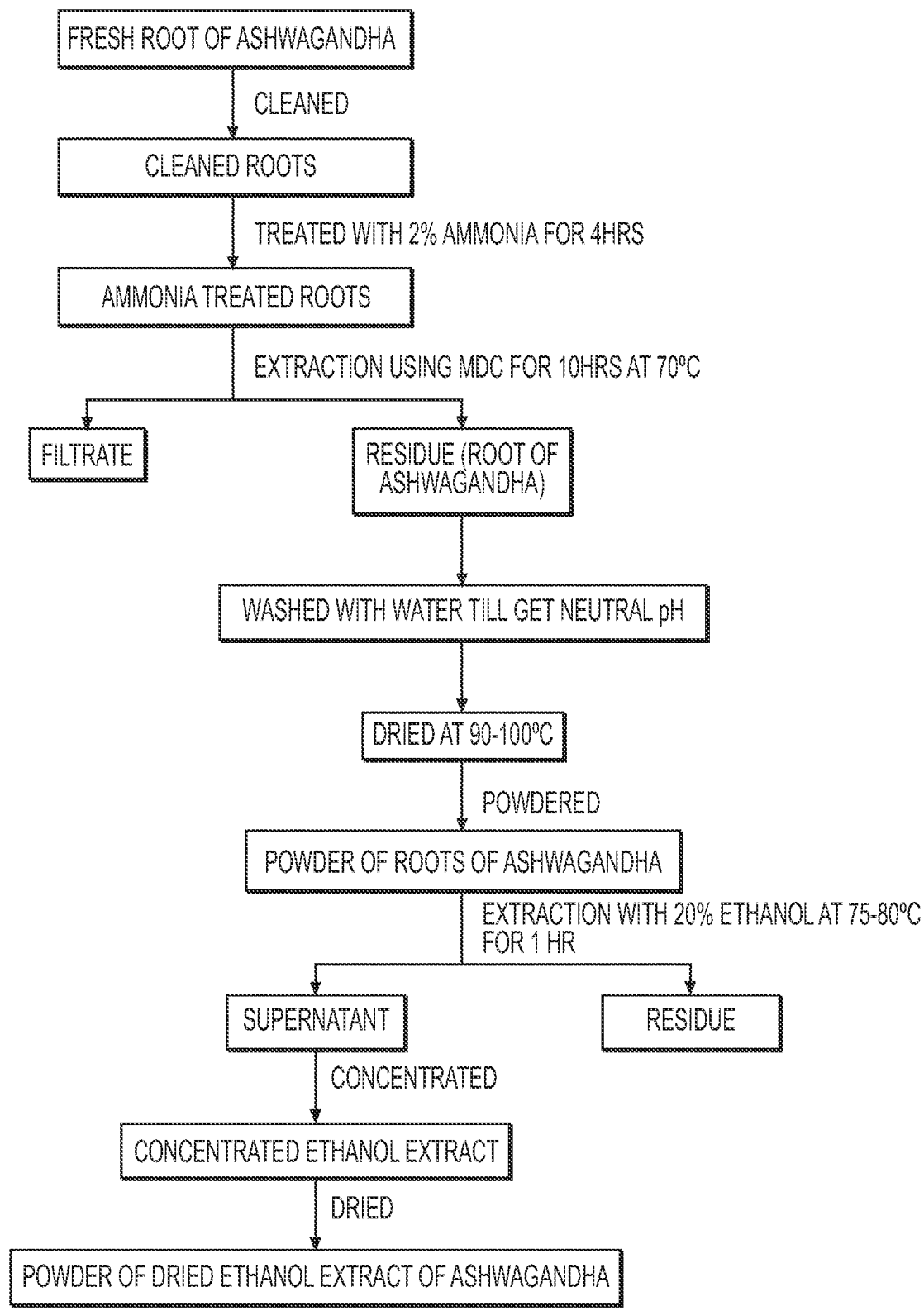
FIG. 7 provides a method of preparation of 20% ethanol extract of ammonia treated Ashwagandha root.

FIG. 7 describes a method of preparation of 20% ethanol extract of Ashwagandha root extract after ammonia treatment and MDC extraction. Fresh root of Ashwagandha is treated with 2% ammonia solution in ratio of 1:2 (2% ammonia:root) for 4 hrs. The ammonia treated Ashwagandha root is extracted with methylene dichloride (dichloro methane) at a temperature of 70-80° C. in a Soxhlet extractor for 10 hrs to form residue and filtrate. The filtrate and residue is separated. The residue is washed with water till the pH become neutral. Then dried the residue in vacuum oven at 90-100° C. After drying the residue (root of Ashwagandha) is powdered to form a powder of root of Ashwagandha.

Powder of root of Ashwagandha is extracted with 20% ethanol for one hour. The ethanol part (supernatant) obtained is concentrated in an Agitated thin film evaporator (ATFE) to form a concentrated ethanol extract. The concentrated methanol extract is filtered to form a filtrate. 35% maltodextrin is added to the filtrate and spray dried to get powder of 20% ethanol extract of Ashwagandha.

In one embodiment fresh roots of Ashwagandha are cleaned. Cleaned roots are dried and pulverized to get powder of root Ashwagandha.

Figure 8:
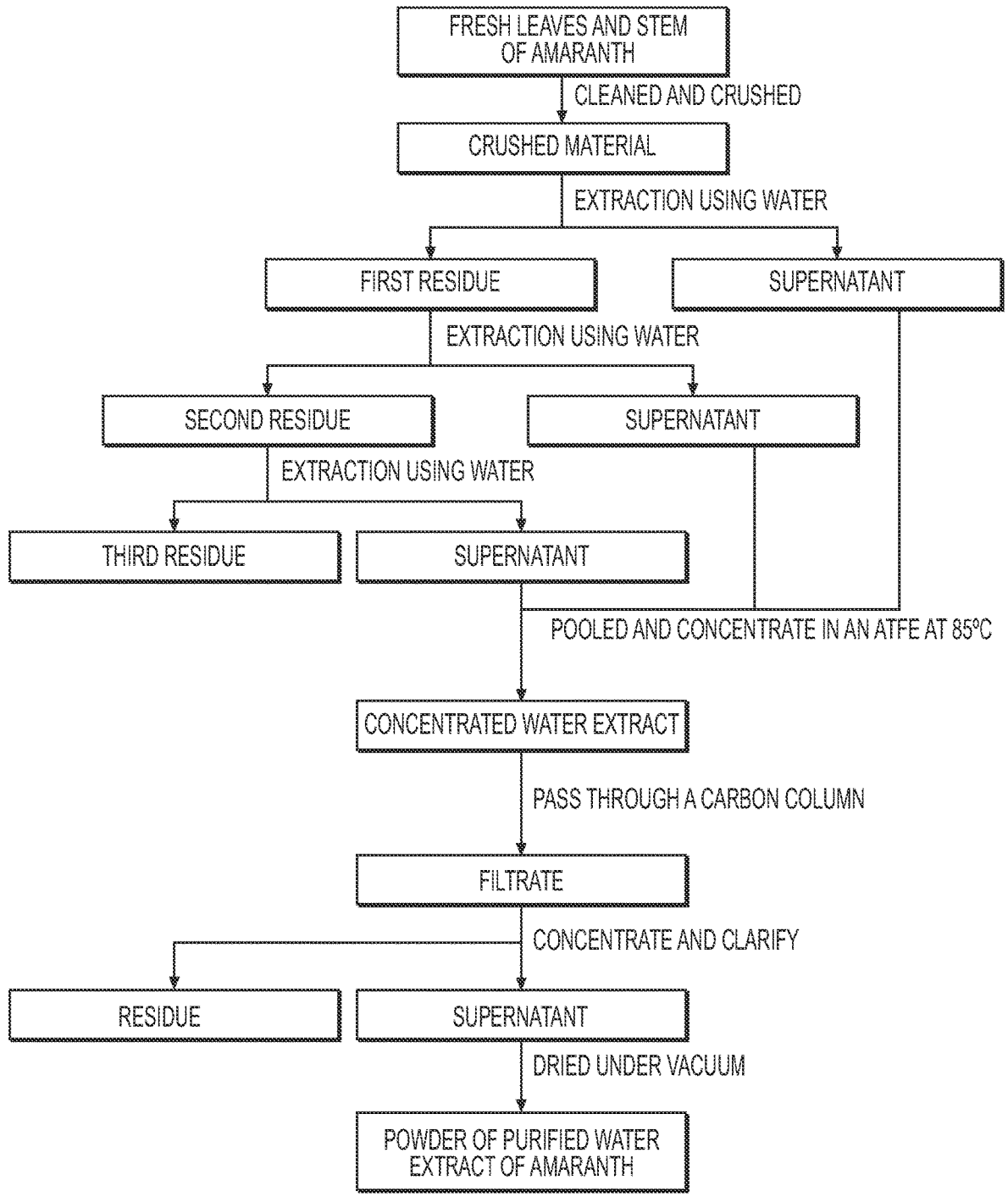
FIG. 8 provides a method of preparation of purified water extract of Amaranth.

FIG. 8 describes a method of preparation of purified Amaranth extract. Fresh leaves and stem of Amaranth is cleaned, crushed and extracted for about 1 hr using water in an extractor with reflux condenser to obtain residue and supernatant. The residue and supernatant is separated by draining out the supernatant from the extractor bottom through the filter cloth. The resultant supernatant is concentrated in an Agitated thin film evaporator (ATFE) at a temperature of 85° C. to form concentrated extract. Concentrated water extract is passed through a carbon column to obtain a filtrate. Filtrate is concentrated and clarified to form a supernatant and residue. Supernatant is dried under vacuum at above 500 mm of mercury to get powder of purified water extract of fresh Amaranth.

Figure 9:
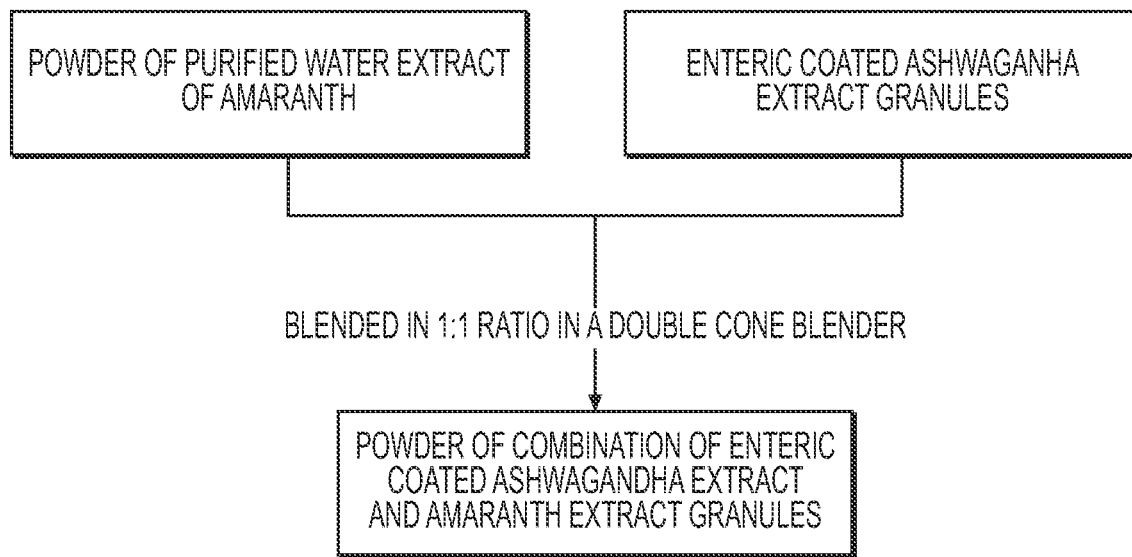
FIG. 9 provides a method of preparation of combination of enteric coated Ashwagandha extract and purified Amaranth extract.

FIG. 9 describes a method of preparation of combination of Enteric coated Ashwagandha extract and Amaranth extract. Enteric coated Ashwagandha extract and Amaranth extract is blended in 1:1 ratio by using Double Cone Blender.

In another embodiment Ashwagandha extract or powder in different pH is prepared by adding Ashwagandha powder/extract to different buffer (pH 1, 2, 3, 5, 7 and 7.4) in 1:20 ratio of Ashwagandha powder/extract:buffer. The extract-buffer solution is kept in a water bath at 37° C. for 2 hrs. The solution is neutralised by adding base or acid solution. The neutralised solution is concentrated and dried.

Details of some of the trials/experiments carried out and findings are explained below by way of examples.

Example 1

Fresh roots of Ashwagandha were collected (100 Kg). Roots of Ashwagandha were cleaned. Cleaned roots were treated with 2% ammonia solution in a ratio of 1:2 solvent: roots of Ashwagandha for 4 hrs. Ammonia treated Ashwagandha roots were filled in the Soxhlet extractor and extracted with dichloromethane or methylene dichloride (MDC) (300 L). The extraction was carried out for 10 hrs at a temperature of about 70° C. After the completion of extraction, the supernatant and residue were separated by filtration. Residue (roots of Ashwagandha) after MDC extraction was washed with water till the pH become neutral. Then dried the root in a vacuum oven at 90-100° C. After drying the roots of Ashwagandha was powdered to form a powder of roots of Ashwagandha (sample 1) (Yield 88%).

The supernatant was concentrated in an Agitated thin film evaporator (ATFE) at a temperature of 70° C. to form concentrated MDC extract. Concentrated MDC extract was dried under vacuum at above 500 mm of mercury to get powder of MDC extract of Ashwagandha after ammonia treatment (sample 2) (Yield 0.6%).

See also extract preparation in FIG. 1.

The alkaloid content in powder of root of Ashwagandha after ammonia treatment (sample 1) was found to be 0.6% by gravimetry method. The withanolide content in powder of root of Ashwagandha after ammonia treatment (sample 1) was about 0.7% by HPLC method. The withanolide glycoside content in powder of root of Ashwagandha after ammonia treatment (sample 1) was about 4% by HPLC method. Saponin content in powder of root of Ashwagandha after ammonia treatment (sample 1) was about 1% by UV method. The alkaloid content in powder of MDC extract of ammonia treated Ashwagandha root (sample 2) was about 60% by gravimetry method.

Example 2

Fresh roots of Ashwagandha were collected (100 Kg). Roots of Ashwagandha were cleaned. Cleaned roots were treated with 2% ammonia solution in a ratio of 1:2 solvent: roots of Ashwagandha for 4 hrs. Ammonia treated Ashwagandha roots were filled in the Soxhlet extractor and extracted with dichloromethane or methylene dichloride (MDC) (300 L). The extraction was carried out for 10 hrs at a temperature of about 70° C. After the completion of extraction, the supernatant and residue were separated by filtration. Residue (roots of Ashwagandha) after MDC extraction was washed with water till the pH become neutral. Then dried the root in a vacuum oven at 90-100° C. After drying the roots of Ashwagandha was powdered to form a powder of roots of Ashwagandha (sample 1) (88%).

88 Kg of powder of roots of Ashwagandha (sample 1) was extracted with 60% methanol. Sample 1 was refluxed with 60% methanol (300 L) at the boiling temperature (60-70° C.) of methanol for one hour to obtain a second residue and second supernatant. The second residue was then further extracted two more times with three times the quantity of methanol at each time. The residue and supernatants were separated. All the supernatants were pooled and concentrated in an Agitated thin film evaporator (ATFE) to form a concentrated methanol extract. The concentrated methanol extract was dried under vacuum at above 500 mm of mercury to get powder of 60% methanol extract of Ashwagandha. The yield was about 10% (Sample 2).

See also extract preparation in FIG. 2.

The withanolide glycoside content in powder of ammonia treated 60% methanol extract of Ashwagandha was about 6% by HPLC. Saponin content in powder of ammonia treated 60% methanol extract of Ashwagandha was about 1.5% by UV method. Alkaloid content in powder of ammonia treated 60% methanol extract of Ashwagandha was about 0.1% by gravimetry method. Withanolide aglycones content in powder of ammonia treated 60% methanol extract of Ashwagandha was about 0.2% by HPLC. Oligosaccharide content in in powder of ammonia treated 60% Methanol extract of Ashwagandha was about 5% by HPLC.

Example 3

Roots of Ashwagandha were collected (100 Kg). Roots of Ashwagandha were cleaned. Cleaned roots were extracted with 50% methanol. Roots were refluxed with 50% methanol at the boiling temperature (60-70° C.) of methanol for one hour to obtain a first residue and first supernatant. The first residue was then further extracted two more times with four times the quantity of methanol at each time. The residue and supernatants were separated. All the supernatants were pooled and concentrated in an Agitated thin film evaporator (ATFE) to form a concentrated methanol extract. The concentrated methanol extract was dried under vacuum at above 500 mm of mercury to get powder of 50% methanol extract of Ashwagandha. (yield 22%) (Sample 1).

Powder of 50% methanol extract of Ashwagandha was dissolved in minimum amount of methanol. The dissolved methanol part was concentrated in an Agitated thin film evaporator (ATFE) to form a concentrated methanol extract. Acetone was added dropwise to the concentrated methanol extract until the precipitation was complete. Then, the precipitate was filtered and dried under vacuum at above 500 mm of mercury to get powder of Ashwagandha extract (yield of about 3%) (Sample 2).

See also extract preparation in FIG. 3.

Withanolide glycoside content in powder of 50% methanol extract of Ashwagandha (Sample 2) was 20% by HPLC. Saponin content in powder of 50% methanol extract of Ashwagandha (Sample 2) was 3.5% by UV method. Alkaloid content in powder of 50% methanol extract of Ashwagandha (Sample 2) was 1.2% by gravimetry method. Withanolide aglycones content in powder of 50% methanol extract of Ashwagandha (Sample 2) was about 1% by HPLC method.

Example 4

Roots of Ashwagandha were collected (100 Kg). Roots of Ashwagandha were cleaned. Cleaned roots were treated with 2% ammonia solution in a ratio of 1:2 solvent:roots of Ashwagandha for 4 hrs. Ammonia treated Ashwagandha roots were filled in the Soxhlet extractor and extracted with dichloromethane or methylene dichloride (MDC) (300 L). The extraction was carried out for 10 hrs at a temperature of about 70° C. After the completion of extraction, the first supernatant and first residue (roots of Ashwagandha) formed was separated by filtration. First residue (roots of Ashwagandha after MDC extraction) was washed with water till the pH become neutral. Then dried the first residue (root of Ashwagandha) in a vacuum oven at 90-100° C. After drying the first residue (roots of Ashwagandha) was powdered to form a powder of roots of Ashwagandha (Yield 88%) after ammonia treatment (sample 1).

88 Kg of powder of roots of Ashwagandha (sample 1) was extracted with 60% methanol. Sample 1 was refluxed with 60% methanol (300 L) at the boiling temperature (60-70° C.) of methanol for one hour to obtain a second residue and second supernatant. The second residue was then further extracted two more times with three times the quantity of methanol at each time. The residue and supernatants were separated. All the supernatants were pooled and concentrated in an Agitated thin film evaporator (ATFE) to form a concentrated methanol extract. The concentrated methanol extract was dried under vacuum at above 500 mm of mercury to get powder of 60% methanol extract of Ashwagandha. (yield 10%) (Sample 2).

10 Kg of sample 2 was dissolved in water and clarified to form supernatant and residue. Supernatant was loaded on a HP20 resin column. After passing the supernatant through the column, column was initially eluted with water followed by 50% methanol. 50% methanol elute was collected. 50% methanol fraction was concentrated in an Agitated thin film evaporator (ATFE) to form concentrated methanol extract. Concentrate fraction was fed into vacuum stripper and dried under vacuum at above 500 mm of mercury to get powder of 50% methanol extract (sample 3)(yield 8%) of Ashwagandha. The powder of 50% methanol fraction of Ashwagandha contain withanolide glycosides (35%).

See also extract preparation in FIG. 4.

The withanolide glycoside content in powder of 50% methanol elute of Ashwagandha after column treatment (sample 3) was found to be 35% by HPLC. Saponin content in powder of 50% methanol elute of Ashwagandha after column treatment (sample 3) was 10% by UV method. The alkaloid content in powder of 50% methanol elute of Ashwagandha after column treatment (sample 3) was found to be 0.04% by gravimetry method. The withanolide aglycone content in powder of 50% methanol elute of Ashwagandha after column treatment (sample 3) was not detectable by HPLC. Oligosaccharides in powder of 50% methanol elute of Ashwagandha after column treatment (sample 3) were not detectable.

Example 5

Roots of Ashwagandha were collected (100 Kg). Roots of Ashwagandha were cleaned. Cleaned roots were treated with 2% ammonia solution in a ratio of 1:2 solvent:roots of Ashwagandha for 4 hrs. Ammonia treated Ashwagandha roots were filled in the Soxhlet extractor and extracted with dichloromethane or methylene dichloride (MDC) (300 L). The extraction was carried out for 10 hrs at a temperature of about 70° C. After the completion of extraction, the first supernatant and first residue was separated by filtration. First residue (roots of Ashwagandha after MDC extraction) was washed with water till the pH become neutral. Then dried the first residue (roots of Ashwagandha) in a vacuum oven at 90-100° C. After drying the first residue (roots of Ashwagandha) was powdered to form a powder of roots of Ashwagandha (Yield 88%) after ammonia treatment (sample 1).

88 Kg of powder of roots of Ashwagandha (sample 1) was extracted with 60% methanol. Sample 1 was refluxed with 60% methanol (300 L) at the boiling temperature (60-70° C.) of methanol for one hour to obtain a second residue and second supernatant. The second residue was then further extracted two more times with three times the quantity of methanol at each time. The residue and supernatants were separated. All the supernatants were pooled and concentrated in an Agitated thin film evaporator (ATFE) to form a concentrated methanol extract. The concentrated methanol extract was dried under vacuum at above 500 mm of mercury to get powder of 60% methanol extract of Ashwagandha. (yield 10%) (Sample 2).

10 Kg of sample 2 was dissolved in water and clarified to form supernatant and residue. Supernatant was loaded on a HP20 resin column. After passing the supernatant through the column, column was initially eluted with water followed by 50% methanol. 50% methanol elute was collected. 50% methanol fraction was concentrated in an Agitated thin film evaporator (ATFE) to form concentrated methanol extract. Concentrate fraction was fed into vacuum stripper and dried under vacuum at above 500 mm of mercury to get powder of 50% methanol extract (sample 3)(yield 8%) of Ashwagandha. The powder of 50% methanol fraction of Ashwagandha contain withanolide glycosides (35%).

Powder of 50% methanol fraction (sample 3) was dissolved in water and centrifuged at 10,000 rpm for 10 minutes to form supernatant and residue. Supernatant was loaded on the C18 column. Before passing through column, the column was conditioned with 10% methanol. After passing the supernatant through the pre conditioned column, column was eluted with 10% methanol, 50% methanol and 100% methanol. All the methanol parts were collected. Each collected part was separately concentrated in an Agitated thin film evaporator (ATFE) to form concentrated extract of each part. Concentrate of each part was fed into vacuum stripper and dried separately under vacuum at above 500 mm of mercury to form powder of purified 10% methanol elute (Yield 7%), 50% methanol elute (Yield 3.5%) (sample 4) and 100% methanol elute (Yield 1.5%) of Ashwagandha root.

The powder of 50% methanol fraction of Ashwagandha contain withanolide glycosides (50%), Alkaloids (0.01%) and withanolide aglycones (0.03%).

Powder of 50% methanol elute of root of Ashwagandha (sample 4) was dissolved in minimum amount of methanol. The dissolved sample 4 in methanol was concentrated in an Agitated thin film evaporator (ATFE) to form a concentrated methanol extract of sample 4. Acetone was added dropwise to the concentrated methanol extract of sample 4 until the precipitation was complete. Then, the precipitate was filtered and dried under vacuum at above 500 mm of mercury to get powder of Ashwagandha extract (Sample 5) (yield 1.8%).

See also extract preparation in FIG. 5.

The withanolide glycoside content in powder of column purified Ashwagandha extract (sample 5) was found to be 80% by HPLC. Saponin content in powder of column purified Ashwagandha extract (sample 5) was found to be 15% by UV method. The alkaloid content in powder of column purified Ashwagandha extract (sample 5) was found to be 0.001% by gravimetry method. The withanolide aglycone content in powder of column purified Ashwagandha extract (sample 5) was not detected by HPLC. Oligosaccharide content in powder of column purified Ashwagandha extract (sample 5) was not detected.

HPLC and LCMS Analysis of Withanolide Glycosides and Withanolide Aglycones

Extract of Ashwagandha (sample 5) was analysed by HPLC and found to contain withanolide glycosides (withanoside I to VII), sitoindosides (sitoindosides I to X) and withanamides and the presence was confirmed by LCMS analysis.

HPLC analysis of extract of Ashwagandha detects withanoside I to VII (withanolide glycosides), sitoindosides I to X and withanamides and negligible amount of withanolide aglycones (withaferin A, 12-deoxywithastramonolide, withanolide A) at 227 nm.

The extract of Ashwagandha was subjected to liquid chromatography-mass spectrometry (LCMS) analysis and the presence of active components like withanoside I to VII, sitoindosides I to X and withanamides were confirmed by LCMS data obtained. From LCMS data we can also confirmed the presence of negligible amount of inactive components like withanolide aglycones in the Ashwagandha extract.

Acid Hydrolysis

Ashwagandha extract (sample 5) was subjected to acid hydrolysis. 2.5 Kg of Sample 5 was dissolved in 1N hydrochloric acid by continuous stirring up to 4 hours. Then transferred the mixture in to a separating funnel and extracted with chloroform. The two layers were separated. Acid layer was removed and chloroform layer was collected. The chloroform layer was again washed with water in a separating funnel until pH become neutral. The chloroform layer was collected and filtered through a filter paper containing sodium sulphate. Filtered chloroform layer was concentrated and dried under vacuum at above 500 mm of mercury to get powder of Ashwagandha extract (sample 6) (yield 1.5%).

The extract after hydrolysis was analysed by HPLC. From the HPLC chromatogram at 227 nm the major peak obtained represents the inactive aglycone part. Only a small percentage of active glycosidic part was present. After hydrolysis of extract of Ashwagandha, the withanolide glycosides present in the extract was converted to aglycones and it was confirmed by LCMS. The extract of Ashwagandha after hydrolysis was subjected to liquid chromatography-mass spectrometry (LCMS) analysis and the presence of inactive components like withaferin A, 12-deoxywithastramonolide, withanolide A (molecular mass 471.54, 471, 471.64 respectively) were confirmed by LCMS. So it was again confirmed the presence of withanolide glycosides, sitoindosides and withanamides in the extract which was converted into aglycone part after hydrolysis.

Example 6

Roots of Ashwagandha were collected (100 Kg). Roots of Ashwagandha were cleaned. Cleaned roots were extracted with 60% methanol. Roots were refluxed with 60% methanol at the boiling temperature (60-70° C.) of methanol for one hour to obtain a first residue and first supernatant. The first residue was then further extracted two more times with four times the quantity of methanol at each time. The residue and supernatants were separated. All the supernatants were pooled and concentrated in an Agitated thin film evaporator (ATFE) to form a concentrated methanol extract. The concentrated methanol extract was dried under vacuum at above 500 mm of mercury to get powder of 60% methanol extract of Ashwagandha. (Sample 1) (yield 18%).

18 Kg of sample 1 was refluxed with chloroform at the boiling temperature (70-80° C.) of chloroform for half an hour to obtain second residue and second supernatant. The second residue was then further extracted two more times with four times the quantity of chloroform at each time. The residue and supernatants were separated. The residue was dried under vacuum at above 500 mm of mercury to get powder of chloroform extract of methanol extract of Ashwagandha (Sample 2) (Yield 16%).

See also extract preparation in FIG. 6.

The withanolide content in powder of chloroform extract of 60% methanol extract of Ashwagandha (sample 2) was found to be 0.7% by HPLC method. Alkaloid content in powder of chloroform extract of 60% methanol extract of Ashwagandha (sample 2) was found to be 1.5% by gravimetry method. Withanolide glycoside content in powder of chloroform extract of 60% methanol extract of Ashwagandha (sample 2) was found to be 5% by HPLC method. Saponin content in powder of chloroform extract of 60% methanol extract of Ashwagandha (sample 2) was found to be 1.6% by UV method. Oligosaccharide content in in powder of chloroform extract of 60% methanol extract of Ashwagandha (sample 2) was found to be 20% by HPLC method.

Example 7

Analysis of Oligosaccharides, Withanolide Glycosides and Aglycones in Different Ashwagandha Extracts Different extracts of Ashwagandha were analysed for the presence of oligosaccharides, withanolide glycosides and aglycones.

Extracts of Ashwagandha analysed were 1. 60% methanol extract of Ashwagandha root prepared as per Example 6;
2. Powder of ammonia treated 60% methanol extract of Ashwagandha prepared as per example 2;
3. Powder of 50% methanol fraction of Ashwagandha after passing through HP20 resin column prepared as per example 4;
4. Powder of column purified Ashwagandha extract prepared as per example 5.

HPTLC Analysis of Oligosaccharides and Withanolide Glycosides and Aglycones

All the above extracts were analysed by HPTLC for the presence of actives in the corresponding extract.

HPTLC was performed on precoated TLC plates. Standard solution of glycowithanolides (Sitoindosides IV and V), withanolide aglycones (withaferin A, 12-deoxywithastramonolide, withanolide A) and oligosaccharides (Sucrose and maltose) along with extracts of Ashwagandha roots were applied. The plates were developed using n-butanol-acetic acid-water 4:1:2 (v/v/v) as mobile phase. Densitometric evaluation of the plates was performed at $\lambda=225$ nm.

After the analysis of different Ashwagandha extracts, Powder of 50% methanol fraction of Ashwagandha after passing through HP20 resin column prepared as per example 4 and Powder of column purified Ashwagandha extract prepared as per example 5 showed the presence of withanolide glycosides ($R_f$ 0.43-0.78). But there is no spot observed for the presence of withanolide aglycones and oligosaccharides. But in powder of ammonia treated 60% Methanol extract of Ashwagandha prepared as per example 2, the HPTLC pattern showed the presence of oligosaccharides ($R_f$ 0.24-0.38). In the HPTLC pattern of 60% methanol extract of Ashwagandha extract, the intensity of spot between $R_f$ 0.24-0.38 corresponds to oligosaccharides and other two spots corresponds to withanolide glycosides ($R_f$ 0.43-0.78) and withanolide aglycones ($R_f$ 0.82-0.94).

HPLC Analysis of Oligosaccharides and Withanolide Glycosides and Aglycones

Oligosaccharides were determined using Waters HPLC system with a RI detector and Empower software with a carbohydrate analysis column [Waters] 300×3.9 mm; acetonitrile:water—80:20 (v/v) was used as the mobile phase; the run time was 10 minutes and flow rate was 2 ml/min in an isocratic mode.

The withanolide glycosides/withanolide aglycones were analyzed by high performance liquid chromatography (HPLC) on a RP C18 column (250×4.6 mm Shimadzu Co., Japan.) using 0.01M anhydrous potassium dihydrogen orthophosphate and Acetonitrile as the mobile phase and UV detection at 227 nm. The eluent flow rate was 1 ml/min.

HPLC analysis of 60% methanol extract of Ashwagandha root showed about 5% withanolide glycosides, 0.7% withanolide aglycones and 20% oligosaccharides. Powder of ammonia treated 60% methanol extract of Ashwagandha contained about 6% withanolide glycosides, about 0.2% withanolide aglycones and about 5% oligosaccharides. The weight ratio of withanolide glycosides to withanolide aglycones was 30:1 and weight ratio of withanolide glycosides to oligosaccharide was 6:5. Oligosaccharides were not detected in the enriched extracts of Ashwagandha prepared as per Example 4 (about 35% withanolide glycosides). Oligosaccharides were not detected in the enriched extracts of Ashwagandha prepared as per Example 5 (about 80% withanolide glycosides).

Example 8

Method of Making Enteric Coated Extract

Specific quantity of purified Ashwagandha root extract/other Ashwagandha root extracts were loaded into the bowl of the fluid bed extractor (pam glatt pharma technologies). The bowl has a fine Stainless steel mesh at the bottom. The air used for drying/fluidizing was successively filtered through HEPA (High-efficiency particulate arrestance) filters (EU 13 grade, 0.3 micron rating, 99.997% efficiency).

Hot, filtered air up to 90° C. was passed at high velocity from the bottom of the FBE bowl through the feed material (Purified Ashwagandha root extract/Ashwagandha root extract) and feed material was fluidised.

Meantime, enteric/nonenteric coating material was dissolved in specific quantity of solvents depends on the nature of enteric/nonenteric coating material. Enteric/nonenteric coating solution was sprayed into fluidised material by using a spraying devise attached to the FBE (spray speed 2 L in 1 Hr, pump rpm range 10-12). Through the process of fluid bed coating, fluidized particles are continuously sprayed with coating solution, depositing layers (films) of material to the surface of the particles, and yielding an even layer with particular thickness.

Example 9

The tablets were prepared on an automated 16 station tablet punch machine. The tablets were coated by Pan coating method. In brief, 5 Kg tablets were introduced into the Pan and rotated at 20 rpm. Coating material was sprayed on to the tablets via a spray gun as 30% aqueous dispersion. Simultaneously hot blower (110 degree) was started for fast drying of the tablets. Tablets were coated till a weight gain of 5-6%. After coating, tablets were further kept in hot air stream for 15 minutes to ensure complete drying.

Example 10

Method of Analysis of Withanolide Glycoside and Withanolide Aglycones 125 mg of Ashwagandha extract was accurately weighed and transferred into a 25 ml standard flask and made up to a 25 ml solution with methanol. Filtered through 0.2 μm membrane filter before injection. Standard was prepared by weighing accurately 5 mg standard [standards from Chromadex] and transferred into a 5 ml standard flask and made up to a 5 ml solution with methanol. From this pipette out 200 μl into 10 ml standard flask (20 ppm) and made up to a 10 ml solution with methanol. Filter through 0.2 μm membrane filter before injection.

The withanolide glycosides/withanolide aglycones were analyzed by high performance liquid chromatography (HPLC) on a RP C18 column (250×4.6 mm Shimadzu Co., Japan.) using 0.01M anhydrous potassium dihydrogen orthophosphate (pH was adjusted to 2.58 using 10% orthophosphoric acid solution) and acetonitrile as the mobile phase and UV detection at 227 nm. The eluent flow rate was 1 ml/min.

By comparing the area of standard and sample, the percentage of withanolide glycosides/withanolide aglycones were calculated using the formula $$\% \text{ of withanolide glycosides/withanolide aglycones} = \frac{\text{Area of sample} \times \text{amount of } std \times \text{Purity of } std}{\text{Area of } Std \times \text{weight of the sample}}$$

Example 11

Method of Analysis of Alkaloids 3 g of dried extract of Ashwagandha (W1) was poured into the conical flask. 5 ml ammonia was added to the extract in conical flask and shaken for 15 minutes. Then mixture of 75 ml of ether and 25 ml of alcohol was added to the flask. This solution was shaken continuously for 1 hour. The solution was filtered in the separator through filter paper. The residue was washed from conical flask with mixture of 75 ml of ether and 25 ml of alcohol. The total solution was extracted with 25 ml dilute sulphuric acid in a separating funnel. The two layers were separated. Ether layer was removed and acid aqueous layer was collected. Acid aqueous layer was washed with 25 ml of methylene dichloride (MDC) in a separating funnel. Two layers were separated and acid aqueous layer was collected and adjusted to alkaline media with ammonia. This aqueous solution was extracted with 25 ml chloroform in a separating funnel. Two layers formed were separated. Chloroform layer was collected and 25 ml chloroform was again added to aqueous layer. This process was repeated two more times and all the chloroform layers were collected. Chloroform part was washed with water in a separating funnel. After separation of two layers, chloroform layer was collected and filtered into a weighed beaker (W2). Evaporated to dryness and then weighed the beaker with dried sample (W3).

Calculation $$\% \text{ of alkaloid} = \frac{(W3 - W2) \times 100}{W1}$$

(See, Anonymous. (1996). Indian Pharmacopoeia, Vol. II, Government of India, Ministry of Health and Family Welfare, New Delhi, A-81-83, 95, 736.)

Example 12

Dissolution Study

The release pattern of study drug was tested in simulated gastric fluid (pH 1.2) and simulated intestinal fluid from (pH 6.8) by in vitro USP dissolution apparatus (LABINDIA DS 8000). The dissolution medium (simulated gastric fluid without enzyme, pH 1.2), free from dissolved air, was filled into the vessel of the dissolution apparatus. Apparatus was assembled and dissolution medium was heated to 36.5° to 37.5°. The enteric coated tablet containing alkaloid free purified Ashwagandha root extract was sunk to the bottom of one vessel prior to the rotation of the paddle. In another vessel tablet of alkaloid free purified Ashwagandha root extract without enteric coating was sunk to the bottom of vessel prior to the rotation of the paddle. A suitable device such as a wire of glass helix was used to keep horizontal at the bottom of the vessel tablets that would otherwise float.

After two hours of operation, an aliquot of the liquid was collected from two vessels and the dissolution medium was changed to simulated intestinal fluid with pH 6.8 and repeated the above process. Samples were collected at 3, 4 and 5 hours.

The samples from two vessels at each time point were transferred into a liquid-liquid extractor and extracted with chloroform-methanol mixture (80:20). Acidic and chloroform-methanol phases were separated. Chloroform-methanol phase was collected and acidic phase was again extracted with chloroform-methanol two more times. All the chloroform-methanol phases were pooled and extracted with water. Aqueous and chloroform-methanol phases were separated and chloroform-methanol phase was collected. chloroform-methanol phase was concentrated and dried to form powder of chloroform-methanol extract.

chloroform-methanol extract is dissolved in methanol and analysed by HPLC.

| | Percentage of withanolide glycosides | |
|---|---|---|
| Time (Hrs ) | Enteric coated tablet of alkaloid free purified Ashwagandha root extract | Tablet of purified Ashwagandha root extract without enteric coating |
| 0 | 0 | 0 |
| 2 | 20 | 75 |
| 3 | 40 | 10 |
| 4 | 30 | 5 |
| 5 | 25 | 2 |

It was found that in first 2 hours only 20 percent of the drug was released following the administration of enteric coated tablet of alkaloid free purified Ashwagandha root extract. But after 2 hours 40 percent of the drug was released and results at 4 and 5 hours showed complete release of enteric coated tablet of alkaloid free purified Ashwagandha root extract.

Example 13

Efficacy Study of Different Ashwagandha Extracts.

44 rats were divided into eleven groups having 4 rats in each group. The animals were trained for swimming test (15 minutes) as pre-test session and then fasted overnight. To the fasted animals, reserpine (6 mg/kg) was injected i.p. to depress the animals. After 1 hour of reserpine injection, the test samples/standard was fed orally as designated dose. After 1 hour of test sample/standard, the rats were tested using forced swim test and duration of immobility in the 5 minutes test session was recorded.

TABLE 1

Segregation of rats for experimental study

| Groups | Treatment |
|---|---|
| Group I | Normal control (Received only vehicle; 1% Tween 80 v/v p.o.). |
| Group II | Reserpine (6 mg/kg i.p) + Vehicle (1% Tween 80 v/v p.o.). |
| Group III | Reserpine (6 mg/kg i.p) + Ashwagandha extract with minimum 5% withanolides (Dosage 100 mg/kg p.o). |
| Group IV | Reserpine (6 mg/kg i.p) + Ashwagandha extract with minimum 2.5% withanolides (Dosage 100 mg/kg p.o). |

TABLE 1-continued

Segregation of rats for experimental study

| Groups | Treatment |
|---|---|
| Group V | Reserpine (6 mg/kg i.p) + Ashwagandha extract with minimum 1.8% withanolides and minimum 2.5% alkaloids (Dosage 100 mg/kg p.o). |
| Group VI | Reserpine (6 mg/kg i.p) + Ashwagandha extract with minimum 1.1% withanolides (Dosage 100 mg/kg p.o). |
| GroupVII | Reserpine (6 mg/kg i.p) + Ashwagandha extract with minimum 0.7% withanolides (sample 2 prepared as per example 6) (Dosage 100 mg/kg p.o). |
| Group VIII | Reserpine (6 mg/kg i.p) + Ashwagandha extract with minimum 20% withanolide glycosides (sample 2 prepared as per example 3) (Dosage 100 mg/kg p.o). |
| Group IX | Reserpine (6 mg/kg i.p) + Purified Ashwagandha extract with 35% withanolide glycosides (sample 3 prepared as per example 4) (Dosage: 100 mg/kg p.o.). |
| Group X | Reserpine (6 mg/kg i.p) + Purified Ashwagandha extract with 80% withanolide glycosides (sample 5 prepared as per example 5) (Dosage: 100 mg/kg p.o.). |
| Group XI | Reserpine (6 mg/kg i.p) + Fluoxetine (10 mg/kg p.o.). |

TABLE 2

Effect of different Ashwagandha extracts on Immobility time in rats.

| Groups | Treatment | Immobility time in seconds |
|---|---|---|
| Group I | Normal control (Received only vehicle; 1% Tween 80 v/v p.o.). | 120 |
| Group II | Reserpine (6 mg/kg i.p) + Vehicle (1% Tween 80 v/v p.o.). | 210 |
| Group III | Reserpine (6 mg/kg i.p) + Ashwagandha extract with minimum 5% withanolides (Dosage 100 mg/kg p.o). | 200 |
| Group IV | Reserpine (6 mg/kg i.p) + Ashwagandha extract with minimum 2.5% withanolides (Dosage 100 mg/kg p.o). | 205 |
| Group V | Reserpine (6 mg/kg i.p) + Ashwagandha extract with minimum 1.8% withanolides and minimum 2.5% alkaloids (Dosage 100 mg/kg p.o). | 200 |
| Group VI | Reserpine (6 mg/kg i.p) + Ashwagandha extract with minimum 1.1% withanolides (Dosage 100 mg/kg p.o). | 195 |
| GroupVII | Reserpine (6 mg/kg i.p) + Ashwagandha extract with minimum 0.7% withanolides (Dosage 100 mg/kg p.o). | 190 |
| Group VIII | Reserpine (6 mg/kg i.p) + Ashwagandha extract with minimum 20% withanolide glycosides (Dosage 100 mg/kg p.o). | 180 |
| Group IX | Reserpine(6 mg/kgi. p) + Purified Ashwagandha extract with 35% withanolide glycosides (Dosage: 100 mg/kg p.o.). | 145 |
| Group X | Reserpine(6 mg/kgi. p) + Purified Ashwagandha extract with 80% withanolide glycosides (Dosage: 100 mg/kg p.o.). | 135 |
| Group XI | Reserpine(6 mg/kg i.p) + Fluoxetine (10 mg/kg p.o.). | 122 |

As shown in the Table 2, immobility time for normal control animals was 120 seconds. When reserpine was injected i.p., the animals got depressed and immobility time was increased to 210 seconds (Group II). Oral administration of Ashwagandha root extract with minimum 5% of withanolides (100 mg/kg) after reserpine injection was not much effective and immobility time was recorded as 200 seconds (Group III). Similarly, rats treated with Ashwagandha extract with minimum 2.5%, 1.8%, 1.1% and 0.7% of withanolides (100 mg/kg) were also not effective and immobility time was recorded near to 200 seconds (Group IV to Group VII). When animals were treated with Ashwagandha extract with 20%, 35% and 80% of withanolide glycosides (100 mg/kg), the immobility time was reduced significantly to 180, 145 and 135 seconds respectively (Group VIII to Group X). In case of fluoxetine standard at 10 mg/kg (Group XI), the immobility time was only 122 seconds which is almost similar to normal control animals.

Example 14

Effect of Different Enteric and Nonenteric Coated Ashwagandha Extracts on Immobility Time in Rats.

92 rats were divided into twenty three groups. Each group had 4 rats. The animals were trained for swimming test (15 minutes) as pre-test session and then fasted overnight. To the fasted animals, reserpine (6 mg/kg) was injected i.p. to depress the animals. After 1 hour of reserpine injection, the test samples/standard was fed orally as designated dose. After 1 hour of test sample/standard, the rats were tested using forced swim test and duration of immobility in the 5 minutes test session was recorded.

TABLE 1

Segregation of rats for experimental study.

| Groups | Treatment |
|---|---|
| Group I | Normal control (Received only vehicle; 1% Tween 80 v/v p.o.). |
| Group II | Reserpine (6 mg/kg i.p) + Vehicle (1% Tween 80 v/v p.o.). |
| Group III | Reserpine (6 mg/kg i.p) + Ashwagandha extract with minimum 6% withanolide glycosides (sample 2 prepared as per example 2) (Dosage 100 mg/kg p.o). |
| Group IV | Reserpine (6 mg/kg i.p) + Ashwagandha extract with minimum 6% withanolide glycosides (sample 2 prepared as per example 2) (Dosage 20 mg/kg p.o). |
| Group V | Reserpine (6 mg/kg i.p) + Ashwagandha extract with minimum 6% withanolide glycosides (sample 2 prepared as per example 2) coated with pectin (prepared as per example 8) (Dosage 20 mg/kg p.o). |
| Group VI | Reserpine (6 mg/kg i.p) + Ashwagandha extract with 6% minimum withanolide glycosides (sample 2 prepared as per example 2) coated with Eudragit (prepared as per example 8) (Dosage 20 mg/kg p.o). |
| Group VII | Reserpine (6 mg/kg i.p) + Ashwagandha extract with minimum 1% withanolide glycoside coated with Eudragit (Dosage 20 mg/kg p.o). |
| Group VIII | Reserpine (6 mg/kg i.p) + Ashwagandha extract with minimum 20% withanolide glycoside (sample 2 prepared as per example 3) (Dosage 100 mg/kg p.o). |
| Group IX | Reserpine (6 mg/kg i.p) + Ashwagandha extract with minimum 20% withanolide glycoside (sample 2 prepared as per example 3) (Dosage 20 mg/kg p.o). |
| Group X | Reserpine (6 mg/kg i.p) + Ashwagandha extract with minimum 20% withanolide glycoside(sample 2 prepared as per example 3) coated with Eudragit (prepared as per example 8) (Dosage 20 mg/kg p.o). |
| Group XI | Reserpine (6 mg/kg i.p) + Purified Ashwagandha root extract with 35% withanolide glycoside (sample 3 prepared as per example 4) (Dosage 100 mg/kg p.o). |
| Group XII | Reserpine (6 mg/kg i.p) + Purified Ashwagandha root extract with 35% withanolide glycoside (sample 3 prepared as per example 4) (Dosage 20 mg/kg p.o). |
| Group XIII | Reserpine (6 mg/kg i.p) + Purified Ashwagandha root extract with 35% withanolide glycoside (sample 3 prepared as per example 4) coated with pectin (prepared as per example 8) (Dosage 20 mg/kg p.o). |
| Group XIV | Reserpine (6 mg/kg i.p) + Purified Ashwagandha root extract with 35% withanolide glycoside (sample 3 prepared as per example 4) coated with Hydroxy propyl methyl cellulose (prepared as per example 8) (Dosage 20 mg/kg p.o). |
| Group XV | Reserpine (6 mg/kg i.p) + Purified Ashwagandha root extract with 35% withanolide glycoside (sample 3 prepared as per example 4) coated with Poly vinyl acetate (PVA) (prepared as per example 8) (Dosage 20 mg/kg p.o). |
| Group XVI | Reserpine (6 mg/kg i.p) + Purified Ashwagandha root extract with 35% withanolide glycoside (sample 3 prepared as per example 4) coated with Shellac (prepared as per example 8) (Dosage 20 mg/kg p.o). |
| Group XVII | Reserpine (6 mg/kg i.p) + Purified Ashwagandha root extract with 35% withanolide glycoside (sample 3 prepared as per example 4) coated with Cellulose acetate phthalate (CAP) (prepared as per example 8) (Dosage 20 mg/kg p.o). |
| Group XVIII | Reserpine (6 mg/kg i.p) + Purified Ashwagandha root extract with 35% withanolide glycoside (sample 3 prepared as per example 4) coated with Eudragit (prepared as per example 8). (Dosage 20 mg/kg p.o). |
| Group XIX | Reserpine (6 mg/kg i.p) + Purified Ashwagandha root extract with 80% withanolide glycoside (sample 5 prepared as per example 5) (Dosage 100 mg/kg p.o). |
| Group XX | Reserpine (6 mg/kg i.p) + Purified Ashwagandha root extract with 80% withanolide glycoside (sample 5 prepared as per example 5) (Dosage 20 mg/kg p.o). |
| Group XXI | Reserpine (6 mg/kg i.p) + Purified Ashwagandha root extract with 80% withanolide glycoside (sample 5 prepared as per example 5) coated with pectin (prepared as per example 8) (Dosage 20 mg/kg p.o). |

TABLE 1-continued

Segregation of rats for experimental study.

| Groups | Treatment |
|---|---|
| Group XXII | Reserpine (6 mg/kg i.p) + Purified Ashwagandha root extract with 80% withanolide glycoside (sample 5 prepared as per example 5) coated with Eudragit (prepared as per example 8). (Dosage 20 mg/kg p.o). |
| Group XXIII | Reserpine (6 mg/kg i.p) + Fluoxetine (10 mg/kg p.o.). |

TABLE 2

Effect of enteric and nonenteric coated purified Ashwagandha extracts on Immobility time in rats.

| Groups | Treatment | Immobility time in seconds |
|---|---|---|
| Group I | Normal control (Received only vehicle; 1% Tween 80 v/v p.o.). | 120 |
| Group II | Reserpine (6 mg/kg i.p) + Vehicle (1% Tween 80 v/v p.o.). | 250 |
| Group III | Reserpine (6 mg/kg i.p) + Ashwagandha extract with minimum 6% withanolide glycoside (Dosage 100 mg/kg p.o.). | 240 |
| Group IV | Reserpine (6 mg/kg i.p) + Ashwagandha extract with minimum 6% withanolide glycoside (Dosage 20 mg/kg p.o.). | 248 |
| Group V | Reserpine (6 mg/kg i.p) + Ashwagandha extract with minimum 6% withanolide glycoside coated with pectin (Dosage 20 mg/kg p.o). | 245 |
| Group VI | Reserpine (6 mg/kg i.p) + Ashwagandha extract with minimum 6% withanolide glycoside coated with Eudragit (Dosage 20 mg/kg p.o.). | 195 |
| Group VII | Reserpine (6 mg/kg i.p) + Ashwagandha extract with minimum 1% withanolide glycoside coated with Eudragit (Dosage 20 mg/kg p.o.). | 242 |
| Group VIII | Reserpine (6 mg/kg i.p) + Ashwagandha extract with minimum 20% withanolide glycoside (Dosage 100 mg/kg p.o.). | 235 |
| Group IX | Reserpine (6 mg/kg i.p) + Ashwagandha extract with minimum 20% withanolide glycoside (Dosage 20 mg/kg p.o). | 239 |
| Group X | Reserpine (6 mg/kg i.p) + Ashwagandha extract with minimum 20% withanolide glycoside coated with Eudragit (Dosage 20 mg/kg p.o.). | 190 |
| Group XI | Reserpine (6 mg/kg i.p) + Purified Ashwagandha extract with 35% withanolide glycoside (Dosage 100 mg/kg p.o.). | 175 |
| Group XII | Reserpine (6 mg/kg i.p) + Purified Ashwagandha extract with 35% withanolide glycoside (Dosage 20 mg/kg p.o) | 210 |
| Group XIII | Reserpine (6 mg/kg i.p) + Purified Ashwagandha extract with 35% withanolide glycoside coated with pectin (Dosage 20 mg/kg p.o.). | 205 |
| Group XIV | Reserpine (6 mg/kg i.p) + Purified Ashwagandha root extract with 35% withanolide glycoside coated with Hydroxy propyl methyl cellulose (Dosage 20 mg/kg p.o). | 207 |
| Group XV | Reserpine (6 mg/kg i.p) + Purified Ashwagandha root extract with 35% withanolide glycoside coated with Poly vinyl acetate (PVA) (Dosage 20 mg/kg p.o) | 204 |
| Group XVI | Reserpine (6 mg/kg i.p) + Purified Ashwagandha root extract with 35% withanolide glycoside coated with Shellac (Dosage 20 mg/kg p.o.). | 162 |
| Group XVII | Reserpine (6 mg/kg i.p) + Purified Ashwagandha root extract with 35% withanolide glycoside coated with Cellulose acetate phthalate (CAP) (Dosage 20 mg/kg p.o.). | 164 |
| Group XVIII | Reserpine (6 mg/kg i.p) + Purified Ashwagandha extract with 35% withanolide glycoside coated with Eudragit. (Dosage 20 mg/kg p.o.). | 160 |
| Group XIX | Reserpine (6 mg/kg i.p) + Purified Ashwagandha extract with 80% withanolide glycoside (Dosage 100 mg/kg p.o.). | 166 |
| Group XX | Reserpine (6 mg/kg i.p) + Purified Ashwagandha extract with 80% withanolide glycoside (Dosage 20 mg/kg p.o.). | 192 |
| Group XXI | Reserpine (6 mg/kg i.p) + Purified Ashwagandha root extract with 80% withanolide glycoside coated with pectin (Dosage 20 mg/kg p.o.). | 189 |
| Group XXII | Reserpine (6 mg/kg i.p) + Purified Ashwagandha root extract with 80% withanolide glycoside coated with Eudragit. (Dosage 20 mg/kg p.o.). | 122 |
| Group XXIII | Reserpine (6 mg/kg i.p) + Fluoxetine (10 mg/kg p.o.). | 122 |

As shown in the Table 2, immobility time for normal control animals was 120 seconds. When reserpine was injected i.p., the animals got depressed and immobility time was increased to 250 seconds (Group II). Oral administration of Ashwagandha extract with 6% withanolide glycosides at 100 mg/kg and 20 mg/kg dosage and Ashwagandha extract with 6% withanolide glycosides coated with pectin after reserpine injection was not much effective and immobility time was recorded as above 240 seconds (Group III-V). But in group VI, Ashwagandha extract with 6% withanolide glycosides coated with Eudragit after reserpine injection, the immobility time was recorded as 195 seconds. When animals were treated with Ashwagandha extract containing minimum 1% withanolide glycosides coated with Eudragit at 20 mg/kg dose, it was not effective and immobility time was found as 242 seconds (Group VII). When animals were treated with Ashwagandha root extract containing minimum 20% withanolide glycosides at 100 mg/Kg dosage, immobility time was 235 seconds (Group VIII) and Ashwagandha root extract containing minimum 20% withanolide glycosides at 20 mg/Kg dosage, immobility time was 239 seconds (Group IX). Whereas Ashwagandha root extract with 20% withanolide glycosides coated with Eudragit at 20 mg/kg dose, immobility time was reduced to 190 seconds (Group X). The immobility time was found as 175 seconds and 210 seconds when animals were treated with purified Ashwagandha extract with 35% withanolide glycosides at 100 mg/kg dose (Group IX) and 20 mg/kg dose (Group XII) respectively. When animals were treated with purified Ashwagandha extract with 35% withanolide glycosides coated with pectin, HPMC and PVA at 20 mg/kg dose, the immobility time was 205, 207 and 204 seconds respectively which indicates very less effectiveness of such nonenteric coatings (Group XIII-XV). In spite of nonenteric coatings, when animals were treated with Ashwagandha extract with 35% withanolide glycosides coated with enteric materials shellac, CAP or Eudragit at 20 mg/kg dose, the immobility time was reduced to 162, 164 and 160 seconds respectively (Group XVI-XVIII) indicating the effectiveness of enteric coating. Animals treated with purified Ashwagandha extract with 80% withanolide glycoside at 100 mg/kg dose and 20 mg/Kg dose showed immobility time as 166 seconds (Group XIX) and 192 seconds (Group XX) respectively. When animals were treated with purified Ashwagandha extract with 80% withanolide glycoside coated with pectin, the immobility time was 189 seconds whereas when same extract was coated with Eudragit, the immobility time was reduced to 122 seconds only showing the effectiveness of enteric coating (Group XXI-XXII). In case of fluoxetine standard (Group XXIII), the immobility time was only 122 seconds which is almost similar to normal control animals.

Example 15

Bioavailability Study Using Different Enteric and Nonenteric Coated Ashwagandha Extracts.

NZ white rabbits weighing 2-2.5 Kg of both sexes were used for the study. The rabbits were kept individually in stainless steel cages and maintained in well ventilated room under normal and uniform conditions like 12 hours light and dark cycle and at 25±2° C. Water and feed were given ad-libitum. The animals were divided into twenty four groups. Each group had 3 animals. All the animals underwent fasting for 12 hours before administration of test samples. The animals were divided as shown in table 1.

TABLE 1

Segregation of rabbits for experimental study.

| Groups | Treatment |
|---|---|
| Group I | Control (1% Tween 80) (Dose: 10 mL/Kg.body wt.). |
| Group II | Ashwagandha extract with minimum 6% withanolide glycosides (sample 2 prepared as per example 2) (Dosage 100 mg/kg p.o). |
| Group III | Ashwagandha extract with minimum 6% withanolide glycosides (sample 2 prepared as per example 2) (Dosage 20 mg/kg p.o). |
| Group IV | Ashwagandha extract with minimum 6% withanolide glycosides (sample 2 prepared as per example 2) coated with pectin (prepared as per example 8) (Dosage 20 mg/kg p.o). |
| Group V | Ashwagandha extract with minimum 6% withanolide glycosides (sample 2 prepared as per example 2) coated with Eudragit (prepared as per example 8) (Dosage 20 mg/kg p.o). |
| Group VI | Ashwagandha extract with minimum 1% withanolide glycoside coated with Eudragit (Dosage 20 mg/kg p.o). |
| Group VII | Ashwagandha extract with minimum 20% withanolide glycoside(sample 2 prepared as per example 3) (Dosage 100 mg/kg p.o). |
| Group VIII | Ashwagandha extract with minimum 20% withanolide glycoside(sample 2 prepared as per example 3) (Dosage 20 mg/kg p.o). |
| Group IX | Ashwagandha extract with minimum 20% withanolide glycoside (sample 2 prepared as per example 3) coated with Eudragit (prepared as per example 8) (Dosage 20 mg/kg p.o). |
| Group X | Purified Ashwagandha extract with 35% withanolide glycoside (sample 3 prepared as per example 4) (Dosage 100 mg/kg p.o). |
| Group XI | Purified Ashwagandha extract with 35% withanolide glycoside (sample 3 prepared as per example 4) (Dosage 20 mg/kg p.o). |
| Group XII | Purified Ashwagandha extract with 35% withanolide glycoside (sample 3 prepared as per example 4) coated with pectin (prepared as per example 8) (Dosage 20 mg/kg p.o). |
| Group XIII | Purified Ashwagandha root extract with 35% (sample 3 prepared as per example 4) coated with Hydroxy propyl methyl cellulose (prepared as per example 8) (Dosage 20 mg/kg p.o). |
| Group XIV | Purified Ashwagandha root extract with 35% withanolide glycoside (sample 3 prepared as per example 4) coated with Poly vinyl acetate (PVA) (prepared as per example 8) (Dosage 20 mg/kg p.o). |

TABLE 1-continued

Segregation of rabbits for experimental study.

| Groups | Treatment |
|---|---|
| Group XV | Purified Ashwagandha root extract with 35% withanolide glycoside (sample 3 prepared as per example 4) coated with Shellac (prepared as per example 8) (Dosage 20 mg/kg p.o). |
| Group XVI | Purified Ashwagandha root extract with 35% withanolide glycoside (sample 3 prepared as per example 4) coated with Cellulose acetate phthalate (CAP) (prepared as per example 8) (Dosage 20 mg/kg p.o). |
| Group XVII | Purified Ashwagandha extract with 35% withanolide glycoside (sample 3 prepared as per example 4) coated with Eudragit (prepared as per example 8). (Dosage 20 mg/kg p.o) |
| Group XVIII | Purified Ashwagandha extract with 80% withanolide glycoside (sample 5 prepared as per example 5) (Dosage 100 mg/kg p.o). |
| Group XIX | Purified Ashwagandha extract with 80% withanolide glycoside (sample 5 prepared as per example 5) (Dosage 20 mg/kg p.o). |
| Group XX | Purified Ashwagandha root extract with 80% withanolide glycoside (sample 5 prepared as per example 5) coated with pectin (prepared as per example 8) (Dosage 20 mg/kg p.o). |
| Group XXI | Purified Ashwagandha root extract with 80% withanolide glycoside (sample 5 prepared as per example 5) coated with Eudragit (prepared as per example 8) (Dosage 20 mg/kg p.o). |
| Group XXII | Ashwagandha extract with 3.5% withanolide glycosides (sample 2 prepared as per example 19) (Dosage 100 mg/kg p.o) |
| Group XXIII | Ashwagandha extract with 3.5% withanolide glycosides (sample 2 prepared as per example 19) (Dosage 20 mg/kg p.o) |
| Group XXIV | Ashwagandha extract with 3.5% withanolide glycosides (sample 2 prepared as per example 19) coated with Eudragit (prepared as per example 20) (Dosage 20 mg/kg p.o) |

The animals were able to access drinking water freely. The extracts were prepared in 1% Tween 80 and fed orally. After 2 hr 30 minutes, 2 ml blood was collected from each rabbit via marginal ear vein in EDTA coated vacutainer tubes. The blood samples were centrifuged at 3000 rpm for 15 minutes and plasma was separated carefully. The plasma samples were stored at −80° C. until analysis. The concentration of withanolide glycosides was analyzed by HPLC.

TABLE 2

Bioavailability study using different enteric and nonenteric coated Ashwagandha extracts.

| Groups | Treatment | withanolide glycosides (ng/ml) |
|---|---|---|
| Group I | Control (Received only vehicle; 1% Tween 80 v/v p.o.). | ND |
| Group II | Ashwagandha extract with minimum 6% withanolide glycosides (Dosage 100 mg/kg p.o). | ND |
| Group III | Ashwagandha extract with minimum 6% withanolide glycosides (Dosage 20 mg/kg p.o). | ND |
| Group IV | Ashwagandha extract with minimum 6% withanolide glycosides coated with Pectin (Dosage 20 mg/kg p.o). | ND |
| Group V | Ashwagandha extract with minimum 6% withanolide glycosides coated with Eudragit (Dosage 20 mg/kg p.o). | 15.2 |
| Group VI | Ashwagandha extract with minimum 1% withanolide glycoside coated with Eudragit (Dosage 20 mg/kg p.o). | 1.6 |
| Group VII | Ashwagandha extract with minimum 20% withanolide glycoside (Dosage 100 mg/kg p.o). | 1.9 |
| Group VIII | Ashwagandha extract with minimum 20% withanolide glycoside (Dosage 20 mg/kg p.o). | 0.3 |
| Group IX | Ashwagandha extract with minimum 20% withanolide glycoside coated with Eudragit (Dosage 20 mg/kg p.o). | 4.2 |
| Group X | Purified Ashwagandha extract with 35% withanolide glycoside (Dosage 100 mg/kg p.o). | 60.3 |
| Group XI | Purified Ashwagandha extract with 35% withanolide glycoside (Dosage 20 mg/kg p.o). | 12.4 |
| Group XII | Purified Ashwagandha extract with 35% withanolide glycoside coated with pectin (Dosage 20 mg/kg p.o). | 13.8 |
| Group XIII | Purified Ashwagandha root extract with 35% withanolide glycoside coated with Hydroxy propyl methyl cellulose (Dosage 20 mg/kg p.o). | 12.9 |
| Group XIV | Purified Ashwagandha root extract with 35% withanolide glycoside coated with Poly vinyl acetate (PVA) (Dosage 20 mg/kg p.o). | 13.2 |
| Group XV | Purified Ashwagandha root extract with 35% withanolide glycoside coated with Shellac (Dosage 20 mg/kg p.o). | 100.3 |

TABLE 2-continued

Bioavailability study using different enteric and nonenteric coated Ashwagandha extracts.

| Groups | Treatment | withanolide glycosides (ng/ml) |
|---|---|---|
| Group XVI | Purified Ashwagandha root extract with 35% withanolide glycoside coated with Cellulose acetate phthalate (CAP) (Dosage 20 mg/kg p.o). | 101.9 |
| Group XVII | Purified Ashwagandha extract with 35% withanolide glycoside coated with Eudragit. (Dosage 20 mg/kg p.o) | 102.3 |
| Group XVIII | Purified Ashwagandha extract with 80% withanolide glycoside (Dosage 100 mg/kg p.o). | 85.2 |
| Group XIX | Purified Ashwagandha extract with 80% withanolide glycoside (Dosage 20 mg/kg p.o). | 18.5 |
| Group XX | Purified Ashwagandha root extract with 80% withanolide glycoside coated with pectin (Dosage 20 mg/kg p.o). | 17.3 |
| Group XXI | Purified Ashwagandha root extract with 80% withanolide glycoside coated with Eudragit (Dosage 20 mg/kg p.o). | 149.8 |
| Group XXII | Ashwagandha extract with 3.5% withanolide glycosides (Dosage 100 mg/kg p.o). | ND |
| Group XXIII | Ashwagandha extract with 3.5% withanolide glycosides (Dosage 20 mg/kg p.o). | ND |
| Group XXIV | Purified Ashwagandha root extract with 3.5% withanolide glycoside coated with Eudragit (Dosage 20 mg/kg p.o). | 10.2 |

As shown in Table 2, withanolide glycosides were not detected in the plasma of animals fed with vehicle, Ashwagandha extract with minimum 6% withanolide glycosides or Ashwagandha root extract with minimum 6% withanolide glycosides coated with pectin (Group I-IV). When animals were fed with Ashwagandha root extract with minimum 6% withanolide glycosides coated with Eudragit at 20 mg/kg, the withanolide glycoside level was found as 15.2 ng/ml (Group V). Withanolide glycosides were not detected in the plasma of animals fed with Ashwagandha extract with 3.5% withanolide glycoside at 100 and 20 mg/kg dose (Group XXII-XXIII), whereas Ashwagandha root extract with 3.5% withanolide glycosides coated with Eudragit at 20 mg/kg, the withanolide glycoside level was found as 10.2 ng/ml (Group XXIV). Animals fed with Ashwagandha extract with minimum 20% withanolide glycosides at 100 and 20 mg/Kg showed withnolide glycoside level in plasma as 1.9 and 0.3 ng/ml respectively. Animals fed with Ashwagandha extract with minimum 1%, and 20% withanolide glycoside coated with Eudragit at 20 mg/kg showed withnolide glycoside level in plasma as 1.6 and 4.2 ng/ml showing the effectiveness of enteric coating in preserving the withanolide glycosides from hydrolysis in the stomach (Group VI &IX). When animals were fed with purified Ashwagandha extract with 35% withanolide glycoside at 100 and 20 mg/kg dose, the withanolide glycoside level in plasma was found as 60.3 and 12.3 ng/ml (Group X-XI). Animals fed with purified Ashwagandha extract with 35% withanolide glycoside coated with pectin, HPMC or PVA at 20 mg/kg dose showed plasma level of withanolide glycosides as 13.8, 12.9 and 13.2 ng/ml respectively (Group XII-XIV). When the same extract, i.e. purified Ashwagandha extract with 35% withanolide glycoside was coated with enteric materials shellac, CAP or Eudragit, the plasma level of withanolide glycosides was increased to 100.3, 101.9 and 102.3 ng/ml respectively, indicating the effectiveness of enteric coating (XV-XVII). When animals were fed with purified Ashwagandha extract with 80% withanolide glycoside at 100 and 20 mg/kg dose, the plasma withanolide glycoside level was found as 85.2 and 18.5 ng/ml respectively (Group XVIII-XIX). When the same extract (purified Ashwagandha extract with 80% withanolide glycoside) was coated with pectin and fed at only 20 mg/kg dose, the withanolide glycoside level was found as 17.3 ng/ml only showing the noneffectiveness of nonenteric coating (Group XX). Whereas when animals were fed with purified Ashwagandha extract with 80% withanolide glycoside coated with eudragit at 20 mg/kg dose, the plasma withanolide glycoside level was found as 149.8 ng/ml showing the protective nature of enteric coating (Group XXI).

Example 16

Efficacy Studies of Ashwagandha Extracts
1. Antistress Activity
a. Anoxia Stress Tolerance Test
Albino Wistar rats of either sex weighing 150-220 g were selected and divided into 11 groups of six each and following treatment was given after one week of acclimatization:

TABLE 1

| Segregation of rats for experimental study | |
|---|---|
| Group I | Control (Received only vehicle; 1% Tween 80 v/v p.o.) |
| Group II | Ashwagandha root extract with 5% withanolide glycosides (sample 2 prepared as per example 6) (100 mg/kg p.o.). |
| Group III | Ashwagandha root extract with 5% withanolide glycosides (sample 2 prepared as per example 6) coated with Eudragit (prepared as per example 8) (100 mg/kg p.o.). |
| Group IV | Alkaloidal rich fraction of Ashwagandha root extract (sample 2 prepared as per example 1) (50 mg/kg p.o.). |
| Group V | Purified Ashwagandha root extract with 80% withanolide glycoside (sample 5 prepared as per example 5) (50 mg/kg p.o.). |

TABLE 1-continued

Segregation of rats for experimental study

| Group VI | Purified Ashwagandha root extract with 80% withanolide glycoside (sample 5 prepared as per example 5) coated with Eudragit(prepared as per example 8) (50 mg/kg p.o.) |
|---|---|
| Group VII | Ashwagandha root extract with 3.5% withanolide glycosides (sample 2 prepared as per example 19) (50 mg/kg p.o.). |
| Group VIII | Ashwagandha root extract with 3.5% withanolide glycosides (sample 2 prepared as per example 19) coated with Eudragit (prepared as per example 20) (50 mg/kg p.o.) |
| Group IX | Ashwagandha raw powder prepared as per example 24(100 mg/kg p.o.). |
| Group X | Ashwagandha raw powder (prepared as per example 24) coated with Eudragit (100 mg/kg p.o.). |
| Group XI | Diazepam (2 mg/kg p.o.). |

Animals were treated as shown above for the 3 weeks. At the end of 1st, 2nd and 3rd week i.e. on 7th, 14th and 21st day 1 h after the treatment stress was induced by placing each animal individually in the hermetic vessel of 1 L capacity to record anoxia tolerance time. The time duration of entry of the animal into the hermetic vessel and the appearance of the first convulsion was taken as time of anoxia.

TABLE 2

Effect of Ashwagandha extracts on anoxia stress tolerance time in rats.

| | | Duration of anoxia stress tolerance in minutes | | |
|---|---|---|---|---|
| Groups | Treatment | First week | Second week | Third week |
| Group I | Control (1% Tween 80 v/v p.o.). | 18.50 | 18.75 | 19.25 |
| Group II | Ashwagandha root extract with 5% withanolide glycosides (100 mg/kg p.o). | 21.33 | 27.67 | 29.00 |
| Group III | Ashwagandha root extract with 5% withanolide glycosides coated with Eudragit (100 mg/kg p.o). | 22.67 | 29.67 | 30.33 |
| Group IV | Alkaloidal rich fraction of Ashwagandha root extract (50 mg/kg p.o.). | 19.33 | 21.67 | 21.00 |
| Group V | Purified Ashwagandha root extract with 80% withanolide glycosides (50 mg/kg p.o.). | 27.50 | 30.33 | 32.67 |
| Group VI | Purified Ashwagandha root extract with 80% withanolide glycosides coated with Eudragit (50 mg/kg p.o.). | 31.67 | 39.33 | 48.67 |
| Group VII | Ashwagandha root extract with 3.5% withanolide glycosides (50 mg/kg p.o.). | 24.96 | 26.47 | 27.12 |
| Group VIII | Ashwagandha root extract with 3.5% withanolide glycosides coated with Eudragit (50 mg/kg p.o.). | 27.63 | 32.78 | 38.98 |
| Group IX | Ashwagandha raw powder (100 mg/kg p.o.). | 20.43 | 23.14 | 24.84 |
| Group X | Ashwagandha raw powder coated with Eudragit (100 mg/kg p.o.). | 21.83 | 23.79 | 25.13 |
| Group XI | Diazepam (2 mg/kg p.o.). | 34.50 | 37.33 | 37.00 |

The results obtained from the anoxia stress tolerance test were expressed as average of six rats (Table 2). Anoxia stress tolerance time was significantly enhanced on 7th, 14th and 21st day in Purified Ashwagandha root extract with 80% withanolide glycosides (50 mg/kg), Purified Ashwagandha root extract with 80% withanolide glycosides coated with Eudragit (50 mg/kg) and Diazepam (2 mg/kg) treated groups. Anoxia stress tolerance time was enhanced on 7th, 14th and 21st day in Ashwagandha root extract with 3.5% withanolide glycosides (50 mg/kg), Ashwagandha root extract with 3.5% withanolide glycosides coated with Eudragit (50 mg/kg). There was increased anoxia tolerance time also seen after 2nd and 3rd week of Ashwagandha root extract with 5% withanolide glycosides (50 mg/kg) treated group but not statistically significant result was obtained on 7th day. Ashwagandha raw powder and Ashwagandha raw powder with enteric coating showed slight increase in anoxia tolerance time (100 mg/Kg). However the effect of alkaloidal rich fraction of Ashwagandha root extract (50 mg/kg) on tolerance time was not statistically significant at the end of 1st, 2nd and 3rd week of treatment.

b. Swimming Endurance Test

Swiss mice of either sex weighing 20-25 g were selected and divided into nine groups of six each and following treatment was given after one week of acclimatization:

TABLE 3

Segregation of mice for experimental study.

| | |
|---|---|
| Group I | Control (Received only vehicle; 1% Tween 80 v/v p.o.). |
| Group II | Ashwagandha root extract with 5% withanolide glycosides (sample 2 prepared as per example 6) (100 mg/kg p.o.). |
| Group III | Ashwagandha root extract with 5% withanolide glycosides coated with Eudragit (prepared as per example 8) (100 mg/kg p.o.). |
| Group IV | Alkaloidal rich fraction of Ashwagandha root extract (sample 2 prepared as per example 1) (50 mg/kg p.o.). |
| Group V | Purified Ashwagandha root extract with 80% withanolide glycoside (sample 5 prepared as per example 5) (50 mg/kg p.o.). |
| Group VI | Purified Ashwagandha root extract with 80% withanolide glycoside (sample 5 prepared as per example 5) coated with Eudragit(prepared as per example 8) (50 mg/kg p.o.). |
| Group VII | Ashwagandha root extract with 3.5% withanolide glycosides (sample 2 prepared as per example 19) (50 mg/kg p.o.). |
| Group VIII | Ashwagandha root extract with 3.5% withanolide glycosides (sample 2 prepared as per example 19) coated with Eudragit (prepared as per example 20) (50 mg/kg p.o.). |
| Group IX | Diazepam (2 mg/kg p.o.). |

Extracts were given to the mice, once daily for period of 7 days. On 8th day the mice were subjected to swimming stress by keeping them in propylene tank of dimension (37×37×30 cm), filled with water to a height of 25 cm. The rats were allowed to swim till complete exhaustion and the endpoint was taken when the animal started drowning. The mean swimming time for each group was calculated.

TABLE 4

Effect of Ashwagandha extracts on swimming endurance in mice.

| Groups | Treatment | Swimming time in minutes |
|---|---|---|
| Group I | Control (1% Tween 80 v/v p.o.). | 32.50 |
| Group II | Ashwagandha root extract with 5% withanolide glycosides (100 mg/kg p.o.). | 39.67 |
| Group III | Ashwagandha root extract with 5% withanolide glycosides coated with Eudragit (100 mg/kg p.o.). | 40.33 |
| Group IV | Alkaloidal rich fraction of Ashwagandha root extract (50 mg/kg p.o.). | 33.75 |
| Group V | Purified Ashwagandha root extract with 80% withanolide glycoside (50 mg/kg p.o.). | 42.00 |
| Group VI | Purified Ashwagandha root extract with 80% withanolide glycoside coated with Eudragit (50 mg/kg p.o.). | 45.50 |
| Group VII | Ashwagandha root extract with 3.5% withanolide glycosides (50 mg/kg p.o.). | 40.72 |
| Group VIII | Ashwagandha root extract with 3.5% withanolide glycosides coated with Eudragit (50 mg/kg p.o.). | 42.81 |
| Group VII | Diazepam (2 mg/kg p.o.). | 58.67 |

The swimming endurance time was significantly enhanced on 8th day in purified Ashwagandha root extract with 80% withanolide glycoside (50 mg/kg), purified Ashwagandha root extract with 80% withanolide glycoside coated with Eudragit (50 mg/kg) and Diazepam (2 mg/kg) treated groups as compared to the control group. The swimming time was also enhanced in Ashwagandha root extract with 5% withanolide glycosides (100 mg/kg) group but it was less than purified Ashwagandha root extract with 80% withanolide glycoside or purified Ashwagandha root extract with 80% withanolide glycoside coated with Eudragit groups. The swimming endurance time was enhanced in Ashwagandha root extract with 3.5% withanolide glycoside (50 mg/kg) and Ashwagandha root extract with 3.5% withanolide glycoside coated with Eudragit (50 mg/kg) as compared to the control group. Alkaloidal rich fraction of Ashwagandha root extract had very little effect on increasing the swimming time.

2. Immunomodulatory Activity a. Effect of *Withania somnifera* Extracts on the Bone Marrow Cellularity and α-Esterase Positive Cells.

Forty two Balb/c mice (20-25 gm) were divided into eight groups with 6 mice in each group. The following treatment was given for 7 days:

TABLE 5

Segregation of mice for experimental study.

| | |
|---|---|
| Group I | Control (Received only vehicle; 1% Tween 80 v/v p.o.) |
| Group II | Ashwagandha root extract with 5% withanolide glycosides (sample 2 prepared as per example 6) (100 mg/kg p.o.). |
| Group III | Ashwagandha root extract with 5% withanolide glycosides coated with Eudragit (prepared as per example 8) (100 mg/kg p.o.). |

TABLE 5-continued

Segregation of mice for experimental study.

| | |
|---|---|
| Group IV | Alkaloidal rich fraction of Ashwagandha root extract (sample 2 prepared as per example 1) (50 mg/kg p.o.). |
| Group V | Purified Ashwagandha root extract with 80% withanolide glycoside (sample 5 prepared as per example 5) (50 mg/kg p.o.). |
| Group VI | Purified Ashwagandha root extract with 80% withanolide glycoside (sample 5 prepared as per example 5) coated with Eudragit(prepared as per example 5) (50 mg/kg p.o.). |
| Group VII | Ashwagandha root extract with 3.5% withanolide glycosides (sample 2 prepared as per example 19) (50 mg/kg p.o.). |
| Group VIII | Ashwagandha root extract with 3.5% withanolide glycosides (sample 2 prepared as per example 19) coated with Eudragit (prepared as per example 20) (50 mg/kg p.o.). |

Animals were sacrificed after the last dose of drug treatment and bone marrow was collected from femur into medium containing 2% Fetal Calf Serum. The number of bone marrow cells was determined using a haemocytometer and expressed as total live cells/femur. A smear of the bone marrow cells from the above preparation was made on clean glass slides and stained with Para-rosaniline hydrochloride and counter stained with hematoxylin to determine the non-specific α-esterase positive cells.

TABLE 6

Effect of Ashwagandha extracts on bone marrow cellularity and α-esterase activity.

| Groups | Treatment | Bone marrow cellularity (cells/femur) | α-esterase activity (No. of α-esterase positive cells) |
|---|---|---|---|
| Group I | Control (1% Tween 80 v/v p.o.). | $14 \times 10^6$ | 1030 |
| Group II | Ashwagandha root extract with 5% withanolide glycosides (100 mg/kg p.o.). | $19 \times 10^6$ | 1410 |
| Group III | Ashwagandha root extract with 5% withanolide glycosides coated with Eudragit (100 mg/kg P.O.). | $20 \times 10^6$ | 1450 |
| Group IV | Alkaloidal rich fraction of Ashwagandha root extract (50 mg/kg p.o.). | $15 \times 10^6$ | 1100 |
| Group V | Purified Ashwagandha root extract with 80% withanolide glycoside (50 mg/kg p.o.). | $24 \times 10^6$ | 1740 |
| Group VI | Purified Ashwagandha root extract with 80% withanolide glycoside coated with Eudragit (50 mg/kg p.o.). | $30 \times 10^6$ | 2300 |
| Group VII | Ashwagandha root extract with 3.5% withanolide glycosides (50 mg/kg p.o.). | $21 \times 10^6$ | 1575 |
| Group VIII | Ashwagandha root extract with 3.5% withanolide glycosides coated with Eudragit (50 mg/kg p.o.). | $23 \times 10^6$ | 1840 |

The effect of Ashwagandha extracts administration on the bone marrow cellularity and α-esterase positive cells is given in Table 6. Both the purified Ashwagandha root extract with 80% withanolide glycoside and purified Ashwagandha root extract with 80% withanolide glycoside coated with Eudragit treated groups showed a significant increase in the bone marrow cells compared to control animals. Ashwagandha extract with 3.5% withanolide glycoside and Ashwagandha extract with 3.5% withanolide glycoside coated with Eudragit showed increase in the bone marrow cells compared to control animals. The Ashwagandha root extract with 5% withanolide glycosides treated animals also showed increase in the bone marrow cells, but it was less as compared to purified Ashwagandha root extract with 80% withanolide glycoside and purified Ashwagandha root extract with 80% withanolide glycoside coated with Eudragit treated groups. There was very slight increase in bone marrow cells in the animals treated with alkaloidal rich fraction of Ashwagandha root extract. Moreover, the number of α-esterase positive cells were also found to be increased significantly in the purified Ashwagandha root extract with 80% withanolide glycoside and purified Ashwagandha root extract with 80% withanolide glycoside coated with Eudragit treated groups compared to controls. Ashwagandha extract with 3.5% withanolide glycoside with and without coating showed increase in number of α-esterase positive cells compared to controls.

b. Effect of Ashwagandha Extracts on Circulating Antibody Titre.

Thirty Six Balb/c mice were immunized with SRBC (0.1 ml, i.p.) and divided into eight groups and treated as follows for 10 days:

TABLE 7

Segregation of mice for experimental study.

| | |
|---|---|
| Group I | Control (Received only vehicle; 1% Tween 80 v/v p.o.). |
| Group II | Ashwagandha root extract with 5% withanolide glycosides (sample 2 prepared as per example 6) (100 mg/kg p.o.). |
| Group III | Ashwagandha root extract with 5% withanolide glycosides (sample 2 prepared as per example 6) coated with Eudragit (prepared as per example 8) (100 mg/kg P.O.). |
| Group IV | Alkaloidal rich fraction of Ashwagandha root extract (sample 2 prepared as per example 1) (50 mg/kg p.o.). |
| Group V | Purified Ashwagandha root extract with 80% withanolide glycoside (sample 5 prepared as per example 5) (50 mg/kg p.o.). |
| Group VI | Purified Ashwagandha root extract with 80% withanolide glycoside (sample5 prepared as per example 5) coated with Eudragit(prepared as per example 8) (50 mg/kg p.o.). |
| Group VII | Ashwagandha root extract with 3.5% withanolide glycosides (sample 2 prepared as per example 19) (50 mg/kg p.o.). |
| Group VIII | Ashwagandha root extract with 3.5% withanolide glycosides (sample 2 prepared as per example 19) coated with Eudragit (prepared as per example 20) (50 mg/kg p.o.). |

Blood was collected from the caudal vein prior to the antigen administration and after the last dose of extracts. Serum was separated and heat inactivated at 56° C. for 30 min. Antibody titre was estimated using SRBC as the antigen. For this, serum was serially diluted with PBS in 96 well round bottom titre plates. Equal volumes of 1% trypsnised SRBC (Ag) were added, mixed gently and incubated at room temperature for 3 h, and the agglutination titers were recorded.

TABLE 8

Effect of Ashwagandha extracts on circulating antibody titre.

| | | Antibody titre | |
|---|---|---|---|
| Groups | Treatment | Initial | Final |
| Group I | Control (1% Tween 80 v/v p.o.). | 22 | 45 |
| Group II | Ashwagandha root extract with 5% withanolide glycosides (100 mg/kg p.o.). | 25 | 242 |
| Group III | Ashwagandha root extract with 5% withanolide glycosides coated with Eudragit (100 mg/kg p.o.). | 23 | 253 |
| Group IV | Alkaloidal rich fraction of Ashwagandha root extract (50 mg/kg p.o.). | 21 | 98 |
| Group V | Purified Ashwagandha root extract with 80% withanolide glycoside (50 mg/kg p.o.). | 28 | 480 |
| Group VI | Purified Ashwagandha root extract with 80% withanolide glycoside coated with Eudragit (50 mg/kg p.o.). | 23 | 750 |
| Group VI | Ashwagandha root extract with 3.5% withanolide glycosides (50 mg/kg p.o.). | 26 | 360 |
| Group VI | Ashwagandha root extract with 3.5% withanolide glycosides coated with Eudragit (50 mg/kg p.o.). | 24 | 550 |

The effect of *Withania somnifera* extracts administration on antibody titre is given in Table 8. Maximum antibody titre value of 750 was observed with purified Ashwagandha root extract with 80% withanolide glycoside coated with Eudragit. Ashwagandha root extract with 3.5% withanolide glycoside coated with Eudragit showed the antibody titre value of 550. Maximum titre value from control animals was found to be 45 only. All other extracts also increased the titre value but these were less than the animals treated with purified Ashwagandha root extract with 80% withanolide glycoside coated with Eudragit.

c. Effect of Ashwagandha Extracts on the Antibody Producing Cells.

The number of plaque forming cells from the spleen was determined by Plaque assay. Thirty six Balb/c mice were divided into eight groups and treated as follows for 7 days:

TABLE 9

Segregation of mice for experimental study.

| Group | |
|---|---|
| Group I | Control (Received only vehicle; 1% Tween 80 v/v p.o.). |
| Group II | Ashwagandha root extract with 5% withanolide glycosides (sample 2 prepared as per example 6) (100 mg/kg p.o.). |
| Group III | Ashwagandha root extract with 5% withanolide glycosides (sample 2 prepared as per example 6) coated with Eudragit (prepared as per example 8) (100 mg/kg p.o.). |
| Group IV | Alkaloidal rich fraction of Ashwagandha root extract (sample 2 prepared as per example 1) (50 mg/kg p.o.). |
| Group V | Purified Ashwagandha root extract with 80% withanolide glycoside (sample 5 prepared as per example 5) (50 mg/kg p.o.). |
| Group VI | Purified Ashwagandha root extract with 80% withanolide glycoside (sample 5 prepared as per example 5) coated with Eudragit(prepared as per example 8) (50 mg/kg p.o.). |
| Group VII | Ashwagandha root extract with 3.5% withanolide glycosides (sample 2 prepared as per example 19) (50 mg/kg p.o.). |
| Group VIII | Ashwagandha root extract with 3.5% withanolide glycosides (sample 2 prepared as per example 19) coated with Eudragit (prepared as per example 20) (50 mg/kg p.o.). |

On $7^{th}$ day the mice were immunized with SRBC ($2.5 \times 10^8$). The animals were sacrificed after 4 days; spleens were processed into a single cell suspension and the cell number was adjusted to $8 \times 10^6$ cells/ml. Fifty microlitres of spleen cell suspension and 50 ml of Ag (SRBC 7%) were mixed with 0.5 ml of 0.5% molten agarose kept at 45° C. and spread on slides. After solidifying the agarose, the gels were incubated in the presence of compliment (rabbit serum at 37° C. for 1 h). Number of plaques was counted using a colony counter.

TABLE 10

Effect of Ashwagandha extracts on antibody producing cells.

| Groups | Treatment | No. of PFC/$10^6$ spleen cells |
|---|---|---|
| Group I | Control (1% Tween 80 v/v p.o.). | 300 |
| Group II | Ashwagandha root extract with 5% withanolide glycosides (100 mg/kg p.o.). | 540 |
| Group III | Ashwagandha root extract with 5% withanolide glycosides coated with Eudragit (100 mg/kg p.o.). | 560 |
| Group IV | Alkaloidal rich fraction of Ashwagandha root extract (50 mg/kg p.o.). | 350 |
| Group V | Purified Ashwagandha root extract with 80% withanolide glycoside ( 50 mg/kg p.o.). | 820 |
| Group VI | Purified Ashwagandha root extract with 80% withanolide glycoside coated with Eudragit (50 mg/kg p.o.). | 1500 |
| Group VII | Ashwagandha root extract with 3.5% withanolide glycosides (50 mg/kg p.o.). | 620 |
| Group VIII | Ashwagandha root extract with 3.5% withanolide glycosides coated with Eudragit (50 mg/kg p.o.). | 890 |

Ashwagandha extract administration was found to significantly enhance the number of antibody producing cells in spleen. The maximum number of plaque forming cells (PFC) was found in the animals treated with purified Ashwagandha root extract with 80% withanolide glycoside coated with Eudragit. Ashwagandha root extract with 3.5% withanolide glycosides also showed an increased number of plaque forming cells (PFC). All other extracts also increased the number of plaque forming cells but these were less than the animals treated with purified Ashwagandha root extract with 80% withanolide glycoside coated with Eudragit.

3. Anti-Inflammatory Activity.

Anti-inflammatory activity of Ashwagandha extracts was assessed by carrageenan induced paw edema model in rats. Forty five wistar rats were divided into nine groups (n=5). Following treatment was given to the rats as single dose:

TABLE 11

Segregation of rats for experimental study.

| Group | |
|---|---|
| Group I | Control (1% Tween 80 v/v p.o.) |
| Group II | Ashwagandha root extract with 5% withanolide glycosides (sample 2 prepared as per example 6) (50 mg/kg p.o.). |
| Group III | Ashwagandha root extract with 5% withanolide glycosides (sample 2 prepared as per example 6) coated with Eudragit (prepared as per example 8) (50 mg/kg p.o.). |
| Group IV | Alkaloidal rich fraction of Ashwagandha root extract (sample 2 prepared as per example 1) (50 mg/kg p.o.). |
| Group V | Purified Ashwagandha root extract with 80% withanolide glycoside (sample 5 prepared as per example 5) ( 50 mg/kg p.o.). |
| Group VI | Purified Ashwagandha root extract with 80% withanolide glycoside (sample 5 prepared as per example 5) coated with Eudragit(prepared as per example 8) (50 mg/kg p.o.). |
| Group VII | Ashwagandha root extract with 3.5% withanolide glycosides (sample 2 prepared as per example 19) (50 mg/kg p.o.). |
| Group VIII | Ashwagandha root extract with 3.5% withanolide glycosides (sample 2 prepared as per example 19) coated with Eudragit (prepared as per example 20) (50 mg/kg p.o.). |
| Group IX | Indomethacin (10 mg/kg p.o.). |

After 30 minutes of extracts 0.1 mL of carrageenan (1% in normal saline) was injected into the right hind paw of each rats. The paw volume was measured plethysmographically at 0, 0.5, 1, 2, 3, 4 and 5th hour after challenge. The percentage inhibition of edema was calculated for each group with respect to the vehicle received control group of animals.

TABLE 12

Percentage inhibition of inflammation in carrageenan induced paw oedema model.

| Groups | Treatment | Percentage inhibition (%) | | | |
|---|---|---|---|---|---|
| | | 0.5 hr | 1 hr | 2 hr | 3 hr |
| Group I | Control (1% Tween 80 v/v p.o.). | 0 | 0 | 0 | 0 |
| Group II | Ashwagandha root extract with 5% withanolide glycosides (50 mg/kg p.o.). | 7 | 12 | 15 | 18 |
| Group III | Ashwagandha root extract with 5% withanolide glycosides coated with Eudragit (50 mg/kg p.o.). | 9 | 16 | 22 | 26 |
| Group IV | Alkaloidal rich fraction of Ashwagandha root extract (50 mg/kg p.o.). | 3 | 8 | 10 | 13 |
| Group V | Purified Ashwagandha root extract with 80% withanolide glycoside (50 mg/kg p.o.). | 20 | 45 | 57 | 69 |
| Group VI | Purified Ashwagandha root extract with 80% withanolide glycoside coated with Eudragit (50 mg/kg p.o.). | 24 | 68 | 75 | 89 |
| Group VII | Ashwagandha root extract with 3.5% withanolide glycosides (50 mg/kg p.o.). | 13 | 19 | 26 | 33 |
| Group VIII | Ashwagandha root extract with 3.5% withanolide glycosides coated with Eudragit (50 mg/kg p.o.). | 20 | 32 | 40 | 52 |
| Group IX | Indomethacin (10 mg/kg p.o.). | 28 | 65 | 80 | 86 |

The maximum percentage inhibition was shown at 3 hour after carrageenan injection. Maximum percentage inhibition of inflammation was observed in animals fed with indomethacin. Among the extracts treated groups, purified Ashwagandha root extract with 80% withanolide glycoside coated with Eudragit was found to be most effective in reducing the inflammation in rat paw.

Ashwagandha root extract with 3.5% withanolide glycoside coated with Eudragit was also found to be effective in reducing the inflammation in rat paw.

Example 17

Toxicity Study in Rats

Twenty four albino rats (14 males and 14 females) weighing 200-250 g were used for this study. The rats were randomly divided in to six groups having two males and two females in each group. The animals were acclimatized for 7 days before the commencement of extract feeding. Following was the grouping of animals (Table 1):

TABLE 1

Grouping of animals in toxicity study.

| S. No. | Group | No. of rats | |
|---|---|---|---|
| | | M | F |
| 1. | Ashwagandha root extract with 5% withanolide glycosides (sample 2 prepared as per example 6) | 2 | 2 |
| 2. | Ashwagandha root extract with 5% withanolide glycosides coated with Eudragit (prepared as per example 8) | 2 | 2 |
| 3. | Alkaloidal rich fraction of Ashwagandha root extract (sample 2 prepared as per example 1) | 2 | 2 |
| 4. | Purified Ashwagandha root extract with 80% withanolide glycoside (sample 5 prepared as per example 5) | 2 | 2 |
| 5. | Purified Ashwagandha root extract with 80% withanolide glycoside (sample 5 prepared as per example 5) coated with Eudragit (prepared as per example 8) | 2 | 2 |
| 6. | Control (1% Tween 80) | 2 | 2 |

The test samples were administered orally at the dose level of 1000 mg/kg body weight daily with the help of a cannula attached with syringe. Similarly, a group of two male and two female rats were treated with vehicle i.e. 1% Tween 80, and were designated as the control group. The animals were observed for a total period of 14 days. Body weight of rats, food consumption, respiration, rectal temperature, general behavior and mortality/severe disability was recorded.

Results

Ashwagandha root extract with 5% withanolide glycosides, Ashwagandha root extract with 5% withanolide glycosides coated with Eudragit as well as alkaloidal rich fraction of Ashwagandha root extract were found to have toxic effects on rats. The animals were more docile and allowed free handling. Among all the groups, the animals fed with alkaloidal rich fraction had decrease in spontaneous movements, sluggish response to stimuli and diminished muscle tone. Power to maintain righting reflex was present. Whereas there were no toxic symptoms in rats fed with purified Ashwagandha root extract with 80% withanolide glycoside, purified Ashwagandha root extract with 80% withanolide glycoside coated with Eudragit and control group.

Loss of appetite was also observed in the rats fed with Ashwagandha root extract with 5% withanolide glycosides or alkaloidal rich fraction whereas the animals fed with purified Ashwagandha root extract with 80% withanolide glycoside, purified Ashwagandha root extract with 80% withanolide glycoside after hydrolysis and purified Ashwagandha root extract with 80% withanolide glycoside coated with Eudragit showed normal appetite which was comparable to control animals. Individual body weights were recorded on day 1, day 7 and day 14 of the study. The gain in body weights of Ashwagandha root extract with 5% withanolide glycosides and alkaloidal rich fraction treated animals was very less whereas the gain in body weight of purified Ashwagandha root extract with 80% withanolide glycoside and purified Ashwagandha root extract with 80% withanolide glycoside coated with Eudragit treated group was comparable to the weight gain of control animals. One rat (female) in Ashwagandha root extract group and three rats (two females and one male) in alkaloidal rich fraction group were died due to clonic convulsions and respiratory depression.

TABLE 2

Feed consumption data

| S. No. | Group | Average daily feed consumption (gm) Male | Female |
|---|---|---|---|
| 1. | Ashwagandha root extract with 5% withanolide glycosides | 25.75 | 22.68 |
| 2. | Ashwagandha root extract with 5% withanolide glycosides coated with Eudragit | 26.22 | 24.66 |
| 3. | Alkaloidal rich fraction of Ashwagandha root extract | 16.24 | 13.33 |
| 4. | Purified Ashwagandha root extract with 80% withanolide glycoside | 38.15 | 36.92 |
| 6. | Purified Ashwagandha root extract with 80% withanolide glycoside coated with Eudragit | 37.92 | 37.05 |
| 7. | Control (1% Tween 80) | 38.55 | 37.13 |

TABLE 3

Body weight (gm) of rats.

| S. No. | Group | Day 1 M | Day 1 F | Day 7 M | Day 7 F | Day 14 M | Day 14 F |
|---|---|---|---|---|---|---|---|
| 1. | Ashwagandha root extract with 5% withanolide glycosides | 214.5 | 211.5 | 210 | 202 | 198 | 189 |
| 2. | Ashwagandha root extract with 5% withanolide glycosides coated with Eudragit | 215.5 | 212 | 211 | 210 | 202.5 | 195.5 |
| 3. | Alkaloidal rich fraction of Ashwagandha root extract | 217 | 210.5 | 205.5 | 201 | 192 | 187 |
| 4. | Purified Ashwagandha root extract with 80% withanolide glycoside | 215.5 | 207 | 223 | 213.5 | 227 | 219 |
| 6. | Purified Ashwagandha root extract with 80% withanolide glycoside coated with Eudragit | 218 | 209 | 224 | 214.5 | 229 | 220 |
| 7. | Control (1% Tween 80) | 216 | 210.5 | 222.5 | 216 | 228 | 221.5 |

TABLE 4

Behavioral and clinical parameters.

| S. | Group | Respiration | Rectal temperature | General behavior | Death |
|---|---|---|---|---|---|
| 1. | Ashwagandha root extract with 5% withanolide glycosides | Mild depression | Decreased by 2° C. | Mild depression of general activity. Prefers to sit quietly. Very cooperative. | 1/4 |
| 2. | Ashwagandha root extract with 5% withanolide glycosides coated with Eudragit | Mild depression | Decreased by 2° C. | Sitting quietly. Cooperative while handling | 1/4 |
| 3. | Alkaloidal rich fraction of Ashwagandha root extract | Moderate depression | Decreased by 3° C. | General activity markedly depressed. Prefers to lie in one corner undisturbed. Sluggish response to stimuli and diminished muscle tone. | 3/4 |
| 4. | Purified Ashwagandha root extract with 80% withanolide glycoside | Normal respiration | No decrease | Normal behavior comparable to control rats. | 0/4 |
| 6. | Purified Ashwagandha root extract with 80% withanolide glycoside coated with Eudragit | Normal respiration | No decrease | Normal behavior comparable to control rats. | 0/4 |
| 7. | Control (1% Tween 80) | Normal respiration | No decrease | Normal behavior | 0/4 |

Example 18

The conversion of withanolide glycosides into aglycon moiety and sugar was studied in simulated gastric fluid (pH 1.2) by in vitro USP dissolution apparatus (LABINDIA DS 8000). The dissolution medium (simulated gastric fluid without enzyme, pH 1.2), free from dissolved air, was filled into the vessel of the dissolution apparatus. Apparatus was assembled and dissolution medium was heated to 36.5° to 37.5°. The enteric coated tablet (prepared as per example 9) containing alkaloid free purified Ashwagandha root extract (sample 5 prepared as per example 5) was sunk to the bottom of one vessel prior to the rotation of the paddle. In another vessel tablet without enteric coating containing purified Ashwagandha root extract (sample 5 prepared as per example 5) was sunk to the bottom of vessel prior to the rotation of the paddle. A suitable device such as a wire of glass helix was used to keep horizontal at the bottom of the vessel tablet that would otherwise float.

An aliquot of the liquid was collected from two vessels at 15, 30, 60, 90 and 120 minutes. The samples were transferred into a liquid-liquid extractor and extracted with chloroform-methanol mixture (80:20). Acidic and chloroform-methanol phases were separated. Chloroform-methanol phase was collected and acidic phase was again extracted with chloroform-methanol two more times. All the chloroform-methanol phases were pooled and extracted with water. Aqueous and chloroform-methanol phases were separated and chloroform-methanol phase was collected. Chloroform-methanol phase was concentrated and dried to form powder of chloroform-methanol extract. Chloroform-methanol extract is dissolved in methanol and analysed by HPLC.

|  | Percentage of aglycone withanolide | |
| --- | --- | --- |
| Time (Min) | Enteric coated tablet of alkaloid free purified Ashwagandha root extract | Tablet of purified Ashwagandha root extract without enteric coating |
| 0 | 0 | 0 |
| 15 | 1.2 | 33.8 |
| 30 | 2.3 | 46.7 |
| 60 | 3.6 | 59.8 |
| 90 | 4.1 | 65.3 |
| 120 | 4.8 | 74.8 |

It was found that at 15 minutes in acidic medium withanolide glycosides in tablet of purified Ashwagandha root extract without enteric coating was converted into withanolide aglycones (33.8%), but only 1.2 percent of withanolide aglycones were formed following the administration of enteric coated tablet of alkaloid free purified Ashwagandha root extract. At 2 hours 74.8 percent of withanolide aglycones were formed in the acidic environment following the administration of tablet of purified Ashwagandha root extract without enteric coating. After administration of enteric coated tablet of alkaloid free purified Ashwagandha root extract only 4.8 percent of withanolide aglycones were formed in the acidic condition. Withanolide glycosides undergo hydrolysis in acidic pH and get converted to withanolide aglycones which is toxic. The enteric coating prevented the hydrolysis of active compound like withanolide glycoside to aglycones in the Ashwagandha root extract in the acidic environment.

Example 19

Method of Making Ashwagandha Extract with 3.5% Withanolide Glycoside.

Roots of Ashwagandha were collected (100 Kg). Roots of Ashwagandha were cleaned. Cleaned roots were treated with 2% ammonia solution in a ratio of 1:2 solvent:roots of Ashwagandha for 4 hrs. Ammonia treated Ashwagandha roots were filled in the Soxhlet extractor and extracted with dichloromethane or methylene dichloride (MDC) (300 L). The extraction was carried out for 10 hrs at a temperature of about 70° C. After the completion of extraction, the supernatant and residue were separated by filtration. Residue (roots of Ashwagandha) after MDC extraction was washed with water till the pH become neutral. Then dried the root in a vacuum oven at 90-100° C. After drying the roots of Ashwagandha was powdered to form a powder of roots of Ashwagandha (sample 1) (88%).

88 Kg of powder of roots of Ashwagandha (sample 1) was extracted with 20% ethanol. Sample 1 was refluxed with 20% ethanol (300 L) at the boiling temperature (75-80° C.) of ethanol for one hour to obtain a second residue and second supernatant. The second residue was then further extracted two more times with three times the quantity of ethanol at each time. The residue and supernatants were separated. All the supernatants were pooled and concentrated in an Agitated thin film evaporator (ATFE) to form a concentrated ethanol extract. The concentrated ethanol extract was filtered to get filtrate and third residue. 35% maltodextrin was added to the filtrate and spray dried to get powder of 20% ethanol extract of Ashwagandha. The yield was about 18% (Sample 2).

See also extract preparation in FIG. 7.

The withanolide glycoside content in powder of ammonia treated 20% ethanol extract of Ashwagandha was about 3.5% by HPLC. Saponin content in powder of ammonia treated 20% ethanol extract of Ashwagandha was about 2.5% by UV method. Alkaloid content in powder of ammonia treated 20% methanol extract of Ashwagandha was about 0.06% by gravimetry method. Withanolide aglycones content in powder of ammonia treated 20% ethanol extract of Ashwagandha was about 0.15% by HPLC. Oligosaccharide content in powder of ammonia treated 20% ethanol extract of Ashwagandha was about 3% by HPLC.

Example 20

Method of Making Enteric Coated Ashwagandha Root Extract Granules with 3.5% Withanolide Glycoside.

1 Kg of Ashwagandha root extract powder with 3.5% withanolide glycoside was passed through the Roll Compactor machine. The flakes obtained from the roll compactor were passed through an Oscillating Granulator machine fitted with 16 mesh screen to obtain granules of Ashwagandha root extract.

Granules of Ashwagandha root extract was loaded into the bowl of the fluid bed extractor (pam glatt pharma technologies). The bowl has a fine Stainless steel mesh at the bottom. The air used for drying/fluidizing was successively filtered through HEPA (High-efficiency particulate arrestance) filters (EU 13 grade, 0.3 micron rating, 99.997% efficiency).

Hot, filtered air up to 90° C. was passed at high velocity from the bottom of the FBE bowl through the feed material (Ashwagandha root extract with 3.5% Withanolide glycoside) and feed material was fluidised.

Meantime, 100 g coating material (Poly-methacrylic acid-co-methyl methacrylate (Eudragit) was dissolved in 900 ml water. Coating solution was sprayed into fluidised material by using a spraying devise attached to the FBE (spray speed 0.5 L in 1 Hr, pump rpm range 10-12). Through the process of fluid bed coating, fluidized particles are continuously sprayed with coating solution, depositing layers (films) of material to the surface of the particles, and yielding an even layer, 4% weight gain with 6 mg/cm$^2$ thickness.

Example 21

Method of Making Minitablet of Ashwagandha Root Extract with 3.5% Withanolide Glycoside.

5 Kg powder of 20% ethanol extract of Ashwagandha was mixed with 19% Micro Crystalline Cellulose (MCC) and 1% Magnesium stearate. So the loading of the original extract was 80%. This mixture was fed in tableting machine having 3 mm dies and punches to get the 3 mm diameter mini tablets with 9 Kg/cm² hardness.

Example 22

Method of Making Enteric Coated Mini Tablet of Ashwagandha Root Extract with 3.5% Withanolide Glycoside.

The mini tablets prepared as per example 21 were coated by Pan coating method. In brief, 4 Kg mini tablets with 3 mm diameter were introduced into the Pan and rotated at 20 rpm. Coating material (EUDRAGUARD brand enteric coating polymer from Evonik) was sprayed on to the tablets via a spray gun as 30% aqueous dispersion. Simultaneously hot blower (110 degree) was started for fast drying of the tablets. Tablets were coated till a weight gain of 12%. After coating, tablets were further kept in hot air stream for 15 minutes to ensure complete drying.

Example 23

Roots of Ashwagandha were collected (100 Kg). Roots of Ashwagandha were cleaned. Cleaned roots were extracted with 100% methanol. Roots were refluxed with 100% methanol at the boiling temperature (60-70° C.) of methanol for one hour to obtain a first residue and first supernatant. The first residue was then further extracted two more times with four times the quantity of methanol at each time. The residue and supernatants were separated. All the supernatants were pooled and concentrated in an Agitated thin film evaporator (ATFE) to form a concentrated methanol extract. The concentrated methanol extract was dried under vacuum at above 500 mm of mercury to get powder of 100% methanol extract of Ashwagandha (yield 6%).

Withanolide glycoside content in powder of 100% methanol extract of Ashwagandha was 1% by HPLC Example 24

Method of Preparation of Ashwagandha Root Powder.

Fresh roots of Ashwagandha were collected (100 Kg). Roots of Ashwagandha were cleaned. Cleaned roots were dried. Dried roots were pulverized to get powder of root Ashwagandha (Yield 70%).

Withanolide glycoside content in Ashwagandha powder was 0.6% by HPLC.

Example 25

Method of Analysis of Saponins by Spectrophotometric Method.

50 mg Ashwagandha extract was weighed into a 50 ml standard flask and make up to the volume by adding water. Standard was prepared by weighing accurately 5 mg standard [standard Protodioscin 97.2% purity from Chromadex] and transferred into a 5 ml standard flask and made up to a 5 ml solution with water. 1 ml of sample and 1 ml standard were pipette out into two separate test tubes. 1 ml of anisaldehyde reagent was added to each tube and mixed well. Mixture was kept for 10 minutes. 4 ml of 70% sulphuric acid reagent was added to each tube and mixed. Tubes were kept in water bath with constant temperature of 60° c. After 10 minutes, tubes were cooled and absorbance was taken at 435 nm. Saponins were determined by the formula $$\text{Total saponin} = \frac{\text{Absorbance of sample} \times \text{Standard concentration} \times \text{purity of Standard}}{\text{Absorbance of Standard} \times \text{sample concentration}}$$

Example 26

Method of Preparation of Different Ashwagandha Powder/Extract in Different pH.

Ashwagandha powder/extract was added to different buffer (pH 1, 2, 3, 5, 7 and 7.4) in 1:20 ratio of Ashwagandha powder/extract:buffer. The extract-buffer solution was kept in a waterbath at 37° C. for 2 hrs. The solution was neutralised by adding base or acid solution. The neutralised solution was concentrated and dried.

Example 27

Method of Making Amaranth Extract with 9% Nitrate.

Fresh Amaranth were collected (100 Kg). Leaves and stem of fresh Amaranth were cleaned and crushed. Water in an amount ten times the quantity of crushed material of Amaranth was added to form a mixture. The extraction was performed using an extractor with a reflux condenser. The bottom of the extractor was fitted with a polypropylene (100 microns) filter cloth. The mixture was refluxed for one hour to obtain a first residue and supernatant. The residue and supernatants were separated by draining out the supernatant from the extractor bottom through the polypropylene filter cloth using a centrifugal pump. After the first extraction, the first residue was further extracted with ten times the quantity of water to get second residue and supernatant. The second residue was further extracted with ten times the quantity of water to get third residue and supernatant. All the supernatants were pooled and concentrated in an Agitated thin film evaporator (ATFE) at a temperature of 85° C. to form concentrated water extract (yield 3%).

Concentrated water extract was passed through a carbon column to obtain a filtrate. Filtrate was concentrated and clarified to form a supernatant and residue. Supernatant was dried under vacuum at above 500 mm of mercury to get powder of purified water extract of fresh Amaranth (Yield 2.5 Kg).

The nitrate content in water extract of fresh Amaranth by ion chromatography was found to be 9%.

Example 28

Method of Making Combination of Enteric Coated Ashwagandha Root Extract with 3.5% Withanolide Glycoside and Amaranth Extract with 9% Nitrate.

2.5 Kg of Enteric coated Ashwagandha extract prepared as per example 20 and 2.5 Kg of Amaranth extract prepared as per Example 25 was blended in 1:1 ratio by using Double Cone Blender (stainless steel SS-316, capacity 2000 litre, manufacturer: Zebra Pharma, Mumbai).

Example 29

Efficacy Study of Different Ashwagandha Extracts Granules and Powder Treated at Different pH.

108 rats were divided into 27 groups comprising of 4 rats in each group. The animals were trained for swimming test (15 minutes) as pre-test session and then fasted overnight. To the fasted animals, reserpine (6 mg/kg) was injected i.p. to depress the animals. After 1 hour of reserpine injection, the test samples treated at different pH/standard were fed orally as designated dose. After 1 hour of test sample/standard, the rats were tested using forced swim test and duration of immobility in the 5 minutes test session was recorded. In this test more immobility time indicate that animal is more depressed or stressed.

TABLE 1

Effect of different Ashwagandha powder/extracts granules in different pH on Immobility time in rats.

| Groups | Treatment | Immobility time in seconds |
|---|---|---|
| Group I | Normal control (Received only vehicle; 1% Tween 80 v/v p.o.). | 120 |
| Group II | Reserpine (6 mg/kg i.p) + Vehicle (1% Tween 80 v/v p.o.) | 250 |
| Group III | Reserpine (6 mg/kg i.p) + Ashwagandha root powder (Prepared as per example 24) at pH1(Prepared as per example 26) (Dosage 200 mg/kg p.o). | 245 |
| Group IV | Reserpine (6 mg/kg i.p) + Ashwagandha root powder at pH2 (Dosage 200 mg/kg p.o). | 245 |
| Group V | Reserpine (6 mg/kg i.p) + Ashwagandha root powder at pH3 (Dosage 200 mg/kg p.o). | 230 |
| Group VI | Reserpine (6 mg/kg i.p) + Ashwagandha root powder at pH5 (Dosage 200 mg/kg p.o). | 220 |
| Group VII | Reserpine (6 mg/kg i.p) + Ashwagandha root powder at pH7 (Dosage 200 mg/kg p.o). | 205 |
| Group VIII | Reserpine (6 mg/kg i.p) + Ashwagandha root powder at pH7.4 (Dosage 200 mg/kg p.o). | 205 |
| Group IX | Reserpine (6 mg/kg i.p) + Ashwagandha extract with 3.5% withanolide glycosides(prepared as per example 19) at pH1(prepared as per example 26) (Dosage 60 mg/kg p.o). | 235 |
| Group X | Reserpine (6 mg/kg i.p) + Ashwagandha extract with 3.5% withanolide glycosides at pH2 (Dosage 60 mg/kg p.o). | 230 |
| Group XI | Reserpine (6 mg/kg i.p) + Ashwagandha extract with 3.5% withanolide glycosides at pH 3 (Dosage 60 mg/kg p.o). | 210 |
| Group XII | Reserpine (6 mg/kg i.p) + Ashwagandha extract with 3.5% withanolide glycosides at pH 5 (Dosage 60 mg/kg p.o). | 189 |
| Group XIII | Reserpine (6 mg/kg i.p) + Ashwagandha extract with 3.5% withanolide glycosides at pH 7 (Dosage 60 mg/kg p.o). | 152 |
| Group XIV | Reserpine (6 mg/kg i.p) + Ashwagandha extract with 3.5% withanolide glycosides at pH 7.4 (Dosage 60 mg/kg p.o). | 150 |
| Group XV | Reserpine (6 mg/kg i.p) + Ashwagandha extract with 35% withanolide glycosides(sample 3 prepared as per example 4) at pH 1(Dosage 20 mg/kg p.o). | 220 |
| Group XVI | Reserpine (6 mg/kg i.p) + Ashwagandha extract with 35% withanolide glycosides (sample 3 prepared as per example 4)at pH 2(prepared as per example 26)(Dosage 20 mg/kg p.o). | 220 |
| Group XVII | Reserpine (6 mg/kg i.p) + Ashwagandha extract with 35% withanolide glycosides at pH 3(Dosage 20 mg/kg p.o). | 202 |
| Group XVIII | Reserpine 6 mg/kg i.p) + Ashwagandha extract with 35% withanolide glycosides at pH 5(Dosage 20 mg/kg p.o). | 180 |
| Group XIX | Reserpine 6 mg/kg i.p) + Ashwagandha extract with 35% withanolide glycosides at pH 7 (Dosage 20 mg/kg p.o). | 145 |
| Group XX | Reserpine (6 mg/kg i.p) + Ashwagandha extract with 35% withanolide glycosides at pH 7.4 (Dosage 20 mg/kg p.o). | 139 |
| GroupXI | Reserpine 6 mg/kg i.p) + Ashwagandha extract with 80% withanolide glycosides(sample 5 prepared as per example 5) at pH 1(prepared as per example 26)(Dosage 20 mg/kg p.o). | 212 |
| GroupXII | Reserpine (6 mg/kg i.p) + Ashwagandha extract with 80% withanolide glycosides at pH 2(Dosage 20 mg/kg p.o). | 211 |
| GroupXIII | Reserpine 6 mg/kg i.p) + Ashwagandha extract with 80% withanolide glycosides at pH 3(Dosage 20 mg/kg p.o). | 194 |
| Group XIV | Reserpine 6 mg/kg i.p) + Ashwagandha extract with 80% withanolide glycosides at pH 5(Dosage 20 mg/kg p.o). | 165 |
| Group XV | Reserpine 6 mg/kg i.p) + Ashwagandha extract with 80% withanolide glycosides at pH 7 (Dosage 20 mg/kg p.o). | 110 |
| Group XVI | Reserpine 6 mg/kg i.p) + Ashwagandha extract with 80% withanolide glycosides at pH 7.4 (Dosage 20 mg/kg p.o). | 105 |
| Group XVII | Reserpine(6 mg/kg i.p) + Fluoxetine (10 mg/kg p.o.). | 120 |

As shown in the Table 1, immobility time for normal control animals was 120 seconds. When reserpine was injected i.p., the animals got depressed and immobility time increased to 250 seconds (Group II). Oral administration of Ashwagandha root powders (200 mg/kg) at pH 1, 2, 3 and 5 after reserpine injection was not much effective and immobility time was recorded as 245, 245, 230 and 220 seconds respectively (Group III to VI). Administration of Ashwagandha root powders (200 mg/kg) at pH 7 and 7.4 after reserpine injection was slightly effective and immobility time was recorded as 205 seconds (Group VII to VIII). Similarly, administration of Ashwagandha extract with 3.5% withanolide glycosides (60 mg/kg) at pH 1, 2, 3 and 5 after reserpine injection was slightly effective (better than ashwagandha root powder) and immobility time was recorded as 235, 230, 210 and 189 seconds respectively (Group IX to XII). Whereas, administration of Ashwagandha extract with 3.5% withanolide glycosides (60 mg/kg) at pH 7 and 7.4 after reserpine injection was more effective and immobility time was recorded as 152 and 150 seconds respectively (Group XIII to XIV).

Administration of Ashwagandha extract with 35% withanolide glycosides (20 mg/kg) at pH 1, 2, 3 and 5 after reserpine injection was effective and immobility time was recorded as 220, 220, 202 and 180 seconds respectively (Group XV to XVIII). Whereas, administration of Ashwagandha extract with 35% withanolide glycosides (20 mg/kg) at pH 7 and 7.4 after reserpine injection was more effective and immobility time was recorded as 145 and 139 seconds respectively (Group XIX to XX).

In case of administration of extracts containing very high (80%) withanolide glycosides (20 mg/kg) at pH 1, 2, 3 and 5 after reserpine injection was effective and immobility time was recorded as 212, 211, 194 and 165 seconds respectively (Group XXI to XIV). Whereas, administration of Ashwagandha extract with 80% withanolide glycosides (20 mg/kg) at pH 7 and 7.4 after reserpine injection was most effective and immobility time was recorded as 110 and 105 seconds respectively (Group XV to XVI). In case of fluoxetine standard at 10 mg/kg (Group XVII), the immobility time was only 122 seconds which is almost similar to normal control animals.

Example 30

Efficacy Study of Different Ashwagandha Extracts Granules with Normal (Film), Enteric and Delayed Release Coating.

60 rats were divided into 15 groups comprising of 4 rats in each group. The animals were trained for swimming test (15 minutes) as pre-test session and then fasted overnight. To the fasted animals, reserpine (6 mg/kg) was injected i.p. to depress the animals. Immediately after reserpine injection, the test samples with normal (Hydroxy Propyl Cellulose; HPC), enteric (Eudragit) and delayed release (High percentage of Eudragit) coating/standard were fed orally as designated doses. After 2 hour of test sample/standard, the rats were tested using forced swim test and duration of immobility in the 5 minutes test session was recorded. In this test more immobility time indicate that animal is more depressed or stressed.

TABLE 1

Effect of different Ashwagandha powder/granules with normal/enteric/delayed release coating on Immobility time in rats.

| Groups | Treatment | Immobility time in seconds |
|---|---|---|
| Group I | Normal control (Received only vehicle; 1% Tween 80 v/v p.o.). | 120 |
| Group II | Reserpine (6 mg/kg i.p) + Vehicle (1% Tween 80 v/v p.o.). | 250 |
| Group III | Reserpine (6 mg/kg i.p) + Ashwagandha root powder (Prepared as per example 24)with normal HPC coating (Dosage 200 mg/kg p.o).. | 245 |
| Group IV | Reserpine (6 mg/kg i.p) + Ashwagandha root powder (Prepared as per example 24)with enteric coating (Dosage 200 mg/kg p.o). | 205 |
| Group V | Reserpine (6 mg/kg i.p) + Ashwagandha root powder (Prepared as per example 24)with delayed release coating (Dosage 200 mg/kg p.o). | 220 |
| Group VI | Reserpine (6 mg/kg i.p) + Ashwagandha granules with 3.5% withanolide glycosides (sample 2 prepared as per example 19) with normal HPC coating (Dosage 60 mg/kg p.o). | 215 |
| Group VII | Reserpine (6 mg/kg i.p) + Ashwagandha granules with 3.5% withanolide glycosides (sample 2 prepared as per example 19)with enteric coating(Dosage 60 mg/kg p.o). | 141 |
| Group VIII | Reserpine (6 mg/kg i.p) + Ashwagandha granules with 3.5% withanolide glycosides (sample 2 prepared as per example 19)with delayed release coating(Dosage 60 mg/kg p.o). | 186 |
| Group IX | Reserpine (6 mg/kg i.p) + Ashwagandha granules with 35% withanolide glycosides (sample 3 prepared as per example 4)with normal HPC coating (Dosage 20 mg/kg p.o). | 192 |
| Group X | Reserpine (6 mg/kg i.p) + Ashwagandha granules with 35% withanolide glycosides (sample 3 prepared as per example 4) with enteric coating (Dosage 20 mg/kg p.o). | 138 |
| Group XI | Reserpine (6 mg/kg i.p) + Ashwagandha granules with 35% withanolide glycosides (sample 3 prepared as per example 4) with delayed release coating (Dosage 20 mg/kg p.o). | 162 |
| Group XII | Reserpine (6 mg/kg i.p) + Ashwagandha granules with 80% withanolide glycosides (sample 5 prepared as per example 5) with normal HPC coating (Dosage 20 mg/kg p.o). | 173 |
| Group XIII | Reserpine (6 mg/kg i.p) + Ashwagandha granules with 80% withanolide glycosides(sample 5 prepared as per example 5) with enteric coating (Dosage 20 mg/kg p.o). | 109 |
| Group XIV | Reserpine (6 mg/kg i.p) + Ashwagandha granules with 80% withanolide glycosides (sample 5 prepared as per example 5)with delayed release coating (Dosage 20 mg/kg p.o). | 132 |
| Group XV | Reserpine(6 mg/kg i.p) + Fluoxetine (10 mg/kg p.o.). | 120 |

As shown in the Table 1, immobility time for normal control animals was 120 seconds. When reserpine was injected i.p., the animals got depressed and immobility time was increased to 250 seconds (Group II). Oral administration of Ashwagandha root powder with normal HPC coating (200 mg/kg) after reserpine injection was not much effective and immobility time was recorded as 245 seconds (Group III). Administration of Ashwagandha root powder with enteric coating (200 mg/kg) after reserpine injection was more effective than HPC coating and immobility time was recorded as 205 seconds (Group IV). Administration of Ashwagandha root powder with delayed release coating (200 mg/kg) after reserpine injection was less effective than enteric coating and immobility time was recorded as 220 seconds (Group V).

Similarly, oral administration of Ashwagandha granules with 3.5% withanolide glycosides with normal HPC coating (60 mg/kg) after reserpine injection was not much effective and immobility time was recorded as 215 seconds (Group VI). Administration of Ashwagandha granules with 3.5% withanolide glycosides with enteric coating (60 mg/kg) after reserpine injection was more effective than HPC coating and immobility time was recorded as 141 seconds (Group VII). Administration of Ashwagandha granules with 3.5% withanolide glycosides with delayed release coating (60 mg/kg) after reserpine injection was less effective than enteric coating and immobility time was recorded as 186 seconds (Group VIII).

Oral administration of Ashwagandha granules with 35% withanolide glycosides with normal HPC coating (20 mg/kg) after reserpine injection was slightly effective and immobility time was recorded as 192 seconds (Group IX). Administration of Ashwagandha granules with 35% withanolide glycosides with enteric coating (20 mg/kg) after reserpine injection was more effective than HPC coating and immobility time was recorded as 138 seconds (Group X). Administration of Ashwagandha granules with 35% withanolide glycosides with delayed release coating (20 mg/kg) after reserpine injection was less effective than enteric coating and immobility time was recorded as 162 seconds (Group XI).

Oral administration of Ashwagandha granules with 80% withanolide glycosides with normal HPC coating (20 mg/kg) after reserpine injection was effective and immobility time was recorded as 173 seconds (Group XII). Administration of Ashwagandha granules with 80% withanolide glycosides with enteric coating (20 mg/kg) after reserpine injection was most effective than HPC coating and immobility time was recorded as 109 seconds (Group XIII). Administration of Ashwagandha granules with 80% withanolide glycosides with delayed release coating (20 mg/kg) after reserpine injection was less effective than enteric coating and immobility time was recorded as 132 seconds (Group XIV). In case of fluoxetine standard at 10 mg/kg (Group XVII), the immobility time was 120 seconds which is similar to normal control animals.

Example 31

Efficacy Study of Different Ashwagandha Extracts Granules with Different Percentage of Enteric Coating.

44 rats were divided into 11 groups comprising of 4 rats in each group. The animals were trained for swimming test (15 minutes) as pre-test session and then fasted overnight. To the fasted animals, reserpine (6 mg/kg) was injected i.p. to depress the animals. Immediately after the reserpine injection, the test samples (ashwagandha root powder) with different percentage of enteric coating/standard were fed orally as designated dose. After 2 hour of test sample/standard, the rats were tested using forced swim test and duration of immobility in the 5 minutes test session was recorded. In this test more immobility time indicate that animal is more depressed or stressed.

The test was repeated with different percentage of coated ashwagandha extract containing 3.5% withanolide glycosides and different percentage of coated ashwagandha extract containing 35% and 80% withanolide glycosides.

TABLE 1

Effect of Ashwagandha powder with different percentage of enteric coating on Immobility time in rats.

| Groups | Treatment | Immobility time in seconds |
|---|---|---|
| Group I | Normal control (Received only vehicle; 1% Tween 80 v/v p.o.). | 120 |
| Group II | Reserpine (6 mg/kg i.p) + Vehicle (1% Tween 80 v/v p.o.). | 250 |
| Group III | Reserpine (6 mg/kg i.p) + Ashwagandha root powder (Prepared as per example 24) with 0.5% enteric coating (Dosage 200 mg/kg p.o). | 245 |
| Group IV | Reserpine (6 mg/kg i.p) + Ashwagandha root powder (Prepared as per example 24) with 1% enteric coating (Dosage 200 mg/kg p.o). | 235 |
| Group V | Reserpine (6 mg/kg i.p) + Ashwagandha root powder (Prepared as per example 24) with 3% enteric coating (Dosage 200 mg/kg p.o). | 223 |
| Group VI | Reserpine (6 mg/kg i.p) + Ashwagandha root powder (Prepared as per example 24) with 5% enteric coating (Dosage 200 mg/kg p.o). | 216 |
| Group VII | Reserpine (6 mg/kg i.p) + Ashwagandha root powder with 7% enteric coating (Dosage 200 mg/kg p.o). | 207 |
| Group VIII | Reserpine (6 mg/kg i.p) + Ashwagandha root powder (Prepared as per example 24) with 10% enteric coating (Dosage 200 mg/kg p.o). | 201 |
| Group IX | Reserpine (6 mg/kg i.p) + Ashwagandha root powder with 12% enteric coating (Dosage 200 mg/kg p.o). | 200 |
| Group X | Reserpine (6 mg/kg i.p) + Ashwagandha root powder (Prepared as per example 24) with 15% enteric coating (Dosage 200 mg/kg p.o). | 200 |
| Group XI | Reserpine(6 mg/kg i.p) + Fluoxetine (10 mg/kg p.o.). | 120 |

As shown in the Table 1, immobility time for normal control animals was 120 seconds. When reserpine was injected i.p., the animals got depressed and immobility time was increased to 250 seconds (Group II). Oral administration of Ashwagandha root powder with 0.5%, 1% and 3% enteric coating (200 mg/kg) after reserpine injection was not much effective and immobility time was recorded as 245, 235 and 223 seconds respectively (Group III to V). Administration of Ashwagandha root powder with 5 and 7% enteric coating (200 mg/kg) after reserpine injection was more effective than lower percentage of coatings and immobility time was recorded as 216 and 207 seconds respectively (Group VI to VII). Administration of Ashwagandha root powder with 10, 12 and 15% enteric coating (200 mg/kg) after reserpine injection was most effective and immobility time was recorded as 201, 200 and 200 seconds respectively (Group VIII to X). In case of fluoxetine standard at 10 mg/kg (Group XI), the immobility time was 120 seconds which is similar to normal control animals.

TABLE 2

Effect of Ashwagandha extract with 3.5% withanolide glycoside with different percentage of enteric coating on Immobility time in rats.

| Groups | Treatment | Immobility time in seconds |
|---|---|---|
| Group I | Normal control (Received only vehicle; 1% Tween 80 v/v p.o.). | 120 |
| Group II | Reserpine (6 mg/kg i.p) + Vehicle (1% Tween 80 v/v p.o.). | 250 |
| Group III | Reserpine (6 mg/kg i.p) + Ashwagandha extract with 3.5% withanolide glycosides (sample 2 prepared as per example 19) with 0.5% enteric coating (Dosage 60 mg/kg p.o). | 225 |
| Group IV | Reserpine (6 mg/kg i.p) + Ashwagandha extract with 3.5% withanolide glycosides (sample 2 prepared as per example 19) with 1% enteric coating (Dosage 60 mg/kg p.o). | 220 |
| Group V | Reserpine (6 mg/kg i.p) + Ashwagandha extract with 3.5% withanolide glycosides (sample 2 prepared as per example 19) with 3% enteric coating (Dosage 60 mg/kg p.o). | 206 |
| Group VI | Reserpine (6 mg/kg i.p) + Ashwagandha extract with 3.5% withanolide glycosides (sample 2 prepared as per example 19) with 5% enteric coating (Dosage 60 mg/kg p.o). | 195 |
| Group VII | Reserpine (6 mg/kg i.p) + Ashwagandha extract with 3.5% withanolide glycosides (sample 2 prepared as per example 19) with 7% enteric coating (Dosage 60 mg/kg p.o). | 180 |
| Group VIII | Reserpine (6 mg/kg i.p) + Ashwagandha extract with 3.5% withanolide glycosides with 10% enteric coating (Dosage 60 mg/kg p.o). | 160 |
| Group IX | Reserpine (6 mg/kg i.p) + Ashwagandha extract with 3.5% withanolide glycosides (sample 2 prepared as per example 19) with 12% enteric coating (Dosage 60 mg/kg p.o). | 142 |
| Group X | Reserpine (6 mg/kg i.p) + Ashwagandha extract with 3.5% withanolide glycosides (sample 2 prepared as per example 19) with 15% enteric coating (Dosage 60 mg/kg p.o). | 140 |
| GroupXI | Reserpine(6 mg/kg i.p) + Fluoxetine (10 mg/kg p.o.). | 120 |

As shown in the Table 2, immobility time for normal control animals was 120 seconds. When reserpine was injected i.p., the animals got depressed and immobility time was increased to 250 seconds (Group II). Oral administration of Ashwagandha extract with 3.5% withanolide glycosides with 0.5%, 1% and 3% enteric coating (60 mg/kg) after reserpine injection was not much effective and immobility time was recorded as 225, 220 and 206 seconds respectively (Group III to V). Administration of Ashwagandha extract with 3.5% withanolide glycosides with 5 and 7% enteric coating (60 mg/kg) after reserpine injection was more effective than lower percentage of coatings and immobility time was recorded as 195 and 180 seconds respectively (Group VI to VII). Administration of Ashwagandha extract with 3.5% withanolide glycosides with 10, 12 and 15% enteric coating (60 mg/kg) after reserpine injection was most effective and immobility time was recorded as 160, 142 and 140 seconds respectively (Group VIII to X). In case of fluoxetine standard at 10 mg/kg (Group XI), the immobility time was 120 seconds which is similar to normal control animals.

TABLE 3

Effect of Ashwagandha extract with 35% withanolide glycoside with different percentage of enteric coating on Immobility time in rats.

| Groups | Treatment | Immobility time in seconds |
|---|---|---|
| Group I | Normal control (Received only vehicle; 1% Tween 80 v/v p.o.). | 120 |
| Group II | Reserpine (6 mg/kg i.p) + Vehicle (1% Tween 80 v/v p.o.). | 250 |
| Group III | Reserpine (6 mg/kg i.p) + Ashwagandha extract with 35% withanolide glycosides (sample 3 prepared as per example 4) with 0.5% enteric coating (Dosage 20 mg/kg p.o.). | 200 |
| Group IV | Reserpine (6 mg/kg i.p) + Ashwagandha extract with 35% withanolide glycosides (sample 3 prepared as per example 4) with 1% enteric coating (Dosage 20 mg/kg p.o.). | 188 |
| Group V | Reserpine (6 mg/kg i.p) + Ashwagandha extract with 35% withanolide glycosides (sample 3 prepared as per example 4) with 3% enteric coating (Dosage 20 mg/kg p.o.). | 180 |
| Group VI | Reserpine (6 mg/kg i.p) + Ashwagandha extract with 35% withanolide glycosides (sample 3 prepared as per example 4) with 5% enteric coating (Dosage 20 mg/kg p.o.). | 171 |
| Group VII | Reserpine (6 mg/kg i.p) + Ashwagandha extract with 35% withanolide glycosides(sample 3 prepared as per example 4) with 7% enteric coating (Dosage 20 mg/kg p.o.). | 160 |
| Group VIII | Reserpine (6 mg/kg i.p) + Ashwagandha extract with 35% withanolide glycosides with 10% enteric coating (Dosage 20 mg/kg p.o). | 153 |
| Group IX | Reserpine (6 mg/kg i.p) + Ashwagandha extract with 35% withanolide glycosides (sample 3 prepared as per example 4)with 12% enteric coating (Dosage 20 mg/kg p.o). | 139 |
| Group X | Reserpine (6 mg/kg i.p) + Ashwagandha extract with 35% withanolide glycosides (sample 3 prepared as per example 4)with 15% enteric coating (Dosage 20 mg/kg p.o). | 136 |
| GroupXI | Reserpine(6 mg/kg i.p) + Fluoxetine (10 mg/kg p.o.). | 120 |

As shown in the Table 3, immobility time for normal control animals was 120 seconds. When reserpine was injected i.p., the animals got depressed and immobility time was increased to 250 seconds (Group II). Oral administration of Ashwagandha extract with 35% withanolide glycosides with 0.5%, 1% and 3% enteric coating (20 mg/kg) after reserpine injection was not much effective and immobility time was recorded as 200, 188 and 180 seconds respectively (Group III to V). Administration of Ashwagandha extract with 35% withanolide glycosides with 5 and 7% enteric coating (20 mg/kg) after reserpine injection was more effective than lower percentage of coatings and immobility time was recorded as 171 and 160 seconds respectively (Group VI to VII). Administration of Ashwagandha extract with 35% withanolide glycosides with 10, 12 and 15% enteric coating (20 mg/kg) after reserpine injection was most effective and immobility time was recorded as 153, 139 and 136 seconds respectively (Group VIII to X). In case of fluoxetine standard at 10 mg/kg (Group XI), the immobility time was 120 seconds which is similar to normal control animals.

TABLE 4

Effect of Ashwagandha extract with 80% withanolide glycoside with different percentage of enteric coating on Immobility time in rats.

| Groups | Treatment | Immobility time in seconds |
| --- | --- | --- |
| Group I | Normal control (Received only vehicle; 1% Tween 80 v/v p.o.). | 120 |
| Group II | Reserpine (6 mg/kg i.p) + Vehicle (1% Tween 80 v/v p.o.). | 250 |
| Group III | Reserpine (6 mg/kg i.p) + Ashwagandha extract with 80% withanolide glycosides (sample 5 prepared as per example 5)with 0.5% enteric coating (Dosage 20 mg/kg p.o). | 195 |
| Group IV | Reserpine (6 mg/kg i.p) + Ashwagandha extract with 80% withanolide glycosides (sample 5 prepared as per example 5)with 1% enteric coating (Dosage 20 mg/kg p.o). | 183 |
| Group V | Reserpine (6 mg/kg i.p) + Ashwagandha extract with 80% withanolide glycosides (sample 5 prepared as per example 5) with 3% enteric coating (Dosage 20 mg/kg p.o). | 173 |
| Group VI | Reserpine (6 mg/kg i.p) + Ashwagandha extract with 80% withanolide glycosides (sample 5 prepared as per example 5) with 5% enteric coating (Dosage 20 mg/kg p.o). | 160 |
| Group VII | Reserpine (6 mg/kg i.p) + Ashwagandha extract with 80% withanolide glycosides (sample 5 prepared as per example 5) with 7% enteric coating (Dosage 20 mg/kg p.o). | 145 |
| Group VIII | Reserpine (6 mg/kg i.p) + Ashwagandha extract with 80% withanolide glycosides (sample 5 prepared as per example 5) with 10% enteric coating (Dosage 20 mg/kg p.o). | 122 |
| Group IX | Reserpine (6 mg/kg i.p) + Ashwagandha extract with 80% withanolide glycosides (sample 5 prepared as per example 5) with 12% enteric coating (Dosage 20 mg/kg p.o). | 111 |
| Group X | Reserpine (6 mg/kg i.p) + Ashwagandha extract with 80% withanolide glycosides(sample 5 prepared as per example 5) with 15% enteric coating (Dosage 20 mg/kg p.o). | 109 |
| GroupXI | Reserpine(6 mg/kg i.p) + Fluoxetine (10 mg/kg p.o.). | 120 |

As shown in the Table 4, immobility time for normal control animals was 120 seconds. When reserpine was injected i.p., the animals got depressed and immobility time was increased to 250 seconds (Group II). Oral administration of Ashwagandha extract with 80% withanolide glycosides with 0.5%, 1% and 3% enteric coating (20 mg/kg) after reserpine injection was not much effective and immobility time was recorded as 195, 183 and 173 seconds respectively (Group III to V). Administration of Ashwagandha extract with 80% withanolide glycosides with 5 and 7% enteric coating (20 mg/kg) after reserpine injection was more effective than lower percentage of coatings and immobility time was recorded as 160 and 145 seconds respectively (Group VI to VII). Administration of Ashwagandha extract with 80% withanolide glycosides with 10, 12 and 15% enteric coating (20 mg/kg) after reserpine injection was most effective and immobility time was recorded as 122, 111 and 109 seconds respectively (Group VIII to X). In case of fluoxetine standard at 10 mg/kg (Group XI), the immobility time was 120 seconds which is similar to normal control animals.

Example 32

Antidiabetic Activity of Ashwagandha Extract in Streptozotocin Induced Diabetic Rats.

Different Ashwagandha extracts with and without coating were evaluated for antidiabetic activity in streptozotocin (STZ) induced diabetic rats. Male/Female albino wistar rats were maintained as per standard guidelines: housed in polypropylene cages, under 12 hour artificial light and dark cycles at a temperature of 24±2° C., given a standard pellet diet and water ad libitum. The animals were acclimatized to the animal house conditions for a week before beginning the experiment.

Diabetes was induced by injecting streptozotocin 35 mg/kg dissolved in 0.1M citrate buffer of pH 4.5, intraperitoneally. Five days after induction of diabetes (day 1 of the study), animals were fasted for 12 hours and the fasting blood glucose level (FBG) was estimated for diagnosing diabetic rats. Animals with FBG above 200 mg/dl were considered diabetic. The diabetic animals were randomly divided into 13 groups of six animals each. One normal group was also included comprising of six normal rats.

Following table 1 shows the treatment schedule given to the respective group of animals for 28 days.

TABLE 1

Treatment schedule.

| Groups | Drugs administered |
| --- | --- |
| Group I | Vehicle for 28 days (Normal control). |
| Group II | STZ + Vehicle for 28 days (Untreated control). |
| Group III | STZ + Glibenclamide (0.5 mg/kg) for 28 days (Standard). |
| Group IV | STZ + Regular Ashwagandha extract with minimum 1% withanolide glycosides (prepared as per example 23) (Dosage 100 mg/kg) for 28 days. |
| Group V | STZ + Regular Ashwagandha extract with 1% withanolide glycosides (prepared as per example 23)coated with Eudragit (prepared as per example 8) (Dosage 20 mg/kg) for 28 days. |
| Group VI | STZ + Ashwagandha root extract with 5% withanolide glycosides (sample 2 prepared as per example 6) (100 mg/kg.) for 28 days. |
| Group VII | STZ + Ashwagandha root extract with 5% withanolide glycosides (sample 2 prepared as per example 6) coated with Eudragit (prepared as per example 8) (20 mg/kg.) for 28 days. |

TABLE 1-continued

Treatment schedule.

| Groups | Drugs administered |
|---|---|
| Group VIII | STZ + Ashwagandha extract with minimum 3.5% withanolide glycosides (sample 2 prepared as per example 19) (Dosage 100 mg/kg) for 28 days. |
| Group IX | STZ + Ashwagandha extract with minimum 3.5% withanolide glycosides (sample 2 prepared as per example 19) coated with Eudragit (prepared as per example 20) (Dosage 20 mg/kg ) for 28 days. |
| Group X | STZ + Purified Ashwagandha root extract with 35% withanolide glycoside (sample 3 prepared as per example 4) (Dosage 100 mg/kg) for 28 days. |
| Group XI | STZ + Purified Ashwagandha root extract with 35% withanolide glycoside (sample 3 prepared as per example 4) coated with Eudragit (prepared as per example 8). (Dosage 20 mg/kg) for 28 days. |
| Group XII | STZ + Purified Ashwagandha root extract with 80% withanolide glycoside (sample 5 prepared as per example 5) (Dosage 100 mg/kg) for 28 days. |
| Group XIII | STZ + Purified Ashwagandha root extract with 80% withanolide glycoside (sample 5 prepared as per example 5) coated with Eudragit (prepared as per example 8). (Dosage 20 mg/kg) for 28 days. |

Fasting blood glucose level and body weight of rats was measured initially and then at Day 7, Day 14, Day 21 and Day 28 of the study.

TABLE 2

Fasting blood glucose (FBG) level of diabetic rats treated with Ashwagandha extract.

| | | Fasting Blood Glucose level (mg/dl) | | | | |
|---|---|---|---|---|---|---|
| Groups | Treatment | Day 1 (Initial) | Day 7 | Day 14 | Day 21 | Day 28 |
| Group I | Vehicle. | 74 | 75 | 74 | 75 | 75 |
| Group II | Untreated control. | 425 | 440 | 428 | 425 | 422 |
| Group III | Glibenclamide. | 422 | 380 | 245 | 196 | 124 |
| Group IV | Ashwagandha extract with minimum 1% withanolide glycosides (Dosage 100 mg/kg). | 423 | 401 | 374 | 337 | 302 |
| Group V | Ashwagandha extract with 1% withanolide glycosides coated with Eudragit (Dosage 20 mg/kg). | 428 | 400 | 375 | 336 | 300 |
| Group VI | Ashwagandha root extract with 5% withanolide glycosides (100 mg/kg.). | 425 | 395 | 324 | 284 | 224 |
| Group VII | Ashwagandha root extract with 5% withanolide glycosides coated with Eudragit (20 mg/kg.). | 423 | 394 | 323 | 282 | 222 |
| Group VIII | Ashwagandha extract with minimum 3.5% withanolide glycosides) (Dosage 100 mg/kg). | 425 | 320 | 272 | 209 | 163 |
| Group IX | Ashwagandha extract with minimum 3.5% withanolide glycosides coated with Eudragit (Dosage 20 mg/kg). | 426 | 318 | 270 | 206 | 162 |
| Group X | Purified Ashwagandha root extract with 35% withanolide glycoside (Dosage 100 mg/kg). | 424 | 365 | 240 | 164 | 120 |
| Group XI | Purified Ashwagandha root extract with 35% withanolide glycoside coated with Eudragit. (Dosage 20 mg/kg). | 424 | 363 | 239 | 163 | 119 |
| Group XII | Purified Ashwagandha root extract with 80% withanolide glycoside (Dosage 100 mg/kg). | 426 | 320 | 205 | 131 | 73 |
| Group XIII | Purified Ashwagandha root extract with 80% withanolide glycoside coated with Eudragit (Dosage 20 mg/kg). | 425 | 318 | 202 | 128 | 72 |

The diabetes was successfully induced in rats after STZ injection. The FBG of Group I rats (vehicle control) remained normal till end of the study. The FBG of untreated control group (Group II) remained high (above 400 mg/dl) during 28 days study period. The standard drug Glibenclamide (Group III) was effective in reducing the FBG level and it reduced from 422 to 124 mg/dl in 28 days treatment. Treatment with Ashwagandha extract with minimum 1% withanolide glycosides at 100 mg/kg dose (Group IV) reduced the FBG from 423 to 302 mg/dl whereas the same extract after coating with Eudragit (Group V) reduced the FBG from 428 to 300 mg/dl. Ashwagandha root extract with 5% withanolide glycosides (Group VI) at 100 mg/kg reduced the FBG from 425 to 224 mg/dl whereas coated product (Group VII) reduced the level from 423 to 222 mg/dl. Ashwagandha extract with minimum 3.5% withanolide glycosides (Group VIII) at 100 mg/kg and its coated product (Group IX) at 20 mg/kg dose reduced the FBG from 425 to 163 and 426 to 162 mg/dl respectively. The purified Ashwagandha root extract with 35% withanolide glycoside (Group X) given at 100 mg/kg reduced the FBG level from 424 to 120 mg/dl whereas purified Ashwagandha root extract with 35% withanolide glycoside coated with Eudragit (Group XI) given at 20 mg/kg for 28 days reduced the FBG from 424 to 119 mg/dl. Purified Ashwagandha root extract with 80% withanolide glycoside (Group XII) at 100 mg/kg and its coated product (Group XIII) at 20 mg/kg were most effective and reduced the FBG level from 426 to 73 and 425 to 72 mg/dl respectively.

Example 33

Antidiabetic Activity of Coated Ashwagandha Extracts in Different Doses in Streptozotocin Induced Diabetic Rats.

Different Ashwagandha extracts with coating in different dosages was evaluated for antidiabetic activity in experimental rats. Male/Female albino wistar rats were maintained as per standard guidelines: housed in polypropylene cages, under 12 hour artificial light and dark cycles at a temperature of 24±2° C., given a standard pellet diet and water ad libitum. The animals were acclimatized to the animal house conditions for a week before beginning the experiment.

Diabetes was induced by injecting streptozotocin 35 mg/kg dissolved in 0.1M citrate buffer of pH 4.5, intraperitoneally. Five days after induction of diabetes (day 1 of the study), animals were fasted for 12 hours and the fasting blood glucose level (FBG) was estimated for diagnosing diabetic rats. Animals with FBG above 200 mg/dl were considered diabetic. The diabetic animals were randomly divided into 13 groups of 4 animals each.

Following table shows the treatment schedule given to the respective group of animals for 28 days.

TABLE 1

| Groups | Treatment schedule Drugs administered |
|---|---|
| Group I | Vehicle for 28 days (Normal control). |
| Group II | STZ + Vehicle for 28 days (Untreated control). |
| Group III | STZ + Glibenclamide (0.5 mg/kg) for 28 days (Standard). |
| Group IV | Ashwagandha extract with minimum 3.5% withanolide glycosides (sample 2 prepared as per example19) coated with Eudragit (prepared as per example 20) (Dosage 1 mg/kg) for 28 days. |
| Group V | Ashwagandha extract with 3.5% withanolide glycosides (sample 2 prepared as per example 19 ) coated with Eudragit (prepared as per example 20) (Dosage 5 mg/kg) for 28 days. |
| Group VI | Ashwagandha extract with minimum 3.5% withanolide glycosides (sample 2 prepared as per example19) coated with Eudragit (prepared as per example 20) (Dosage 10 mg/kg) for 28 days. |
| Group VII | Ashwagandha extract with minimum 3.5% withanolide glycosides (sample 2 prepared as per example 19) coated with Eudragit (prepared as per example 20) (Dosage 20 mg/kg) for 28 days |
| Group VIII | Ashwagandha extract with minimum 3.5% withanolide glycosides (sample 2 prepared as per example 19) coated with Eudragit (prepared as per example 20) (Dosage 40 mg/kg) for 28 days. |
| Group IX | Purified Ashwagandha root extract with 35% withanolide glycoside (sample 3 prepared as per example 4) coated with Eudragit (prepared as per example 8). (Dosage 1 mg/kg) for 28 days. |
| Group X | Purified Ashwagandha root extract with 35% withanolide glycoside (sample 3 prepared as per example 4) coated with Eudragit (prepared as per example 8). (Dosage 5 mg/kg) for 28 days. |
| Group XI | Purified Ashwagandha root extract with 35% withanolide glycoside (sample 3 prepared as per example 4) coated with Eudragit (prepared as per example 8). (Dosage 10 mg/kg) for 28 days. |
| Group XII | Purified Ashwagandha root extract with 35% withanolide glycoside (sample 3 prepared as per example 4) coated with Eudragit (prepared as per example 8). (Dosage 20 mg/kg) for 28 days. |
| Group XIII | Purified Ashwagandha root extract with 35% withanolide glycoside (sample 3 prepared as per example 4) coated with Eudragit (prepared as per example 8). (Dosage 40 mg/kg) for 28 days. |

Fasting blood glucose level and body weight of rats was measured initially and then at Day 7, Day 14, Day 21 and Day 28 of the study.

TABLE 2

Fasting blood glucose (FBG) level of diabetic rats treated with Ashwagandha extract in different doses.

| Groups | Treatment | Fasting Blood Glucose level (mg/dl) | | | | |
|---|---|---|---|---|---|---|
| | | Day 1 (Initial) | Day 7 | Day 14 | Day 21 | Day 28 |
| Group I | Vehicle. | 73 | 74 | 73 | 74 | 74 |
| Group II | Untreated control. | 426 | 441 | 429 | 426 | 423 |
| Group III | Glibenclamide. | 423 | 381 | 246 | 197 | 125 |
| Group IV | Ashwagandha extract with 3.5% withanolide glycosides coated with Eudragit (Dosage 1 mg/kg) for 28 days. | 426 | 422 | 391 | 345 | 301 |
| Group V | Ashwagandha extract with 3.5% withanolide glycosides coated with Eudragit (Dosage 5 mg/kg) for 28 days. | 425 | 418 | 350 | 282 | 250 |
| Group VI | Ashwagandha extract with 3.5% withanolide glycosides coated with Eudragit (Dosage 10 mg/kg) for 28 days. | 426 | 386 | 318 | 274 | 202 |
| Group VII | Ashwagandha extract with 3.5% withanolide glycosides coated with Eudragit (Dosage 20 mg/kg) for 28 days. | 425 | 322 | 276 | 212 | 164 |
| Group VIII | Ashwagandha extract with 3.5% withanolide glycosides coated with Eudragit (Dosage 40 mg/kg) for 28 days. | 428 | 301 | 265 | 192 | 145 |
| Group IX | Purified Ashwagandha root extract with 35% withanolide glycoside coated with Eudragit (Dosage 1 mg/kg) for 28 days. | 426 | 420 | 352 | 284 | 250 |
| Group X | Purified Ashwagandha root extract with 35% withanolide glycoside coated with Eudragit (Dosage 5 mg/kg) for 28 days. | 425 | 410 | 318 | 241 | 200 |
| Group XI | Purified Ashwagandha root extract with 35% withanolide glycoside coated with Eudragit (Dosage 10 mg/kg) for 28 days. | 423 | 400 | 280 | 201 | 160 |
| Group XII | Purified Ashwagandha root extract with 35% withanolide glycoside coated with Eudragit. (Dosage 20 mg/kg) for 28 days. | 424 | 361 | 242 | 169 | 120 |
| Group XIII | Purified Ashwagandha root extract with 35% withanolide glycoside coated with Eudragit (Dosage 40 mg/kg) for 28 days. | 425 | 332 | 215 | 126 | 80 |

The FBG of Group I rats (vehicle control) remained normal till end of the study. The FBG of untreated control group (Group II) remained high (above 400 mg/dl) during 28 days study period. The standard drug Glibenclamide (Group III) was very effective in reducing the FBG level and it reduced from 423 to 125 mg/dl in 28 days treatment. Ashwagandha extract with 3.5% withanolide glycosides coated with Eudragit (Group IV to VIII) at 1, 5, 10, 20 and 40 mg/kg daily dosage for 28 days reduced the FBG level to 301, 250, 202, 164 and 145 mg/dl respectively. Purified Ashwagandha root extract with 35% withanolide glycoside coated with Eudragit was the most effective in reducing the FBG levels in rats. This product at 1, 5, 10, 20 and 40 mg/kg daily dosage (Group IX to XIII) reduced the FBG level to 250, 200, 160, 120 and 80 mg/dl respectively.

Example 34

Endurance Study.

Forced swimming test (FST) in rats was used to evaluate swimming endurance. The test included two exposures to a water tank (height, 40 cm; diameter, 22 cm, containing 25 cm of water at 25° C.) spaced 24 h apart. The first exposure was 10 min long (training) and the second, serving as the test session, was 5 min long. Each animal made vigorous attempts to get out of water bath during first couple of minutes and thereafter surrendered to experimental conditions and assumed a typical immobile posture (which is defined as when no additional activity is observed other than that required to keep the head above the water) with occasional escape attempts. The total duration of immobility was recorded.

24 male rats were divided into 4 groups comprising of 6 rats in each group. Experiment was performed as per above procedure and immobility time was recorded.

| Groups | Treatment | Immobility time (Sec) |
|---|---|---|
| Group I | Control. | 118.67 |
| Group II | Ashwagandha extract with 3.5% withanolide glycosides coated with Eudragit prepared as per | 77.33 |

| Groups | Treatment | Immobility time (Sec) |
|---|---|---|
| | example 20(Dosage 20 mg/kg). | |
| Group III | Amaranth extract with 9% nitrate content prepared as per example 27(Dosage 50 mg/kg). | 66.67 |
| Group IV | Ashwagandha extract with 3.5% withanolide glycosides coated with Eudragit + Amaranth extract with 9% nitrate content blended in 1:1 ratio prepared as per example 28 (Dosage50 mg/kg). | 52.67 |

For control group (Group I), the average immobility time for rats in 5 minutes test session was 118.67 seconds whereas after feeding with Ashwagandha extract with 3.5% withanolide glycosides coated with Eudragit (Group II) at 20 mg/kg increased the swimming endurance and immobility time got reduced to 77.33 seconds. The immobility time in rats fed with Amaranth extract with 9% nitrate content (Group III) at 50 mg/kg was recorded as 66.67 seconds. Feeding of rats with a combination of Ashwagandha extract with 3.5% withanolide glycosides coated with Eudragit and Amaranth extract with 9% nitrate content was most effective and it reduced the immobility time to 52.67 seconds.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. A composition comprising an extract of *Withania somnifera* for enhanced bioavailability of withanolide glycosides, wherein the extract of *Withania somnifera* for enhanced bioavailability of withanolide glycosides comprises about 30% to about 50% withanolide glycosides by weight; about 2% to about 30% saponins by weight; and about 0.001 to about 0.1% by weight of alkaloids.

2. The composition of claim 1, wherein the extract of *Withania somnifera* for enhanced bioavailability of withanolide glycosides comprises about 35% withanolide glycosides.

3. The composition of claim 1, wherein the extract of *Withania somnifera* for enhanced bioavailability of withanolide glycosides, is prepared by a method comprising:
   a) treating cleaned fresh roots of *Withania somnifera* with ammonia;
   b) extracting the product of step a) with methylene dichloride to obtain a filterate and a residue;
   c) washing the residue of step b) with water to obtain a washed residue then drying and powdering the washed residue to obtain a powder;
   d) extracting the powder of step c) with methanol at about 60° C. to about 70° C. to obtain a supernatant and a residue;
   e) concentrating and drying the supernatant of step d) to obtain a dried methanol extract powder;
   f) dissolving the dried methanol extract powder of step e) in water;
   g) clarifying the product of step f) to obtain a supernatant and a residue;
   h) loading the supernatant of step g) onto an adsorbing column; i) eluting the adsorbing column of step h) with water and then with 50% methanol;
   j) concentrating and drying the 50% methanol elute to obtain a powder,
   wherein the powder of step j) is the extract of *Withania somnifera* comprising about 30% to about 50% withanolide glycosides by weight; about 2% to about 30% saponins by weight; and about 0.001 to about 0.1% by weight of alkaloids.

4. The composition of claim 3, wherein the adsorbing column of step h) of the method of claim 3 is selected from the group consisting of silica, SP700, HP20, HP2MGL, SA10A, WA10, CRB03, CRB05, CR20, XAD 7HP, FP66, SK1B, and SP825L.

5. A dosage form comprising the composition of claim 1, wherein the dosage form is selected from the group consisting of capsule, tablet, mini tablet, granule, sachet, powder, paste, infusion, ampoule, solution, suspension, emulsion, pills, cream, enteric coated formulations and combinations thereof.

6. The dosage form of claim 5 comprising a dosage of about 200 mg to about 2000 mg of the extract of *Withania somnifera*.

7. A composition comprising an extract of *Withania somnifera* for enhanced bioavailability of withanolide glycosides, wherein the extract of *Withania somnifera* for enhanced bioavailability of withanolide glycosides comprises about 30% to about 80% withanolide glycosides by weight, about 2% to about 30% saponins by weight, and about 0.001% to about 0.1% alkaloids by weight.

8. The composition of claim 7, wherein the extract of *Withania somnifera* for enhanced bioavailability of withanolide glycosides comprises about 80% withanolide glycosides.

9. The composition of claim 7, wherein the extract of *Withania somnifera* for enhanced bioavailability of withanolide glycosides is prepared by a method comprising:
   a) treating cleaned fresh roots of *Withania somnifera* with ammonia;
   b) extracting the product of step a) with methylene dichloride to obtain a filterate and a residue;
   c) washing the residue of step b) with water to obtain a washed residue then drying and powdering the washed residue to obtain a powder;
   d) extracting the powder of step c) with methanol at about 60° C. to about 70° C. to obtain a supernatant and a residue;
   e) concentrating and drying the supernatant of step d) to obtain a dried methanol extract powder;
   f) dissolving the dried methanol extract powder of step e) in water;
   g) clarifying the product of step f) to obtain a supernatant and a residue;
   h) loading the supernatant of step g) onto an adsorbing column;
   i) eluting the adsorbing column of step h) with water and then with 50% methanol to obtain a 50% methanol elute;
   j) concentrating and drying the 50% methanol elute to obtain a dried methanol extract powder;
   k) dissolving the dried methanol extract powder of step j) in water and centrifuging to obtain a supernatant and a residue;
   l) loading the supernatant of step k) onto an adsorbing column;

m) eluting the adsorbing column of step l) with 10% methanol;
n) eluting the adsorbing column of step m) with 50% methanol to obtain a 50% methanol eluate;
o) dissolving the 50% methanol eluate of step) in methanol;
p) concentrating the product of step o);
q) adding acetone to the product of step p) to obtain a precipitate;
r) filtering and drying the precipitate of step q) to obtain a powder,
wherein the powder of step r) is the extract of roots of *Withania somnifera* comprising about 80% withanolide glycosides by weight; about 2% to about 30% saponins by weight; and about 0.001 to about 0.1% by weight of alkaloids.

10. The composition of claim 9, wherein the adsorbing column of step h) of the method of claim 9 is selected from the group consisting of silica, SP700, HP20, HP2MGL, SA10A, WA10, CRB03, CRB05, CR20, XAD 7HP, FP66, SK1B, and SP825L.

11. A dosage form comprising the composition of claim 7, wherein the dosage form is selected from the group consisting of capsule, tablet, mini tablet, granule, sachet, powder, paste, infusion, ampoule, solution, suspension, emulsion, pills, cream, enteric coated formulations and combinations thereof.

12. The dosage form of claim 11 comprising a dosage of about 200 mg to about 2000 mg of the extract of *Withania somnifera*.

* * * * *